US009447157B2

(12) United States Patent
Black et al.

(10) Patent No.: US 9,447,157 B2
(45) Date of Patent: Sep. 20, 2016

(54) NITRATION SHIELDING PEPTIDES AND METHODS OF USE THEREOF

(71) Applicant: Augusta University Research Institute, Inc., Augusta, GA (US)

(72) Inventors: Stephen M. Black, Martinez, GA (US); Ruslan Robertovich Rafitov, Evans, GA (US)

(73) Assignee: Augusta University Research Institute, Inc., Augusta, GA (US)

( * ) Notice: Subject to any disclaimer, the term of this patent is extended or adjusted under 35 U.S.C. 154(b) by 0 days.

(21) Appl. No.: 14/486,317

(22) Filed: Sep. 15, 2014

(65) Prior Publication Data

US 2015/0080288 A1    Mar. 19, 2015

Related U.S. Application Data

(60) Provisional application No. 61/877,650, filed on Sep. 13, 2013.

(51) Int. Cl.
| | | |
|---|---|---|
| *C07K 14/47* | (2006.01) | |
| *C07K 14/82* | (2006.01) | |
| *C12N 9/12* | (2006.01) | |

(52) U.S. Cl.
CPC ........... *C07K 14/47* (2013.01); *C07K 14/4702* (2013.01); *C07K 14/82* (2013.01); *C12N 9/1205* (2013.01); *C07K 2319/00* (2013.01); *C07K 2319/01* (2013.01); *C07K 2319/10* (2013.01); *C07K 2319/21* (2013.01); *C07K 2319/41* (2013.01); *C07K 2319/42* (2013.01); *C07K 2319/43* (2013.01)

(58) Field of Classification Search
CPC .. C07K 14/47; C07K 14/4702; C07K 14/82; C07K 2319/00; C07K 2319/01; C07K 2319/10; C07K 2319/21; C07K 2319/14; C07K 2319/42; C07K 2319/43; C12N 9/1205
USPC ......... 514/13.7, 13.8, 16.4, 17.7, 17.8, 19.3, 514/1.4, 1.9, 21.6, 6.9; 530/327, 328, 350
See application file for complete search history.

(56) References Cited

U.S. PATENT DOCUMENTS

| | | | | |
|---|---|---|---|---|
| 5,725,839 A | * | 3/1998 | Hsia ........................ | A61K 9/127 424/9.33 |
| 6,872,551 B2 | | 3/2005 | Lima | |
| 7,060,461 B2 | | 6/2006 | Butt | |
| 2005/0209147 A1 | * | 9/2005 | Laudanna ........ | A61K 47/48246 514/1.2 |

OTHER PUBLICATIONS

Acampora, et al., "Increased synthetic phenotype behavior of smooth muscle cells in response to in vitro balloon angioplasty injury model", Annals of Vascular Surgery 24:116-26 (2010).
Aggarwal, et al., "Attenuated vasodilatation in lambs with endogenous and exogenous activation of cGMP signaling: role of protein kinase G nitration." , J Cellular Physiol.,226(12):3104-13 (2011).
Atkinson, et al., "1H NMR and circular dichroism studies of the N-terminal domain of cyclic GMP dependent protein kinase: a leucine/isoleucine zipper" , Biochemistry 30:9387-95 (1991).
Barka, et al., "Transduction of TAT-HA-beta-galactosidase fusion protein into salivary gland-derived cells and organ cultures of the developing gland, and into rat submandibular gland in vivo" , J. Histochem. Cytochem., 48(11):1453-60 (2000).
Broughton, et al,, "Chronic hypoxia augments depolarization-induced Ca2+ sensitization in pulmonary vascular smooth muscle through superoxide-dependent stimulation of RhoA" , Am J Physiol., 298:L232-42 (2010).
Bruewer, et al., "RhoA, Rac1, and Cdc42 exert distinct effects on epithelial barrier via selective structural and biochemical modulation of junctional proteins and F-actin" , Am. J. Physiol. Cell Physiol., 287:C327-35 (2004).
Cai, "Suppression of nitrative damage by metallothionein in diabetic heart contributes to the prevention of cardiomyopathy" , Free Radio Biol Med., 41(6):851-61 (2006).
Casteel, et al., "A crystal structure of the cyclic GMP-dependent protein kinase I{beta} dimerization/docking domain reveals molecular details of 1soform-specific anchoring" , J Biolog Chem.,285:32684-8 (2010).
Chu, et al., "Activation by cyclic GMP binding causes an apparent conformational change in cGMP-dependent protein kinase" , J Biolog Chem., 272:31922-8 (1997).
Chu, et al., "Activation by autophosphorylation or cGMP binding produces a similar apparent conformational change in cGMP-dependent protein kinase" , J Biolog Chem., 273:14649-56 (1998).
Corbin, et al. "Studies of two different intrachain cGMP-binding sites of cGMP-dependent protein kinase" , J Biolog Chem., 258:11391-7 (1983).
Corbin, et al., "Studies of cGMP analog specificity and function of the two intrasubunit binding sites of cGMP-dependent protein kinase" , J Biolog Chem., 261:1208-14 (1986).
Corpas, et al., "Protein tyrosine nitration: a new challenge in plants" , Plant Signal Behav., 4(10):920-23 (2009).
Cruz, et al., "Chronic hypoxia induces right heart failure in caveolin-1-/- mice" , Am J Physiol., 302:H2518-27 (2012).
Derossi, et al., "The third helix of the Antennapedia homeodomain translocates through biological membranes" , J. Biol. Chem., 269(14):10444-50 (1994).

(Continued)

*Primary Examiner* — Julie Ha
(74) *Attorney, Agent, or Firm* — Pabst Patent Group LLP

(57) ABSTRACT

Nitration shielding peptides that reduce or prevent nitration of a protein of interest are disclosed. The peptide can serve as molecular sink for nitrating agents, block access of the nitrating agents to the target tyrosine on the protein of interest, serve as substrate for the nitrating agent (i.e., provide an alternative nitratable tyrosine residue), provide a nitrating agent neutralizing moiety such as antioxidant, or a combination thereof. The nitration shielding peptide can be a fusion protein that includes one or more additional domains such a protein transduction domain, a targeting signal, a purification tag, or any combination thereof. Exemplary nitration shielding peptides for reducing nitration of RhoA and PKG-1α, and methods of use thereof for treating pathologies, disease, and disorders associated with nitration of RhoA and PKG-1α, respectively are also provided.

11 Claims, 19 Drawing Sheets

(56) References Cited

OTHER PUBLICATIONS

Dusserre, et al., "Decrease in high density lipoprotein binding sites is associated with decrease in intracellular cholesterol efflux in dedifferentiated aortic smooth muscle cells", Biochim Blophysi Acta., 1212:235-244 (1994).
Feil, et al., "Distribution of cGMP-dependent protein kinase type I and its isoforms in the mouse brain and retina", Neuroscience, 135:863-8 (2005).
Francis, et al., "Arginine 75 in the pseudosubstrate sequence of type Ibeta cGMP-dependent protein kinase is critical for autoinhibition, although autophosphorylated serine 63 is outside this sequence", J Biol Chem., 271:20748-55 (1996).
Frankel and Pabo, "Cellular uptake of the tat protein from human immunodeficiency virus", Cell, 55(6):1189-93 (1988).
Garbers, "Guanylyl cyclase receptors and their endocrine, paracrine, and autocrine ligands", Cell 71:1-4 (1992).
Giordano, et al., "Combinatorial ligand-directed lung targeting", Proc Am Thorac Soc., 6(5):411-5 (2009).
Goeckeler,et al., "Myosin phosphatase and cofilin mediate cAMP/cAMP-dependent protein kinase-induced decline in endothelial cell isometric tension and myosin II regulatory light chain phosphorylation", J. Biol. Chem. 280:33083-95 (2005).
Harrington, et al., "Barrier dysfunction and RhoA activation are blunted by homocysteine and adenosine in pulmonary endothelium", Am. J. Physiol. Lung Cell Mol. Physiol. 287:L1091-7 (2004).
Heil, et al., "A catalytically active fragment of cGMP-dependent protein kinase. Occupation of its cGMP-binding sites does not affect its phosphotransferase activity", Eur J Biochem.,168:117-21 (1987).
Heo, et al., "Redox regulation of RhoA", Biochem., 45:14481-9 (2006).
Heo, et al., "Mechanism of redox-mediated guanine nucleotide exchange on redox-active Rho GTPases", J Biol. Chem. 280:31003-10 (2005).
Herranz, et al., "Integrin-linked kinase regulates vasomotor function by preventing endothelial nitric oxide synthase uncoupling: role in atherosclerosis", Circ Res., 110:439-49 (2012).
Ho, et al., "Synthetic protein transduction domains: enhanced transduction potential in vitro and in vivo", Cancer Res., 61(2):474-7 (2001).
Hofmann, et al., "cGMP-dependent protein kinase. Autophosphorylation changes the characteristics of binding site 1", Eur J Biochem., 147:361-5 (1985).
Hofmann, et, al., "Autophosphorylation of cGMP-dependent protein kinase is stimulated only by occupancy of one of the two cGMP binding sites", FEBS Lttrs., 164:350-4 (1983).
Huang, et al., "Lysophosphatidylcholine increases endothelial permeability: role of PKCalpha and RhoA cross talk", Am. J. Physiol. Lung Cell Mol. Physiol. 289:L176-85 (2005).
Ihara, et al., "Crystal structure of human RhoA in a dominantly active form complexed with a GTP analogue", J. Biol. Chem. 273:9656-66 (1998).
Ischiropoulos, "Biological selectivity and functional aspects of protein tyrosine nitration", Biochem Biophys Res Comm., 305:776-83 (2003).
Kawaguchi, et al., "Phagocytosis of latex particles by leucocytes. I. Dependence of phagocytosis on the size dnd surface potential of particles", Biomaterials, 7: 61-6 (1986).
Kawashima, et al., "Endothelial NO synthase overexpression inhibits lesion formation in mouse model of vascular remodeling", Arterioscler, Thromb, Vasc Biol., 21:201-7 (2001).
Klemm, et al., "Reduction of reactive oxygen species prevents hypoxia-induced CREB depletion in pulmonary artery smooth muscle cells", J Cardiovasc Pharmacol., 58:181-91(2011).
Krenis, and Strauss, "Effect of size and concentration of latex particles on respiration of human blood leucocytes", Proc. Soc. Exp. Med., 107:748-50 (1961).
Kumar, et al., "Redox homeostasis in mycobacteria:the key to tuberculosis control", Expert Rev. Mol. Med., 11: e19. doi:10.1017/S1462399409001112, 1-23 (2010).
Lincoln, et al., "Nitric oxide—cyclic GMP pathway regulates vascular smooth muscle cell phenotypic modulation: implications in vascular diseases", Acta Physiol Scand., 164:507-15 (1998).
Madamanchi, et al., "Differential activation of mitogenic signaling pathways in aortic smooth muscle cells deficient in superoxide dismutase isoforms", Arterioscler Thromb, Vasc Biol.,25:950-6 (2005).
Malakhov, et al., "SUMO fusions and SUMO-specific protease for efficient expression and purification of proteins", J. Struct. Funct. Genomics, 5:75-86 (2004).
Negash, et al., "Regulation of cGMP-dependent protein kinase-mediated vasodilation by hypoxia-induced reactive species in ovine fetal pulmonary veins", Am J Physiol Lung Mol Physiol., 293:L1012-20 (2007).
Negash, et al., "Role of cGMP-dependent protein kinase in regulation of pulmonary vascular smooth muscle cell adhesion and migration: effect of hypoxia", Am J Physiol Heart Circ Physiol., 297:H304-12 (2009).
Nie, et al., "Endothelial nitric oxide synthase-dependent tyrosine nitration of prostacyclin synthase in diabetes in vivo", Diabetes 55, 3133-41 (2006).
Nisbet, et al., "The role of NADPH oxidase in chronic intermittent hypoxia-induced pulmonary hypertension in mice", Am J Respiratory Cell MolBiol., 40:601-9 (2009).
Nozik-Grayceket al., "Role of reactive oxygen species in chronic hypoxia-induced pulmonary hypertension and vascular remodeling", Adv Exp Med Biol., 618:101-12 (2007).
Osborne, et al., "Crystal structure of cGMP-dependent protein kinase reveals novel site of interchain communication", Structure, 19:1317-27 (2011).
Peluffo and Radi, "Biochemistry of protein tyrosine nitration in cardiovascular pathology", Cardiovasc. Res., 75(2):291-302 (2007).
Pilz, et al., "Role of cyclic GMP in gene regulation", Front Biosci. 10:1239-68 (2005).
Rajotte and Ruoslahti, "Membrane dipeptidase is the receptor for a lung-targeting peptide identified by in vivo phage display", J. Biol. Chem., 23;274(17):11593-8 (1999).
Redondo-Horcajo, et al., "Cyclosporine A-induced nitration of tyrosine 34 MnSOD in endothelial cells: role of mitochondrial superoxide", Cardiovasc Res., 87:356-65 (2010).
Reed, et al., "Fast and slow cyclic nucleotide-dissociation sites in cAMP-dependent protein kinase are transposed in type Ibeta cGMP-dependent protein kinase", J Biol Chem., 271, 17570-17575 (1996).
Reynolds, et al, "Tau nitration occurs at tyrosine 29 in the fibrillar lesions of Alzheimer's disease and other tauopathies", J Neuroscience, 26(42):10636-45 (2006).
Roberts, et al., Nitrative and oxidative stress in toxicology and disease Toxicol. Sci., 112(1):4-16 (2006).
Rudic, et al., "Direct evidence for the importance of endothelium-derived nitric oxide in vascular remodeling", J Clinic Invest., 101:731-6 (1998).
Rudt and Muller, "In vitro phagocytosis assay of nano- and microparticles by chemiluminescence. I. Effect of analytical parameters, particle size and particle concentration", J. Contr. Rel., 22(3):263-72 (1992).
Savvides, et al., "Crystal structure of the antioxidant enzyme glutathione reductase inactivated by peroxynitrite", J Biol Chem., 277:2779-84 (2002).
Scheffzek, et al., "The Rac-RhoGDI complex and the structural basis for the regulation of Rho proteins by RhoGDI", Nat. Struct. Biol., 7:122-6 (2000).
Shen, et al., "Endothelial contractile cytoskeleton and microvascular permeability", Cell Health Cytoskelet. 43-50 (2009).
Shimizu, et al., "An open conformation of switch I revealed by the crystal structure of a Mg2+-free form of RHOA complexed with GDP. Implications for the GDP/GTP exchange mechanism", J Biol. Chem. 275:18311-7 (2000).

(56) References Cited

OTHER PUBLICATIONS

Takio, et al., "Guanosine cyclic 3',5'-phosphate dependent protein kinase, a chimeric protein homologous with two separate protein families", Biochemistry 23:4207-18 (1984).

Uhler, "Cloning and expression of a novel cyclic GMP-dependent protein kinase from mouse brain", J Biolog Chem., 268:13586-91 (1993).

Vaandrager, et al., "Molecular properties and biological functions of cGMP-dependent protein kinase II.", Front Biosci. 10:2150-64 (2005).

Venselaar, et al., "Homology modelling and spectroscopy, a never-ending love story", Eur. Biophys. J. 39:551-563 (2010).

Wadia, et al., "Tranaducibla TAT-HA fusogenic peptide enhances escape of TAT-fusion proteins after lipid raft micropinocytosis", Nat Med., 10:310-5 (2004).

Wagner, et al., "Targeting of polyplexes: toward synthetic virus vector systems", Adv. Gen., 53:333-54 (2005).

Wang, et al., "Manganese superoxide dismutase inhibits neointima formation through attenuation of migration and proliferation of vascular smooth muscle cells", Free Radic Biol Med., 52:173-181 (2012).

Weinberger, et al., "The toxicology of inhaled nitric oxide", Toxicol. Sci.. 59:5-16 (2001).

Wender, et al., "The design, synthesis, and evaluation of molecules that enable or enhance cellular uptake: peptoid molecular transporters", PNAS, 97(24):13003-8 (2000).

Wojciak-Stothard, et al., "Rho and Rac but not Cdc42 regulate endothelial cell permeability", J. Cell Sci., 114:1343-55 (2001).

Wolfe, et al., "Cyclic nucleotides and disease", Curr Opin Cell Biol., 1:215-9 (1989b).

Wolfe, et al., "Characterization of a novel isozyme of cGMP-dependent protein kinase from bovine aorta", J Biolog Chem., 264:7734-41 (1989).

Zhao, et al., "Persistent eNOS activation secondary to caveolin-1 deficiency induces pulmonary hypertension in mice and humans through PKG nitration", J Clin Invest., 119:2009-18 (2009).

Zhao, et al., "Progressive cyclic nucleotide-induced conformational changes in the cGMP-dependent protein kinase studied by small angle X-ray scattering in solution", J Biolog Chem., 272:31929-36 (1997).

Zuo, et al., "Enhanced expression and purification of membrane proteins by SUMO fusion in *Escherichia coli*", J. Struct. Funct. Genomics, 6:103-111 (2005).

Yarbrough, et al., "AMPylation of Rho GTPases by Vibrio VopS disrupts effector binding and downstream signaling", *Science*, 323:269-72 (2009).

\* cited by examiner

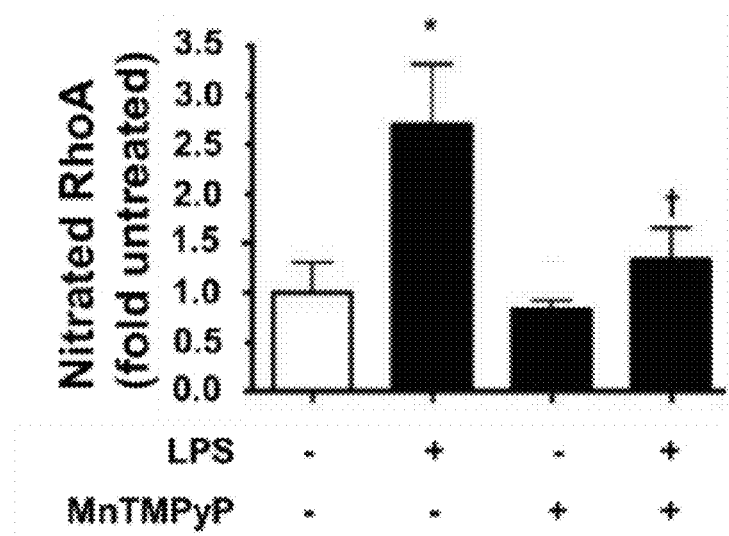
FIG. 2B
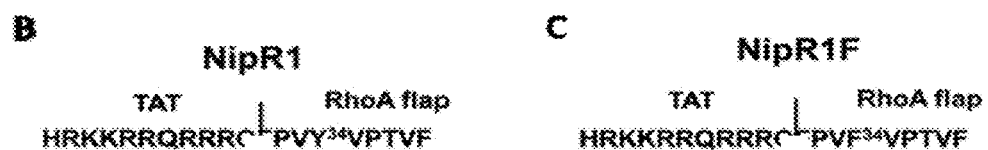
FIG. 3A-C

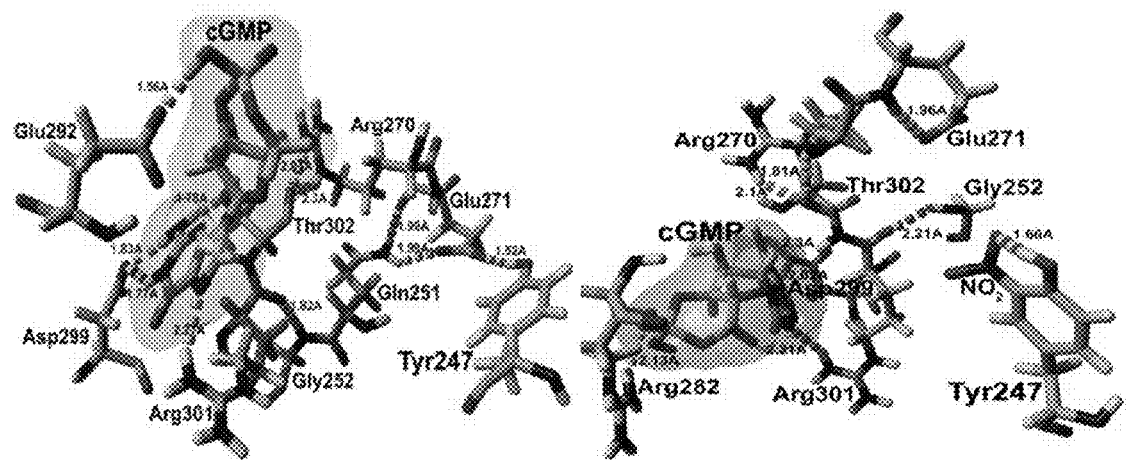
FIG. 20C                    FIG. 20D

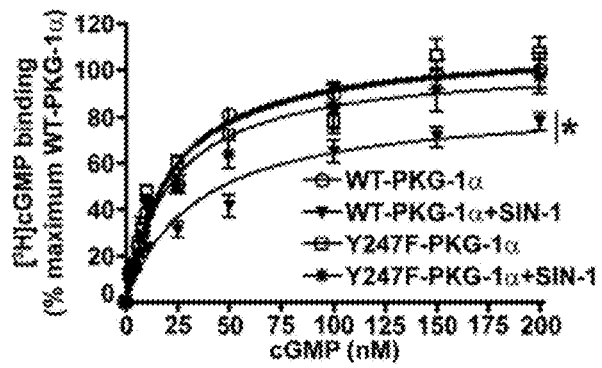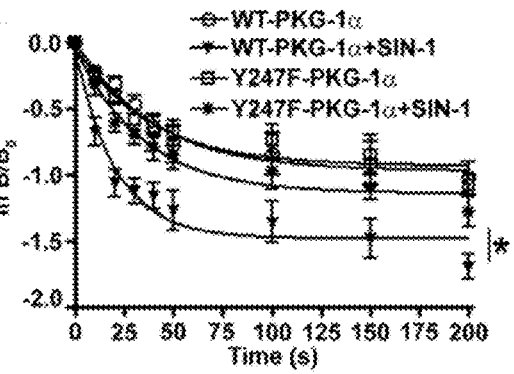
FIG. 21A  FIG. 21B
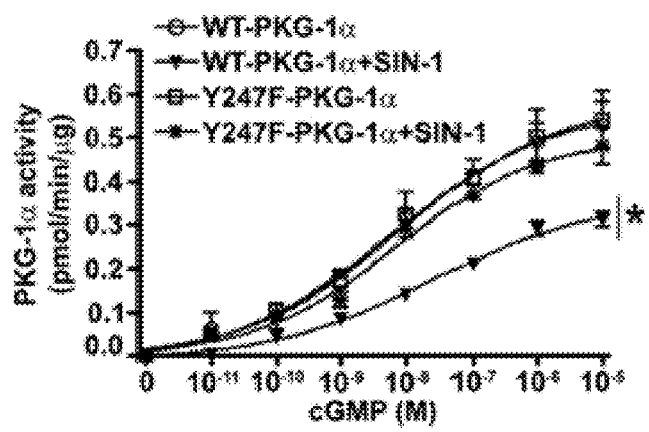
FIG. 21C

SEQUENCE LISTING

```
<160> NUMBER OF SEQ ID NOS: 42

<210> SEQ ID NO 1
<211> LENGTH: 11
<212> TYPE: PRT
<213> ORGANISM: Human immunodeficiency virus

<400> SEQUENCE: 1

Tyr Gly Arg Lys Lys Arg Arg Gln Arg Arg Arg
1               5                   10

<210> SEQ ID NO 2
<211> LENGTH: 9
<212> TYPE: PRT
<213> ORGANISM: Human immunodeficiency virus

<400> SEQUENCE: 2

Arg Lys Lys Arg Arg Gln Arg Arg Arg
1               5

<210> SEQ ID NO 3
<211> LENGTH: 10
<212> TYPE: PRT
<213> ORGANISM: Human immunodeficiency virus

<400> SEQUENCE: 3
```

```
His Arg Lys Lys Arg Arg Gln Arg Arg Arg
1               5                   10

<210> SEQ ID NO 4
<211> LENGTH: 7
<212> TYPE: PRT
<213> ORGANISM: Artificial Sequence
<220> FEATURE:
<223> OTHER INFORMATION: Poly-ARG protein transduction domain.

<400> SEQUENCE: 4

Arg Arg Arg Arg Arg Arg Arg
1               5

<210> SEQ ID NO 5
<211> LENGTH: 12
<212> TYPE: PRT
<213> ORGANISM: Human immunodeficiency virus

<400> SEQUENCE: 5

Arg Arg Gln Arg Arg Thr Ser Lys Leu Met Lys Arg
1               5                   10

<210> SEQ ID NO 6
<211> LENGTH: 27
<212> TYPE: PRT
<213> ORGANISM: Human immunodeficiency virus

<400> SEQUENCE: 6

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 7
<211> LENGTH: 29
<212> TYPE: PRT
<213> ORGANISM: Human immunodeficiency virus

<400> SEQUENCE: 7

Trp Glu Ala Lys Leu Ala Lys Ala Leu Ala Lys Ala Leu Ala Lys His
1               5                   10                  15

Leu Ala Lys Ala Leu Ala Lys Ala Leu Lys Cys Glu Ala
            20                  25

<210> SEQ ID NO 8
<211> LENGTH: 16
<212> TYPE: PRT
<213> ORGANISM: Human immunodeficiency virus

<400> SEQUENCE: 8

Arg Gln Ile Lys Ile Trp Phe Gln Asn Arg Arg Met Lys Trp Lys Lys
1               5                   10                  15

<210> SEQ ID NO 9
<211> LENGTH: 20
<212> TYPE: PRT
<213> ORGANISM: Influenza A virus

<400> SEQUENCE: 9

Gly Asp Ile Met Gly Glu Trp Gly Asn Glu Ile Phe Gly Ala Ile Ala
1               5                   10                  15

Gly Phe Leu Gly
            20
```

<210> SEQ ID NO 10
<211> LENGTH: 35
<212> TYPE: PRT
<213> ORGANISM: Influenza A virus

<400> SEQUENCE: 10

Arg Arg Arg Arg Arg Arg Arg Arg Arg Arg Gly Glu Gly Asp Ile
1               5                   10                  15

Met Gly Glu Trp Gly Asn Glu Ile Phe Gly Ala Ile Ala Gly Phe Leu
            20                  25                  30

Gly Gly Glu
        35

<210> SEQ ID NO 11
<211> LENGTH: 13
<212> TYPE: PRT
<213> ORGANISM: Homo sapiens

<400> SEQUENCE: 11

Cys Gly Phe Glu Cys Val Arg Gln Cys Pro Glu Arg Cys
1               5                   10

<210> SEQ ID NO 12
<211> LENGTH: 88
<212> TYPE: PRT
<213> ORGANISM: Staphylococcus aureus

<400> SEQUENCE: 12

His Asp Glu Ala Gln Gln Asn Ala Phe Tyr Gln Val Leu Asn Met Pro
1               5                   10                  15

Asn Leu Asn Ala Asp Gln Arg Asn Gly Phe Ile Gln Ser Leu Lys Asp
            20                  25                  30

Asp Pro Ser Gln Ser Ala Asn Val Leu Gly Glu Ala His Asp Glu Ala
        35                  40                  45

Gln Gln Asn Ala Phe Tyr Gln Val Leu Asn Met Pro Asn Leu Asn Ala
    50                  55                  60

Asp Gln Arg Asn Gly Phe Ile Gln Ser Leu Lys Asp Asp Pro Ser Gln
65                  70                  75                  80

Ser Ala Asn Val Leu Gly Glu Ala
                85

<210> SEQ ID NO 13
<211> LENGTH: 91
<212> TYPE: PRT
<213> ORGANISM: Staphylococcus aureus

<400> SEQUENCE: 13

His Asp Glu Ala Gln Gln Asn Ala Phe Tyr Gln Val Leu Asn Met Pro
1               5                   10                  15

Asn Leu Asn Ala Asp Gln Arg Asn Gly Phe Ile Gln Ser Leu Lys Asp
            20                  25                  30

Asp Pro Ser Gln Ser Ala Asn Val Leu Gly Glu Ala His Asp Glu Ala
        35                  40                  45

Gln Gln Asn Ala Phe Tyr Gln Val Leu Asn Met Pro Asn Leu Asn Ala
    50                  55                  60

Asp Gln Arg Asn Gly Phe Ile Gln Ser Leu Lys Asp Asp Pro Ser Gln
65                  70                  75                  80

Ser Ala Asn Val Leu Gly Glu Ala Gly Glu Gly

```
                      85                  90

<210> SEQ ID NO 14
<211> LENGTH: 8
<212> TYPE: PRT
<213> ORGANISM: Artificial Sequence
<220> FEATURE:
<223> OTHER INFORMATION: FLAG tag.

<400> SEQUENCE: 14

Asp Tyr Lys Asp Asp Asp Asp Lys
1               5

<210> SEQ ID NO 15
<211> LENGTH: 6
<212> TYPE: PRT
<213> ORGANISM: Influenza virus

<400> SEQUENCE: 15

Tyr Pro Tyr Asp Val Pro
1               5

<210> SEQ ID NO 16
<211> LENGTH: 10
<212> TYPE: PRT
<213> ORGANISM: Artificial Sequence
<220> FEATURE:
<223> OTHER INFORMATION: MYC tag

<400> SEQUENCE: 16

Ile Leu Lys Lys Ala Thr Ala Tyr Ile Leu
1               5                   10

<210> SEQ ID NO 17
<211> LENGTH: 10
<212> TYPE: PRT
<213> ORGANISM: Artificial Sequence
<220> FEATURE:
<223> OTHER INFORMATION: MYC tag.

<400> SEQUENCE: 17

Glu Gln Lys Leu Ile Ser Glu Glu Asp Leu
1               5                   10

<210> SEQ ID NO 18
<211> LENGTH: 9
<212> TYPE: PRT
<213> ORGANISM: Homo sapiens
<220> FEATURE:
<221> NAME/KEY: MISC_FEATURE
<222> LOCATION: (2)..(5)
<223> OTHER INFORMATION: Xaa = any amino acid
<220> FEATURE:
<221> NAME/KEY: MISC_FEATURE
<222> LOCATION: (8)..(8)
<223> OTHER INFORMATION: Xaa = threonine or serine

<400> SEQUENCE: 18

Gly Xaa Xaa Xaa Xaa Gly Lys Xaa Cys
1               5

<210> SEQ ID NO 19
<211> LENGTH: 193
<212> TYPE: PRT
<213> ORGANISM: Homo sapiens

<400> SEQUENCE: 19
```

```
Met Ala Ala Ile Arg Lys Lys Leu Val Ile Val Gly Asp Gly Ala Cys
1               5                   10                  15

Gly Lys Thr Cys Leu Leu Ile Val Phe Ser Lys Asp Gln Phe Pro Glu
            20                  25                  30

Val Tyr Val Pro Thr Val Phe Glu Asn Tyr Val Ala Asp Ile Glu Val
        35                  40                  45

Asp Gly Lys Gln Val Glu Leu Ala Leu Trp Asp Thr Ala Gly Gln Glu
    50                  55                  60

Asp Tyr Asp Arg Leu Arg Pro Leu Ser Tyr Pro Asp Thr Asp Val Ile
65                  70                  75                  80

Leu Met Cys Phe Ser Ile Asp Ser Pro Asp Ser Leu Glu Asn Ile Pro
                85                  90                  95

Glu Lys Trp Thr Pro Glu Val Lys His Phe Cys Pro Asn Val Pro Ile
            100                 105                 110

Ile Leu Val Gly Asn Lys Lys Asp Leu Arg Asn Asp Glu His Thr Arg
                115                 120                 125

Arg Glu Leu Ala Lys Met Lys Gln Glu Pro Val Lys Pro Glu Glu Gly
            130                 135                 140

Arg Asp Met Ala Asn Arg Ile Gly Ala Phe Gly Tyr Met Glu Cys Ser
145                 150                 155                 160

Ala Lys Thr Lys Asp Gly Val Arg Glu Val Phe Glu Met Ala Thr Arg
                165                 170                 175

Ala Ala Leu Gln Ala Arg Arg Gly Lys Lys Lys Ser Gly Cys Leu Val
            180                 185                 190

Leu

<210> SEQ ID NO 20
<211> LENGTH: 11
<212> TYPE: PRT
<213> ORGANISM: Homo sapiens

<400> SEQUENCE: 20

Gln Phe Pro Glu Val Tyr Val Pro Thr Val Phe
1               5                   10

<210> SEQ ID NO 21
<211> LENGTH: 10
<212> TYPE: PRT
<213> ORGANISM: Homo sapiens

<400> SEQUENCE: 21

Phe Pro Glu Val Tyr Val Pro Thr Val Phe
1               5                   10

<210> SEQ ID NO 22
<211> LENGTH: 10
<212> TYPE: PRT
<213> ORGANISM: Homo sapiens

<400> SEQUENCE: 22

Gln Phe Pro Val Tyr Val Pro Thr Val Phe
1               5                   10

<210> SEQ ID NO 23
<211> LENGTH: 9
<212> TYPE: PRT
<213> ORGANISM: Homo sapiens

<400> SEQUENCE: 23
```

```
Phe Pro Val Tyr Val Pro Thr Val Phe
  1               5
```

```
<210> SEQ ID NO 24
<211> LENGTH: 21
<212> TYPE: PRT
<213> ORGANISM: Human immunodeficiency virus

<400> SEQUENCE: 24

His Arg Lys Lys Arg Arg Gln Arg Arg Gln Phe Pro Glu Val Tyr
  1               5                  10                  15

Val Pro Thr Val Phe
             20
```

```
<210> SEQ ID NO 25
<211> LENGTH: 20
<212> TYPE: PRT
<213> ORGANISM: Human immunodeficiency virus

<400> SEQUENCE: 25

His Arg Lys Lys Arg Arg Gln Arg Arg Gln Phe Pro Val Tyr Val
  1               5                  10                  15

Pro Thr Val Phe
             20
```

```
<210> SEQ ID NO 26
<211> LENGTH: 671
<212> TYPE: PRT
<213> ORGANISM: Homo sapiens

<400> SEQUENCE: 26

Met Ser Glu Leu Glu Glu Asp Phe Ala Lys Ile Leu Met Leu Lys
  1               5                  10                  15

Glu Arg Ile Lys Glu Leu Glu Lys Arg Leu Ser Glu Lys Glu Glu
                 20                  25                  30

Ile Gln Glu Leu Lys Arg Lys Leu His Lys Cys Gln Ser Val Leu Pro
                 35                  40                  45

Val Pro Ser Thr His Ile Gly Pro Arg Thr Thr Arg Ala Gln Gly Ile
 50                  55                          60

Ser Ala Glu Pro Gln Thr Tyr Arg Ser Phe His Asp Leu Arg Gln Ala
 65                  70                  75                  80

Phe Arg Lys Phe Thr Lys Ser Glu Arg Ser Lys Asp Leu Ile Lys Glu
                     85                  90                  95

Ala Ile Leu Asp Asn Asp Phe Met Lys Asn Leu Glu Leu Ser Gln Ile
                100                 105                 110

Gln Glu Ile Val Asp Cys Met Tyr Pro Val Glu Tyr Gly Lys Asp Ser
                115                 120                 125

Cys Ile Ile Lys Glu Gly Asp Val Gly Ser Leu Val Tyr Val Met Glu
            130                 135                 140

Asp Gly Lys Val Glu Val Thr Lys Glu Gly Val Lys Leu Cys Thr Met
145                 150                 155                 160

Gly Pro Gly Lys Val Phe Gly Glu Leu Ala Ile Leu Tyr Asn Cys Thr
                165                 170                 175

Arg Thr Ala Thr Val Lys Thr Leu Val Asn Val Lys Leu Trp Ala Ile
                180                 185                 190

Asp Arg Gln Cys Phe Gln Thr Ile Met Met Arg Thr Gly Leu Ile Lys
                195                 200                 205

His Thr Glu Tyr Met Glu Phe Leu Lys Ser Val Pro Thr Phe Gln Ser
```

-continued

```
            210                 215                 220
Leu Pro Glu Glu Ile Leu Ser Lys Leu Ala Asp Val Leu Glu Thr
225                 230                 235                 240

His Tyr Glu Asn Gly Glu Tyr Ile Ile Arg Gln Gly Ala Arg Gly Asp
                245                 250                 255

Thr Phe Phe Ile Ile Ser Lys Gly Thr Val Asn Val Thr Arg Glu Asp
                260                 265                 270

Ser Pro Ser Glu Asp Pro Val Phe Leu Arg Thr Leu Gly Lys Gly Asp
            275                 280                 285

Trp Phe Gly Glu Lys Ala Leu Gln Gly Glu Asp Val Arg Thr Ala Asn
        290                 295                 300

Val Ile Ala Ala Glu Ala Val Thr Cys Leu Val Ile Asp Arg Asp Ser
305                 310                 315                 320

Phe Lys His Leu Ile Gly Gly Leu Asp Asp Val Ser Asn Lys Ala Tyr
                325                 330                 335

Glu Asp Ala Glu Ala Lys Ala Lys Tyr Glu Ala Glu Ala Ala Phe Phe
                340                 345                 350

Ala Asn Leu Lys Leu Ser Asp Phe Asn Ile Ile Asp Thr Leu Gly Val
            355                 360                 365

Gly Gly Phe Gly Arg Val Glu Leu Val Gln Leu Lys Ser Glu Glu Ser
        370                 375                 380

Lys Thr Phe Ala Met Lys Ile Leu Lys Lys Arg His Ile Val Asp Thr
385                 390                 395                 400

Arg Gln Gln Glu His Ile Arg Ser Glu Lys Gln Ile Met Gln Gly Ala
                405                 410                 415

His Ser Asp Phe Ile Val Arg Leu Tyr Arg Thr Phe Lys Asp Ser Lys
                420                 425                 430

Tyr Leu Tyr Met Leu Met Glu Ala Cys Leu Gly Gly Glu Leu Trp Thr
            435                 440                 445

Ile Leu Arg Asp Arg Gly Ser Phe Glu Asp Ser Thr Thr Arg Phe Tyr
        450                 455                 460

Thr Ala Cys Val Val Glu Ala Phe Ala Tyr Leu His Ser Lys Gly Ile
465                 470                 475                 480

Ile Tyr Arg Asp Leu Lys Pro Glu Asn Leu Ile Leu Asp His Arg Gly
                485                 490                 495

Tyr Ala Lys Leu Val Asp Phe Gly Phe Ala Lys Lys Ile Gly Phe Gly
                500                 505                 510

Lys Lys Thr Trp Thr Phe Cys Gly Thr Pro Glu Tyr Val Ala Pro Glu
            515                 520                 525

Ile Ile Leu Asn Lys Gly His Asp Ile Ser Ala Asp Tyr Trp Ser Leu
        530                 535                 540

Gly Ile Leu Met Tyr Glu Leu Leu Thr Gly Ser Pro Pro Phe Ser Gly
545                 550                 555                 560

Pro Asp Pro Met Lys Thr Tyr Asn Ile Ile Leu Arg Gly Ile Asp Met
                565                 570                 575

Ile Glu Phe Pro Lys Lys Ile Ala Lys Asn Ala Ala Asn Leu Ile Lys
                580                 585                 590

Lys Leu Cys Arg Asp Asn Pro Ser Glu Arg Leu Gly Asn Leu Lys Asn
            595                 600                 605

Gly Val Lys Asp Ile Gln Lys His Lys Trp Phe Glu Gly Phe Asn Trp
        610                 615                 620

Glu Gly Leu Arg Lys Gly Thr Leu Thr Pro Pro Ile Ile Pro Ser Val
625                 630                 635                 640
```

```
Ala Ser Pro Thr Asp Thr Ser Asn Phe Asp Ser Phe Pro Glu Asp Asn
                645                 650                 655

Asp Glu Pro Pro Pro Asp Asp Asn Ser Gly Trp Asp Ile Asp Phe
            660                 665                 670

<210> SEQ ID NO 27
<211> LENGTH: 9
<212> TYPE: PRT
<213> ORGANISM: Homo sapiens

<400> SEQUENCE: 27

Gly Ala Leu Arg Gln Lys Asn Val Lys
1               5

<210> SEQ ID NO 28
<211> LENGTH: 19
<212> TYPE: PRT
<213> ORGANISM: Artificial Sequence
<220> FEATURE:
<223> OTHER INFORMATION: PKG-1 alpha nitration shielding peptide
<220> FEATURE:
<221> NAME/KEY: MISC_FEATURE
<222> LOCATION: (17)..(17)
<223> OTHER INFORMATION: Xaa = any amino acid

<400> SEQUENCE: 28

His Arg Lys Lys Arg Arg Gln Arg Arg Gly Ala Leu Arg Gln Lys
1               5                   10                  15

Xaa Val Lys

<210> SEQ ID NO 29
<211> LENGTH: 9
<212> TYPE: PRT
<213> ORGANISM: Homo sapiens
<220> FEATURE:
<221> NAME/KEY: MISC_FEATURE
<222> LOCATION: (7)..(7)
<223> OTHER INFORMATION: Xaa = any amino acid.
<220> FEATURE:
<221> NAME/KEY: MISC_FEATURE
<222> LOCATION: (9)..(9)
<223> OTHER INFORMATION: 3-carboxy-2,2,5,5-tetramethyl-3-pyrrolin-1-
      yloxy(nitroxide)-amide

<400> SEQUENCE: 29

Gly Ala Leu Arg Gln Lys Xaa Val Lys
1               5

<210> SEQ ID NO 30
<211> LENGTH: 19
<212> TYPE: PRT
<213> ORGANISM: Artificial Sequence
<220> FEATURE:
<223> OTHER INFORMATION: Nitration shielding peptide
<220> FEATURE:
<221> NAME/KEY: MISC_FEATURE
<222> LOCATION: (17)..(17)
<223> OTHER INFORMATION: Xaa = any amino acid
<220> FEATURE:
<221> NAME/KEY: MISC_FEATURE
<222> LOCATION: (19)..(19)
<223> OTHER INFORMATION: 3-carboxy-2,2,5,5-tetramethyl-3-pyrrolin-1-
      yloxy(nitroxide)-amide

<400> SEQUENCE: 30

His Arg Lys Lys Arg Arg Gln Arg Arg Gly Ala Leu Arg Gln Lys
1               5                   10                  15
```

Xaa Val Lys

```
<210> SEQ ID NO 31
<211> LENGTH: 14
<212> TYPE: PRT
<213> ORGANISM: Homo sapiens
<220> FEATURE:
<221> NAME/KEY: MISC_FEATURE
<222> LOCATION: (9)..(9)
<223> OTHER INFORMATION: Xaa = 3-nitrotyrosine

<400> SEQUENCE: 31

Ser Lys Asp Gln Phe Pro Glu Val Xaa Val Pro Thr Val Phe
1               5                   10

<210> SEQ ID NO 32
<211> LENGTH: 18
<212> TYPE: PRT
<213> ORGANISM: Homo sapiens

<400> SEQUENCE: 32

Leu Ala Asp Val Leu Glu Glu Thr His Tyr Glu Asn Gly Glu Tyr Ile
1               5                   10                  15

Ile Arg

<210> SEQ ID NO 33
<211> LENGTH: 16
<212> TYPE: PRT
<213> ORGANISM: Homo sapiens

<400> SEQUENCE: 33

Gln Ile Met Gln Gly Ala His Ser Asp Phe Ile Val Arg Leu Tyr Arg
1               5                   10                  15

<210> SEQ ID NO 34
<211> LENGTH: 18
<212> TYPE: PRT
<213> ORGANISM: Homo sapiens
<220> FEATURE:
<221> NAME/KEY: MISC_FEATURE
<222> LOCATION: (15)..(15)
<223> OTHER INFORMATION: X = 3-nitrotyrosine

<400> SEQUENCE: 34

Leu Ala Asp Val Leu Glu Glu Thr His Tyr Glu Asn Gly Glu Xaa Ile
1               5                   10                  15

Ile Arg

<210> SEQ ID NO 35
<211> LENGTH: 20
<212> TYPE: PRT
<213> ORGANISM: Homo sapiens

<400> SEQUENCE: 35

His Arg Lys Lys Arg Arg Gln Arg Arg Gln Phe Pro Val Phe Val
1               5                   10                  15

Pro Thr Val Phe
            20

<210> SEQ ID NO 36
<211> LENGTH: 21
<212> TYPE: PRT
<213> ORGANISM: Artificial Sequence
<220> FEATURE:
<223> OTHER INFORMATION: RhoA nitration shielding peptide
```

```
<220> FEATURE:
<221> NAME/KEY: MISC_FEATURE
<222> LOCATION: (11)..(11)
<223> OTHER INFORMATION: Xaa = any amino acid

<400> SEQUENCE: 36

His Arg Lys Lys Arg Arg Gln Arg Arg Arg Xaa Phe Pro Glu Val Tyr
1               5                   10                  15

Val Pro Thr Val Phe
            20

<210> SEQ ID NO 37
<211> LENGTH: 20
<212> TYPE: PRT
<213> ORGANISM: Artificial Sequence
<220> FEATURE:
<223> OTHER INFORMATION: RhoA nitration shielding peptide
<220> FEATURE:
<221> NAME/KEY: MISC_FEATURE
<222> LOCATION: (11)..(11)
<223> OTHER INFORMATION: Xaa = any amino acid

<400> SEQUENCE: 37

His Arg Lys Lys Arg Arg Gln Arg Arg Arg Xaa Phe Pro Val Tyr Val
1               5                   10                  15

Pro Thr Val Phe
            20

<210> SEQ ID NO 38
<211> LENGTH: 20
<212> TYPE: PRT
<213> ORGANISM: Artificial Sequence
<220> FEATURE:
<223> OTHER INFORMATION: PKG-1 alpha nitration shielding peptide
<220> FEATURE:
<221> NAME/KEY: MISC_FEATURE
<222> LOCATION: (11)..(11)
<223> OTHER INFORMATION: Xaa = is any amino acid
<220> FEATURE:
<221> NAME/KEY: MISC_FEATURE
<222> LOCATION: (18)..(18)
<223> OTHER INFORMATION: Xaa = is any amino acid

<400> SEQUENCE: 38

His Arg Lys Lys Arg Arg Gln Arg Arg Arg Xaa Gly Ala Leu Arg Gln
1               5                   10                  15

Lys Xaa Val Lys
            20

<210> SEQ ID NO 39
<211> LENGTH: 20
<212> TYPE: PRT
<213> ORGANISM: Artificial Sequence
<220> FEATURE:
<223> OTHER INFORMATION: Nitration shielding peptide
<220> FEATURE:
<221> NAME/KEY: MISC_FEATURE
<222> LOCATION: (11)..(11)
<223> OTHER INFORMATION: Xaa = any amino acid
<220> FEATURE:
<221> NAME/KEY: MISC_FEATURE
<222> LOCATION: (18)..(18)
<223> OTHER INFORMATION: Xaa = any amino acid
<220> FEATURE:
<221> NAME/KEY: MISC_FEATURE
<222> LOCATION: (20)..(20)
<223> OTHER INFORMATION: 3-carboxy-2,2,5,5-tetramethyl-3-pyrrolin-1-
      yloxy(nitroxide)-amide

<400> SEQUENCE: 39
```

```
His Arg Lys Lys Arg Arg Gln Arg Arg Arg Xaa Gly Ala Leu Arg Gln
1               5                   10                  15

Lys Xaa Val Lys
            20

<210> SEQ ID NO 40
<211> LENGTH: 9
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (9)..(9)
<223> OTHER INFORMATION: 3-carboxy-2,2,5,5-tetramethyl-3-pyrrolin-1-
      yloxy(nitroxide)-amide

<400> SEQUENCE: 40

Gly Ala Leu Arg Gln Lys Asn Val Lys
1               5

<210> SEQ ID NO 41
<211> LENGTH: 15
<212> TYPE: PRT
<213> ORGANISM: Artificial Sequence
<220> FEATURE:
<223> OTHER INFORMATION: synthetic peptide antigen
<220> FEATURE:
<221> NAME/KEY: MISC_FEATURE
<222> LOCATION: (5)..(5)
<223> OTHER INFORMATION: Xaa = 3-nitrotyrosine

<400> SEQUENCE: 41

Glu Asn Gly Glu Xaa Ile Ile Arg Gln Gly Ala Arg Gly Asp Cys
1               5                   10                  15

<210> SEQ ID NO 42
<211> LENGTH: 15
<212> TYPE: PRT
<213> ORGANISM: Artificial Sequence
<220> FEATURE:
<223> OTHER INFORMATION: synthetic polypeptide

<400> SEQUENCE: 42

Glu Asn Gly Glu Tyr Ile Ile Arg Gln Gly Ala Arg Gly Asp Cys
1               5                   10                  15
```

NITRATION SHIELDING PEPTIDES AND METHODS OF USE THEREOF

CROSS-REFERENCE TO RELATED APPLICATIONS

This application claims the benefit of U.S. Ser. No. 61/877,650, filed on Sep. 13, 2013, which is incorporated herein in its entirety.

STATEMENT REGARDING FEDERALLY SPONSORED RESEARCH OR DEVELOPMENT

This invention was made with government support under grant no. P01HL0101902 awarded by the National Institutes of Health. The Government has certain rights in the invention.

REFERENCE TO SEQUENCE LISTING

The Sequence Listing submitted Mar. 13, 2016, as a text file named "GRU_2014-005a_ST25.txt," created on Feb. 5, 2016, and having a size of 19,000 bytes is hereby incorporated by reference pursuant to 37 C.F.R. §1.52(e)(5).

FIELD OF THE INVENTION

The field of the invention generally relates to compositions for blocking protein nitration and methods of use thereof for treating pathologies associated with protein nitration.

BACKGROUND OF THE INVENTION

Nitric oxide (NO) is a gas that in animals participates in a wide variety of functions in the cardiovascular, immune and nervous systems. It has an unpaired electron in its $\pi$ orbital, and this characteristic gives NO special properties. Nitric oxide can react with different macromolecules (proteins, lipids, nucleic acids, etc.) and diffuse through cell membranes. The term reactive nitrogen species (RNS) has also been introduced in the biological literature to designate nitric oxide and other NO-related molecules, such as S-nitrosothiols (RSNOs), peroxynitrite (ONOO—), dinitrogen trioxide ($N_2O_3$) and nitrogen dioxide ($NO_2$) among others, which have relevant roles in multiple physiological processes of animal and plant cells. These molecules directly or indirectly are involved in post-translational modifications in cell signaling under physiological and pathological conditions including binding to metal centers, S-nitrosylation of thiol groups and nitration of tyrosine (Corpas, et al., *Plant Signal Behav.*, 4(10): 920-923 (2009)).

For example, tyrosine nitrated proteins constitute a widespread finding in the normal or diseased cardiovascular (CV) system (Peluffo and Radi, *Cardiovasc. Res.*, 75(2):291-302 (2007)). In the various compartments and tissues of the CV system, namely, intravascular space, vessel wall and myocardium, nitrated proteins have been detected with a variety of techniques (reviewed in Bartesaghi, et al., *Amino Acids*, 32:501-515 (2007) and Ye, et al., *Methods Enzymol.*, 269: 201-209 (1996)), and have been implicated in various cardiovascular and pulmonary pathologies. In many cases the protein target that is nitrated is an enzyme or signaling protein whose function is altered by nitration.

Current methods of treating protein nitration and the myriad of pathologies associated therewith are insufficient.

Therefore, it is an object of the invention to provide compositions and methods for preventing, blocking or otherwise reducing protein nitration.

It is also an object of the invention to use compositions for blocking or reducing protein nitration to treat or prevent one or more symptoms of a disease associated with or caused by protein nitration.

It is a further object of the invention to reduce nitration-associated endothelial hyperpermeability in a subject.

It is also a further object of the invention to reduce or prevent nitration-associated increases in vascular smooth muscle cell proliferation in a subject.

It is a further object of the invention to treat one of more symptoms of vascular pulmonary hypertension and other vascular diseases and disorders in a subject.

SUMMARY OF THE INVENTION

Methods of treating or preventing one or more symptoms of a disease or disorder characterized by elevated nitration of a protein in a subject are disclosed. The methods can include administering to a subject an effective amount of a pharmaceutical composition including a nitration shielding peptide to prevent or reduce protein nitration in the subject. Exemplary diseases that can be treated or prevented include coagulation disorders, platelet dysfunction, diabetes, atherosclerosis, inflammation, stroke, neurodegenerative disorders, cancer, sepsis, septic myocardial dysfunction, myocardial infarction, cardiovascular disease, liver disease, Alzheimer's disease, Parkinson's disease, ischemia, chronic heart failure, Amyotrophic Lateral Sclerosis, endothelial dysfunction, and combinations thereof.

Nitration shielding peptides that reduce or prevent nitration of a protein of interest are provided. The nitration shielding peptides include a nitration shielding domain including between 5-100 amino acids inclusive that reduces, inhibits, or prevents nitration of at least one tyrosine residue in the protein of interest. The nitration shielding domain can include, a fragment of the full-length protein of interest or a functional variant thereof. The fragment can include at least one tyrosine residue that can be nitrated in the protein of interest. In some embodiments, the nitration shielding peptide does not include a fragment of the full-length protein of interest, does not include a tyrosine residue, or a combination thereof. Preferably, the peptide binds to the protein of interest. The peptide can serve as molecular sink for nitrating agents, block access of the nitrating agents to the target tyrosine on the protein of interest, serve as a substrate for the nitrating agent (i.e., provide an alternative nitratable tyrosine residue), provide a nitrating agent neutralizing moiety such as an antioxidant, or a combination thereof.

The nitration shielding peptide can be a fusion protein that includes one or more additional domains such as a protein transduction domain, a targeting signal, a purification tag, or any combination thereof. The nitration shielding peptide can include an antioxidant moiety, a charge neutralizing moiety, or a combination thereof. In a preferred embodiment, the nitration shielding peptide is targeted to endothelium or vascular smooth muscle, particularly lung endothelium or vascular smooth muscle.

Pharmaceutical compositions including one or more nitration shielding peptides and a pharmaceutically acceptable carrier, and methods of administration thereof to a subject are also disclosed. In a preferred embodiment, the peptides are formulated for mucosal delivery and administered to the lungs.

In a particular embodiment, the nitration shielding peptide reduces or prevents nitration of RhoA. It has been discovered that nitration increases the activity of RhoA. Therefore, reducing or blocking nitration of RhoA prevents or reduces over-activation of RhoA. Exemplary nitration shielding peptides including SEQ ID NO:20 or a functional variant thereof are provided. Preferably, the nitration shielding domain of a RhoA nitration shielding peptide is a fragment of RhoA or functional variant thereof that blocks protein nitration of RhoA and is not full-length RhoA. For example, the nitration shielding domain can consist of SEQ ID NO:20 or a variant thereof with at least 70% sequence identity to SEQ ID NO:20. Typically, the nitration shielding domain comprises the tyrosine of SEQ ID NO:20, which corresponds to the nitratable tyrosine of RhoA (Y34).

The RhoA nitration shielding peptide can be a fusion protein. For example, the RhoA nitration shielding peptide can include a protein transduction domain such as HIV TAT, a targeting signal, for example a lung targeting signal such as GFE-1, or a combination thereof. The RhoA nitration shielding polypeptide can also include an antioxidant moiety such as nitroxide (3-carboxy-2,2,5,5-tetramethyl-3-pyrrolin-1-yloxy), biopterin (2-N-Acetyl-1',2'-di-O-acetyl-6-biopterin), quinone (9,10-Dihydro-4,5-dihydroxy-9,10-dioxo-2-anthracenecarboxylic acid) or porphyrin (MnTMPyp), a charge neutralizing moiety such as amide, or a combination thereof.

Methods of using RhoA nitration shielding peptides to reduce or prevent endothelial hyperpermeability in a subject are also disclosed. The methods typically include administering to the subject an effective amount of a pharmaceutical composition including the nitration shielding peptide to prevent or reduce protein nitration of RhoA. In a particular embodiment, the endothelial hyperpermeability is in the lung endothelium. The endothelial hyperpermeability is typically characterized by nitration of Y34 of SEQ NO:19 or a corresponding tyrosine in a homolog or variant thereof in endothelial cells of the subject.

The compositions can also be used to treat or prevent one or more symptoms of a disease or disorder characterized by elevated nitration of RhoA in subject. The one or more symptoms can include elevated levels of activated RhoA, impaired lung endothelial barrier function, weight loss, cell infiltration into the bronchoalveolar lavage fluid (BALF), alveolar damage, an elevated number of neutrophils, red blood cells, or a combination thereof in the alveolar or interstitial space, formation of hyaline membranes, septal thickening, debris accumulation in the alveoli, increased myeloperoxidase (MPO) presence in the alveolar space, reduced MPO activity in lung cells, and combinations thereof. The disease or disorder can be, for example, acute lung injury (ALI), acute respiratory distress syndrome (ARDS), ventilator-induced lung injury (VILI), ventilator-associated lung injury (VALI), lung infections, trauma, ischaemia-reperfusion injury, sepsis, diabetes, thrombosis, cancer or a combination thereof. The compositions can be administered alone or in combination with one or more additional therapeutic agents, including but not limited to, an antihistamine, anti-VEGF, activated protein C, a PKC inhibitor, a Rho inhibitor, or combinations thereof.

In another particular embodiment, the nitration shielding peptide can reduce or prevent nitration of PKG-1α. It has been discovered that nitration of PKG-1α reduces its kinase function. Therefore, reducing or blocking nitration of PKG-1α can increase PKG-1α activity, or prevent a reduction in PKG-1α activity. The PKG-1α nitration shielding peptide can include a nitration shielding domain including SEQ ID NO:27 or a functional variant thereof, wherein the nitration shielding peptide blocks protein nitration of PKG-1α. For example, the nitration shielding peptide can consist of SEQ ID NO:27 or a variant thereof with at 70% sequence identity to SEQ ID NO:27.

The PKG-1α nitration shielding peptide can be a fusion protein. For example, the PKG-1α nitration shielding peptide can include a protein transduction domain such as HIV TAT, a targeting signal, for example a lung targeting signal such as GFE-1, or a combination thereof. The PKG-1α nitration shielding polypeptide can also include an antioxidant moiety such as nitroxide (3-carboxy-2,2,5,5-tetramethyl-3-pyrrolin-1-yloxy), biopterin (2-N-Acetyl-1',2'-di-O-acetyl-6-biopterin), quinone (9,10-Dihydro-4,5-dihydroxy-9,10-dioxo-2-anthracenecarboxylic acid) or porphyrin (MnTMPyp), a charge neutralizing moiety such as amide, or a combination thereof.

Methods of using the PKG-1α nitration shielding peptides to treat or prevent loss of a contractile-like phenotype in smooth muscle cells in a subject are also provided. The methods typically include administering to the subject an effective amount of a pharmaceutical composition including the PKG-1α nitration shielding peptide to prevent or reduce protein nitration of PKG-1α. In a preferred embodiment, the smooth muscle cells are vascular smooth muscle cells in the lungs. The loss of contractile-like phenotype is typically characterized by nitration of Y247 of SEQ NO:26 or a corresponding tyrosine in a homolog or variant thereof.

The compositions can also be used to treat or prevent one or more symptoms of a disease or disorder characterized by reduced levels of PKG-1α kinase activity or reduced intracellular cGMP levels in a subject. The one or more symptoms can include an increase in vascular smooth muscle cell proliferation, or a phentotype thereof, or an increase in expression of a marker thereof (e.g., vimentin expression, or nuclear levels of protein PCNA); an increase in vascular smooth muscle cell metabolic activity; a decrease in expression of contractile markers such as MYH and Calponin-1 in vascular smooth muscle cell; a decrease a contractile phenotype (e.g., spinal shape morphology) or a marker thereof (e.g., SM22-α) or localization thereof (e.g., to actin stress fibers) in vascular smooth muscle cells; and combinations thereof. The disease or disorder can be, for example, pulmonary hypertension, atherosclerosis, restenosis, hypoxia, vasoconstriction, vascular remodeling, vascular dysfunction, a coronary artery disease, erectile dysfunction, hypoxemic respiratory failure, or a combination thereof. The compositions can be administered alone or in combination with a second therapeutic agent including but not limited to inhaled NO therapy for pulmonary hypertension, NO donors, such as nitroglycerin, isosorbide dinitrate, or isosorbide mononitrate for coronary artery diseases; cGMP specific phosphodiesterase-5 inhibitors, sildenafil and tadalafil for the treatment of pulmonary hypertension and erectile dysfunction; and B-type natriuretic peptides for hypoxemic respiratory failure.

BRIEF DESCRIPTION OF THE DRAWINGS

FIGS. 2A-B are histograms, showing (A) RhoA activity (fold untreated) for HLMVEC in the presence of 1 EU/ml LPS for 4 h (LPS) and/or the peroxynitrite scavenger, MnTMPyP; and (B) RhoA nitration (fold untreated) for HLMVEC in the presence of 1 EU/ml LPS for 4 h (LPS) and/or MnTMPyP. Data are mean±SEM; *=P<0.05 vs. untreated; †=P<0.05 vs. LPS alone.

FIGS. 3A-C are schematic representations of (A) the peptide fragment of RhoA identified as having a nitrated tyrosine (Y34), (B) the NipR1 peptide HRKKRRQRRRQF-PVYVPTVF (SEQ ID NO:25) and (C) the NipR1F peptide HRKKRRQRRRQFPVFVPTVF (SEQ ID NO:35).

FIG. 7D is a histogram showing nitrated RhoA Activity (fold untreated) untreated (UT) and in the presence of NipR1 and NipR1F. Data are mean±SEM; N=4-6. *:P<0.05 vs. Control; †: P<0.05 vs. LPS alone.

FIG. 19C shows 3-NT-Y247-PKG-1α/PKG-1α levels (Fold control) from humans without (Control) and with pulmonary hypertension (PH), respectively. Data are mean±SEM, n=4-5, *p<0.05 vs. untreated WT-PKG-1α for (A), control lambs for (B) and normal human lung for (C); † p<0.05 vs. WT-PKG-1α+SIN-1 (A).

FIGS. 20A-D are cartoon representations of the molecular structure of human PKG-1α regulatory domain, based upon the crystal structures of the catalytic domain of PKA (PDB 2CPK) and the PKG-1α PKA regulatory domain (PDB 1NE4). FIG. 20A shows the results of AutoDock to dock two cGMP molecules to the cGMP binding sites (A and B) and an ATP molecule to the ATP binding site. FIG. 20B shows the comparison of the structure of PKG-1α and a homology model of PKG-1α produced by the YASARA software. FIG. 20C shows prediction of the affinity of cGMP for the cGMP binding site B in the PKG-1α homology model under control conditions. FIG. 20D shows an equivalent model under nitrative stress conditions. The addition of a $NO_2$ group to Y247 is predicted to decrease the total hydrogen bonding energy between cGMP and PKG-1α from 91.930 kJ/mol to 54.02 kJ/mol (C and D).

FIGS. 21A-C are line graphs, showing (A) [$^3$H]cGMP binding (% maximum WT-PKG-1α) over cGMP concentration (0-200 nM) for WT-PKG-1α (⊖), WT-PKG-1α with SIN-1 (▼), Y247F-PKG-1α (⊟) and Y247F-PKG-1α+ SIN-1 (✶), respectively; (B) [$^3$H]cGMP dissociation (plotted as 1 n($B/B_0$), with $B_0$ as the initial [$^3$H]cGMP bound] and B as the [$^3$H]cGMP remaining bound at time (S)) for WT-PKG-1α (⊖), WT-PKG-1α with SIN-1 (▼), Y247F-PKG-1α (⊟) and Y247F-PKG-1α+SIN-1 (✶), at various time points (0-200 seconds), respectively; and (C) enzyme kinetics of the phosphor-transferase reaction of PKG-1α, plotted as PKG-1α activity (pmol/min/μg) for WT-PKG-1α (⊖), WT-PKG-1α with SIN-1 (▼), Y247F-PKG-1α (⊟) and Y247F-PKG-1α+SIN-1 (✶), at varying concentrations of cGMP (0-10 μM), respectively. Each value represents the mean of three separate experiments. Data are mean±SEM, n=3. *p<0.05 vs. untreated WT-PKG-1α.

DETAILED DESCRIPTION OF THE INVENTION

I. Definitions

Figure 1A:
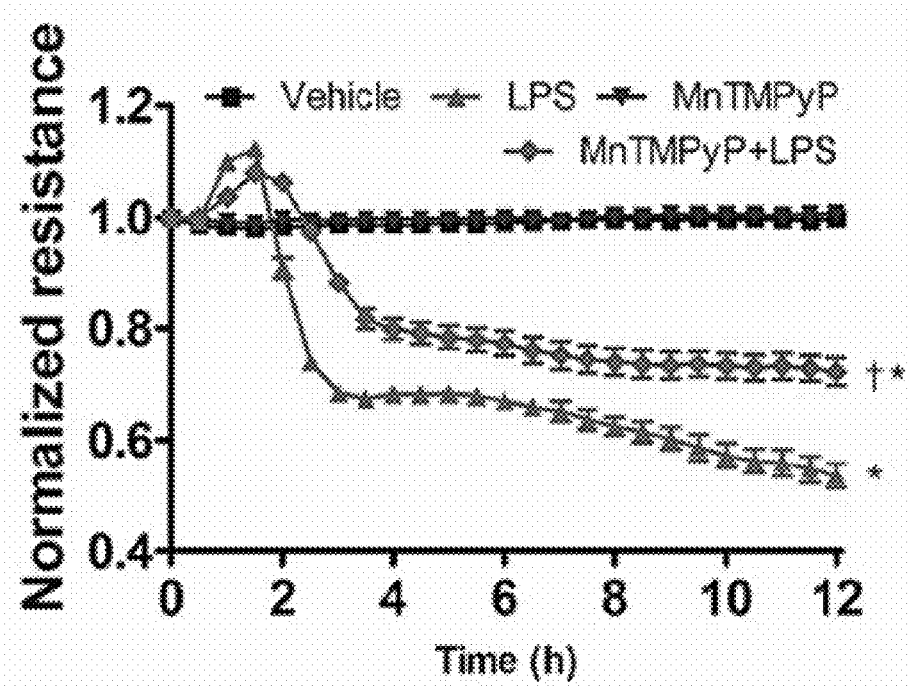
FIGS. 1A-C are scatter dot plots showing transendothelial resistance (normalized resistance) over time (h) for human lung microvascular endothelial cells (HLMVEC), (A) in the presence of vehicle alone (■), 1 EU/ml Lipopolysaccharide, (LPS ▲), the peroxynitrite scavenger, MnTMPyP (▼) and 25 μM MnTMPyP with 1 EU/ml LPS (♦), respectively; (B) in the presence of vehicle alone (■), 1 EU/ml LPS, (LPS ▲), 100 μM the iNOS specific inhibitor, 1400 W (▼) 100 μM 1400 W with 1 EU/ml LPS (♦), the general NOS inhibitor, ETU (●) and 1 EU/ml LPS with ETU (✕), respectively; and (C) in the presence of scrambled siRNA (Scrambled siRNA ■), Scrambled siRNA with LPS (Scrambled+LPS ▲), siRNA for the eNOS protein (eNOS siRNA ▼), and siRNA for the eNOS protein with LPS (eNOS siRNA+LPS ♦), respectively. Data are mean±SEM; N=3-4. *=P<0.05 vs. untreated; †=P<0.05 vs. LPS alone.

As used herein, "treat" means to prevent, reduce, decrease, or ameliorate one or more symptoms, characteristics or comorbidities of an age-related disease, disorder or condition; to reverse the progression of one or more symptoms, characteristics or comorbidities of an age related disorder; to halt the progression of one or more symptoms, characteristics or comorbidities of an age-related disorder; to prevent the occurrence of one or more symptoms, characteristics or comorbidities of an age-related disorder; to inhibit the rate of development of one or more symptoms, characteristics or comorbidities or combinations thereof.

The terms "individual," "subject," and "patient" are used interchangeably herein, and refer to a mammal, including, but not limited to, rodents, simians, and humans.

The terms "reduce", "inhibit", "alleviate" and "decrease" are used relative to a control. One of skill in the art would readily identify the appropriate control to use for each experiment. For example a decreased response in a subject or cell treated with a compound is compared to a response in subject or cell that is not treated with the compound.

The terms "increase", "induce", "activate" and "improve" are used relative to a control. One of skill in the art would readily identify the appropriate control to use for each experiment. For example an increased response in a subject or cell treated with a compound is compared to a response in subject or cell that is not treated with the compound.

The term "polypeptides" includes proteins and fragments thereof. Polypeptides are disclosed herein as amino acid residue sequences. Those sequences are written left to right in the direction from the amino to the carboxy terminus. In accordance with standard nomenclature, amino acid residue sequences are denominated by either a three letter or a single letter code as indicated as follows: Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine (Gly, G), Histidine (H is, H), Isoleucine (Ile, I), Leucine (Leu, L), Lysine (Lys, K), Methionine (Met, M), Phenylalanine (Phe, F), Praline (Pro, P), Serine (Ser, S), Threonine (Thr, T), Tryptophan (Trp, W), Tyrosine (Tyr, Y), and Valine (Val, V).

"Variant" refers to a polypeptide or polynucleotide that differs from a reference polypeptide or polynucleotide, but retains essential properties. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more modifications (e.g., substitutions, additions, and/or deletions). A substituted or inserted amino acid residue may or may not be one encoded by the genetic code. A variant of a polypeptide may be naturally occurring such as an allelic variant, or it may be a variant that is not known to occur naturally.

Modifications and changes can be made in the structure of the polypeptides of the disclosure and still obtain a molecule having similar characteristics as the polypeptide (e.g., a conservative amino acid substitution). For example, certain amino acids can be substituted for other amino acids in a sequence without appreciable loss of activity. Because it is the interactive capacity and nature of a polypeptide that defines that polypeptide's biological functional activity, certain amino acid sequence substitutions can be made in a polypeptide sequence and nevertheless obtain a polypeptide with like properties.

In making such changes, the hydropathic index of amino acids can be considered. The importance of the hydropathic amino acid index in conferring interactive biologic function on a polypeptide is generally understood in the art. It is known that certain amino acids can be substituted for other amino acids having a similar hydropathic index or score and still result in a polypeptide with similar biological activity. Each amino acid has been assigned a hydropathic index on the basis of its hydrophobicity and charge characteristics. Those indices are: isoleucine (+4.5); valine (+4.2); leucine (+3.8); phenylalanine (+2.8); cysteine/cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is believed that the relative hydropathic character of the amino acid determines the secondary structure of the resultant polypeptide, which in turn defines the interaction of the polypeptide with other molecules, such as enzymes, substrates, receptors, antibodies, antigens, and the like. It is known in the art that an amino acid can be substituted by another amino acid having a similar hydropathic index and still obtain a functionally equivalent polypeptide. In such changes, the substitution of amino acids whose hydropathic indices are within ±2 is preferred, those within ±1 are particularly preferred, and those within ±0.5 are even more particularly preferred.

Substitution of like amino acids can also be made on the basis of hydrophilicity, particularly, where the biological functional equivalent polypeptide or peptide thereby created is intended for use in immunological embodiments. The following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); proline (−0.5±1); threonine (−0.4); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent polypeptide. In such changes, the substitution of amino acids whose hydrophilicity values are within ±2 is preferred, those within ±1 are particularly preferred, and those within ±0.5 are even more particularly preferred.

As outlined above, amino acid substitutions are generally based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include (original residue: exemplary substitution): (Ala: Gly, Ser), (Arg: Lys), (Asn: Gln, His), (Asp: Glu, Cys, Ser), (Gln: Asn), (Glu: Asp), (Gly: Ala), (His: Asn, Gln), (Ile: Leu, Val), (Leu: Ile, Val), (Lys: Arg), (Met: Leu, Tyr), (Ser: Thr), (Thr: Ser), (Tip: Tyr), (Tyr: Trp, Phe), and (Val: Ile, Leu). Embodiments of this disclosure thus contemplate functional or biological equivalents of a polypeptide as set forth above. In particular, embodiments of the polypeptides can include variants having about 50%, 60%, 70%, 80%, 90%, and 95% sequence identity to the polypeptide of interest.

"Identity," as known in the art, is a relationship between two or more polypeptide sequences, as determined by comparing the sequences. In the art, "identity" also means the degree of sequence relatedness between polypeptide as determined by the match between strings of such sequences. "Identity" can also mean the degree of sequence relatedness of a polypeptide compared to the full-length of a reference polypeptide. "Identity" and "similarity" can be readily calculated by known methods, including, but not limited to, those described in (Computational Molecular Biology, Lesk, A. M., Ed., Oxford University Press, New York, 1988; Biocomputing: Informatics and Genome Projects, Smith, D. W., Ed., Academic Press, New York, 1993; Computer Analysis of Sequence Data, Part I, Griffin, A. M, and Griffin, H G., Eds., Humana Press, New Jersey, 1994; Sequence Analysis in Molecular Biology, von Heinje, G., Academic Press, 1987; and Sequence Analysis Primer, Gribskov, M and Devereux, J., Eds., M Stockton Press, New York, 1991; and Carillo, H., and Lipman, D., SIAM J Applied Math., 48: 1073 (1988).

Preferred methods to determine identity are designed to give the largest match between the sequences tested. Methods to determine identity and similarity are codified in publicly available computer programs. The percent identity between two sequences can be determined by using analysis software (e.g., Sequence Analysis Software Package of the Genetics Computer Group, Madison Wis.) that incorporates the Needelman and Wunsch, (J. Mol. Biol., 48: 443-453, 1970) algorithm (e.g., NBLAST, and XBLAST). The default parameters are used to determine the identity for the polypeptides of the present disclosure.

By way of example, a polypeptide sequence may be identical to the reference sequence, that is be 100% identical, or it may include up to a certain integer number of amino acid alterations as compared to the reference sequence such that the % identity is less than 100%. Such alterations are selected from: at least one amino acid deletion, substitution, including conservative and non-conservative substitution, or insertion, and wherein said alterations may occur at the amino- or carboxy-terminal positions of the reference polypeptide sequence or anywhere between those terminal positions, interspersed either individually among the amino acids in the reference sequence or in one or more contiguous groups within the reference sequence. The number of amino acid alterations for a given % identity is determined by multiplying the total number of amino acids in the reference polypeptide by the numerical percent of the respective percent identity (divided by 100) and then subtracting that product from said total number of amino acids in the reference polypeptide.

As used herein, the term "low stringency" refers to conditions that permit a polynucleotide or polypeptide to bind to another substance with little or no sequence specificity.

As used herein, the term "purified" and like terms relate to the isolation of a molecule or compound in a form that is substantially free (at least 60% free, preferably 75% free, and most preferably 90% free) from other components normally associated with the molecule or compound in a native environment.

As used herein, the term "pharmaceutically acceptable carrier" encompasses any of the standard pharmaceutical carriers, such as a phosphate buffered saline solution, water and emulsions such as an oil/water or water/oil emulsion, and various types of wetting agents.

"Operably linked" refers to a juxtaposition wherein the components are configured so as to perform their usual function. For example, control sequences or promoters operably linked to a coding sequence are capable of effecting the expression of the coding sequence, and an organelle localization sequence operably linked to protein will assist the linked protein to be localized at the specific organelle.

"Localization Signal or Sequence or Domain" or "Targeting Signal or Sequence or Domain" are used interchangeably and refer to a signal that directs a molecule to a specific cell, tissue, organelle, intracellular region or cell state. The signal can be polynucleotide, polypeptide, or carbohydrate moiety or can be an organic or inorganic compound sufficient to direct an attached molecule to a desired location. Exemplary targeting signals include mitochondrial localization signals from the precursor proteins list in U.S. Pat. No. 8,039,587, and cell targeting signals known in the art such as those in Wagner, et al., Adv. Gen., 53:333-354 (2005). It will be appreciated that the entire sequence need not be included, and modifications including truncations of these sequences are within the scope of the disclosure provided the sequences operate to direct a linked molecule to a specific cell type. Targeting signals of the present disclosure can have 80 to 100% sequence identity to the mitochondrial localize signal or cell targeting signal sequences. One class of suitable targeting signals include those that do not interact with the targeted cell in a receptor:ligand mechanism. For example, targeting signals include signals having or conferring a net charge, for example a positive charge. Positively charged signals can be used to target negatively charged cell types such as neurons and muscle. Negatively charged signals can be used to target positively charged cells.

"Cell surface marker" refers to any molecule such as moiety, peptide, protein, carbohydrate, nucleic acid, antibody, antigen, and/or metabolite presented on the surface or in the vicinity of a cell sufficient to identify the cell as unique in either type or state.

II. Mechanisms for Reducing or Preventing Nitrative Damage

It has been established that oxidative and nitrosative damage to biological systems can be prevented by shielding tyrosine residues from nitration. Methods of using nitration shielding to block or reduce oxidative and nitrosative damage to biological systems and treat symptoms of pathologies associated with oxidative stress and protein nitration are disclosed. In some embodiments the nitration shielding agents selectively shield one or more specific proteins from nitrative damage through steric blockade of nitrating agents. Preferably, the peptide binds to the protein of interest to block access of the nitrating agents to one or more tyrosine residues on the protein of interest. In other embodiments the nitration shielding agents provide a molecular sink to saturate the activity of nitrating agents. In further embodiments the nitration shielding agents serve as a substrate for the nitrating agent (i.e., provide an alternative nitratable tyrosine residue). In yet further embodiments the nitration shielding agents provide a nitrating agent neutralizing moiety such as an antioxidant. The disclosed nitration shielding agents can be designed for protection of a single protein of interest, or designed to protect multiple different proteins within one or more biological systems.

In a preferred embodiment the nitration shielding agent is a peptide. Nitration shielding peptides can be engineered using recombinant protein techniques known in the art to provide protection for any protein that is susceptible to nitrative damage.

A. Nitrative Modification

Protein tyrosine nitration is a covalent protein modification resulting from the addition of a nitro ($-NO_2$) group onto one of the two equivalent ortho carbons of the aromatic ring of tyrosine residues. The production of nitrotyrosine residues has commonly been used as a marker of pathological disease processes and of oxidative stress (Ischiropoulos, et al., *Arch. Biochem. Biophys.*, 356:1-11 (1998)). Tyrosine nitration can influence the structure, function and effective concentration of proteins. Factors that determine the level of protein tyrosine nitration include the proximity and level of nitrating agents, the abundance or concentration of the target protein, as well as the amino acid sequence and tertiary structure of the target protein. Tyrosine nitration can occur near acidic residues in regions of a protein that are free from stearic hindrance, such as in solvent-exposed loop regions on the protein surface. Tyrosine residues in favorable environments for nitration in the secondary and tertiary structures of proteins can be more prone to nitration than tyrosine residues at less favorable positions in the same protein. The proximity and relative abundance of other amino acid residues that compete for nitrating agents, such as cysteine, tryptophan and methionine, can also influence the level of nitration of a tyrosine residue within the protein.

Nitrative damage can prevent, reduce or otherwise alter normal protein function, initiating or contributing to a cascade of deleterious events. For example, tyrosine nitration sites located within catalytic domains of enzymes can impact enzyme activity; tyrosine nitration sites located within the antigen recognition domain of immune receptors can prevent, reduce or otherwise alter antigen recognition and immune function; tyrosine nitration can prevent or disrupt receptor:ligand interactions and abrogate normal signaling pathways. Therefore, nitrative damage is implicated in the pathogenesis of multiple diseases and disorders. For example, neurodegenerative tauopathies have been associated with nitration of Tyr 29 of the Tau protein (Reynolds, et al, *The Journal of Neuroscience*, 26(42):10636-10645 (2006)); diabetic cardiomyopathy has been linked with reactive oxygen and nitrogen species (Cai, *Free Radical Biology and Medicine*, 41 (6), 851-861 (2006)); and persistent nitrative stress is associated with cytotoxicity, chronic inflammation and cancer (Roberts, et al., *Toxicol. Sci.*, 112(1):4-16 (2006)).

A non-limiting list of proteins that are nitrated and/or nitrosylated in various diseases includes fibrinogen, plasminogen, surfactant protein A, p130 adhesion protein, p53 tumor suppressor, histones, profilin, insulin receptor substrate-I, glutamine synthetase, iNOS, histone deacetylase II, Tau protein, alpha synuclein, alpha enolase, triosphosphate isomerase, carnitine palmitoyltransferase I, creaine kinase, GAPDH, superoxide dismutases (SOD1/2), glutathione peroxidase (GPX), nicotinamide nucleotide transhydrogenase, cytochrome C, ATP synthases, SERCA2A, amiloride-sensitive Na+ channel, desmin, tubulin, neurofilament L, actin, prostacyclin synthase, ethanol-inducible cytochrome P450 2E1 (CYP2E1), cytosolic and mitochondrial aldehyde dehydrogenases (ALDH1/2; retinal aldehyde dehydrogenases ALDH1A1/2/3; 10-formyltetrahydrofolate dehydrogenase ALDH1L1) and thiolases.

B. Nitration Shielding Agents

Nitration shielding agents are agents that reduce or prevent nitrative damage. Exemplary nitration shielding agents include peptides, small molecules and nucleic acids. Any proteins that are susceptible to nitrative damage can be shielded from nitration by the disclosed nitration shielding agents. The nitration shielding agents can prevent changes to the structure and function of a protein of interest. In preferred embodiments, the protein of interest is a protein whose nitration-state is associated with a disease or disorder.

Prevention of nitrative damage can be accomplished through preventing or reducing the activity of a nitrating agent. In certain embodiments nitration shielding agents prevent nitrating agents from contacting a tyrosine residue that is susceptible to nitration. In some embodiments nitration shielding agents directly inhibit contact through stearic hindrance. The nitration shielding agents can occlude the close contact of a nitrating agent by binding to the protein of interest. In particular embodiments, the nitration shielding agents bind directly to a tyrosine that is susceptible to nitration. Preferably, interaction of the nitration shielding agent with the protein of interest does not affect or reduce the function or structure of protein of interest. In other embodiments nitration shielding agents provide a molecular sink (e.g., one or more tyrosine residues) which saturate the activity of a nitrating agent.

1. Nitration Shielding Peptides

In a preferred embodiment the nitration shielding agent is a peptide. A nitration shielding peptide is a peptide that blocks, inhibits, prevents or otherwise reduces nitration of one or more residues of a protein of interest. The nitration shielding peptide can include a fragment of the full-length protein, or functional variant thereof.

For example, the RhoA nitration shielding peptides provided below are exemplary nitration shielding peptides that include a fragment of full-length RhoA. In some embodiments, the nitration shielding peptide is not a fragment of the full-length protein it targets. The PKG-1α nitration shielding peptides provided below are exemplary nitration shielding peptides that do not include a fragment PKG-1α.

Molecular modeling can be used to predict and prepare peptides that bind to the protein of interest in or around the region of protein nitration. For example, peptides can be optimized geometrically and binding constants calculated using the docking module of Yasara software as exemplified in the working Examples below. Yasara (Yet Another Scientific Artificial Reality Application) refers to structure/homology modeling application (Venselaar, et al., *Eur. Biophys. J.*, 39(4):551-63 (2010)).

In some embodiments, the nitration shielding peptide does not bind the protein of interest. In such embodiments the nitration shielding peptide can serve as a molecular sink binding to or otherwise absorbing the nitration activity of a protein nitrating agent.

As discussed in more detail below, the nitration shielding peptide can be a fusion protein that includes a nitration shielding peptide domain and one or more additional domains including, but not limited to, a protein transduction domain and a cell or organelle targeting domain. The nitration shielding peptide can also include an antioxidant moiety, a charge neutralizing moiety, or a combination thereof.

i. Nitration Shielding Domain

The disclosed nitration shielding peptides include a nitration shielding domain. The nitration shielding domain can be the only domain of the nitration shielding peptide needed to shield a protein of interest from nitration. Therefore, in some embodiments a complete nitration shielding peptide consists of a nitration shielding domain.

The nitration shielding domain can include within its sequence an amino acid residue corresponding to the amino acid residue that can be nitrated in the full-length protein, referred to herein as the "nitrated amino acid" or "nitrated residue". Most typically, the residue is a tyrosine. Therefore, the nitration shielding peptide can include a tyrosine. The nitration shielding domain provides an alternative amino acid residue (most typically a tyrosine) that can react with the nitrating agent. In this way the nitration shielding domain can "shield" the protein of interest from nitration rather than only sterically inhibiting access of the nitrating agent to the protein.

The nitrated residue can be at or near the center of the nitration shielding peptide. Therefore, the nitrated residue can be in the center of the nitration shielding domain or the center of the nitration shielding peptide; or the nitrated residue can be 1, 2, 3, 4, 5, 6, 7, 8, 9, 10, 25, 50, or more residues from the center of the nitration shielding domain or the center of the nitration shield peptide.

The nitration shielding domain blocks or reduces the frequency or efficacy of nitration of the protein of interest compared to a control. The nitration shielding domain can be a fragment of the full-length protein of interest, or a variant thereof. Therefore the nitration shielding domain can have 100% sequence identity with a corresponding fragment of the protein of interest. Alternatively, the nitration shielding domain can have 99, 98, 97, 96, 95, 93, 92, 91, 90, 85, 80, 75, 70 percent or less sequence identity with a corresponding fragment of the protein of interest and blocks or reduces the frequency or efficacy of nitration of the protein of interest compared to a control.

The sequence of the nitration shielding domain can be determined by the sequence of the protein of interest. The sequence typically includes the nitrated residue of the protein of interest, and 1, 2, 3, 4, 5, 6, 7, 8, 9, 10, 11, 12, 13, 14, 15, 16, 17, 18, 19, 20, or more residues adjacent to the nitrated residue.

The amino acid residues in the nitration shielding domain can be naturally occurring or non-naturally occurring amino acid residues. Naturally occurring amino acids can include amino acid residues encoded by the standard genetic code as well as non-standard amino acids (e.g., amino acids having the D-configuration instead of the L-configuration), as well as those amino acids that can be formed by modifications of standard amino acids (e.g. pyrrolysine or selenocysteine and ornithine). Non-naturally occurring amino acids are not found or have not been found in nature, but can be incorporated into a peptide chain. Suitable non-naturally occurring amino acids include, but are not limited to, D-alloisoleucine(2R,3S)-2-amino-3-methylpentanoic acid, L-cyclopentyl glycine (S)-2-amino-2-cyclopentyl acetic acid. Other examples of non-naturally occurring amino acids can be found in textbooks or on the worldwide web (e.g., a site is maintained by the California Institute of Technology which displays structures of non-natural amino acids that have been successfully incorporated into functional proteins). Non-natural amino acid residues and amino acid derivatives are also described in U.S. Patent Application Publication No. 2004/0204561 by Ellison.

Another class of materials that can be used in the production of the nitration shielding domain is peptidomimetics. Peptidomimetics, as used herein, refers to molecules, which mimic peptide structure. Peptidomimetics have general features analogous to their parent structures, polypeptides, such as amphiphilicity. Examples of such peptidomimetic materials are described in Moore, et al., *Chem. Rev.* 101(12), 3893-4012 (2001).

The peptidomimetic materials can be classified into four categories: α-peptides, β-peptides, γ-peptides, and δ-peptides. Copolymers of these peptides can also be used. Examples of α-peptide peptidomimetics include, but are not limited to, N,N'-linked oligoureas, oligopyrrolinones, oxazolidin-2-ones, azatides and azapeptides. Examples of β-peptides include, but are not limited to, β-peptide foldamers, β-aminoxy acids, sulfur-containing β-peptide analogues, and hydrazino peptides. Examples of γ-peptides include, but are not limited to, γ-peptide foldamers, oligoureas, oligocarbamates, and phosphodiesters. Examples of δ-peptides include, but are not limited to, alkene-based δ-amino acids and carbopeptoids, such as pyranose-based carbopeptoids and furanose-based carbopeptoids.

The sequence of the nitration shielding domain can also account for or include other structural or functional features of the protein of interest. The nitration shielding domain can be designed to bind directly or indirectly to the protein of interest. For example, the shielding domains of the exemplary RhoA-binding nitration shielding peptides discussed below were designed to bind to predicted multimeric interface of RhoA.

In some embodiments the nitration shielding domain is not a fragment of the full-length target protein and shares little or no identity with the primary sequence of target protein. The nitration shielding peptide can have little or no primary sequence identity with the target protein, but nonetheless bind to a region of the target protein and blocks nitration. As discussed in more detail below, an exemplary PKG-Iα nitration blocking peptide has little or no primary sequence identity with the PKG-Iα, but is believed to bind to a region of PKG-Iα surrounding the nitratable residue Y247 of PKG-Iα. The binding can be dictated by secondary, tertiary, or quaternary structure of the protein of interest, other protein-protein interactions, or combination thereof.

The nitration shielding domain can be between about 5 and 100 amino acids inclusive in length. Therefore, the nitration shielding domain can have any integer of amino acids between 5 and 100. In some embodiments, the nitration shielding domain has 7 to 15 amino acids, 8 to 14 amino acids, 9 to 13 amino acids, 10 to 12 amino acids, or 11 amino acids. In a preferred embodiment, the nitration shielding domain is about 11 amino acids. A tyrosine corresponding to the nitrated residue of the protein of interest can be in the center.

ii. Protein Transduction Domain

The nitration shielding peptides and compositions including nitration shielding peptides can be modified to include a protein transduction domain. As used herein, a "protein transduction domain" or PTD refers to a polypeptide, polynucleotide, carbohydrate, organic or inorganic compound that facilitates traversing a lipid bilayer, micelle, cell membrane, organelle membrane, or vesicle membrane. A PTD attached to another molecule facilitates the molecule traversing membranes, for example going from extracellular space to intracellular space, or cytosol to within an organelle.

A protein transduction domain can be added to the N-terminus or C-terminus of the nitration shielding domain, or any other domain or moiety of a nitration shielding fusion protein thereof, provided that the domain enhance intracellular delivery of the peptide and does not prevent its nitration blocking ability.

In preferred embodiments, the protein transduction domain is a polypeptide. A protein transduction domain can be a polypeptide including positively charged amino acids. Thus, some embodiments include PTDs that are cationic or amphipathic. Protein transduction domains (PTD), also known as a cell penetrating peptides (CPP), are typically polypeptides including positively charged amino acids. PTDs are known in the art, and include but are not limited to small regions of proteins that are able to cross a cell membrane in a receptor-independent mechanism (Kabouridis, P., *Trends in Biotechnology* (11):498-503 (2003)). Although several PTDs have been documented, the two most commonly employed PTDs are derived from TAT (Frankel and Pabo, *Cell,* 55(6):1189-93 (1988)) protein of HIV and Antennapedia transcription factor from *Drosophila*, whose PTD is known as Penetratin (Derossi, et al., *J. Biol. Chem.,* 269(14):10444-50 (1994)). Exemplary protein transduction domains include polypeptides with 11 Arginine residues, or positively charged polypeptides or polynucleotides having 8-15 residues, preferably 9-11 residues. The Antennapedia homeodomain is 68 amino acid residues long and contains four alpha helices. Penetratin is an active domain of this protein which consists of a 16 amino acid sequence derived from the third helix of Antennapedia. TAT protein consists of 86 amino acids and is involved in the replication of HIV-1. The TAT PTD consists of an 11 amino acid sequence domain (residues 47 to 57; YGRKKRRQRR R (SEQ ID NO:1)) of the parent protein that appears to be critical for uptake. Additionally, the basic domain Tat(49-57) or RKKRRQRRR (SEQ ID NO:2) has been shown to be a PTD. Another TAT sequence includes an N-terminal histidine: HRKKRRQRRR (SEQ ID NO:3). In the current literature TAT has been favored for fusion to proteins of interest for cellular import. Several modifications to TAT, including substitutions of Glutatmine to Alanine, i.e., Q→A, have demonstrated an increase in cellular uptake anywhere from 90% (Wender, et al., *Proc. Natl. Acad. Sci. USA.,* 97(24):13003-8 (2000)) to up to 33 fold in mammalian cells (Ho, et al., *Cancer Res.,* 61(2):474-7 (2001)). The most efficient uptake of modified proteins was revealed by mutagenesis experiments of TAT-PTD, showing that an 11 arginine stretch was several orders of magnitude more efficient as an intercellular delivery vehicle. Therefore, PTDs can include a sequence of multiple arginine residues, referred to herein as poly-arginine or poly-ARG. In some embodiments the sequence of arginine residues is consecutive. In some embodiments the sequence of arginine residues is non-consecutive. A poly-ARG can include at least 7 arginine residues, more preferably at least 8 arginine residues, most preferably at least 11 arginine residues. In some embodiments, the poly-ARG includes between 7 and 15 arginine residues, more preferably between 8 and 15 arginine residues. In some embodiments the poly-ARG includes between 7 and 15, more preferably between 8 and 15 consecutive arginine residues. An example of a poly-ARG is RRRRRRR (SEQ ID NO:4). Additional exemplary PTDs include but are not limited to;

```
                                        (SEQ ID NO: 5)
RRQRRTSKLM KR;

(SEQ ID NO: 6)
GWTLNSAGYL LGKINLKALA ALAKKIL;

(SEQ ID NO: 7)
WEAKLAKALA KALAKHLAKA LAKALKCEA;
and (SEQ ID NO: 8)
RQIKIWFQNR RMKWKK.
```

Without being bound by theory, it is believed that following an initial ionic cell-surface interaction, some polypeptides containing a protein transduction domain are rapidly internalized by cells via lipid raft-dependent macropinocytosis. For example, transduction of a TAT-fusion protein was found to be independent of interleukin-2 receptor/raft-, caveolar- and clathrin-mediated endocytosis and phagocytosis (Wadia, et al., *Nature Medicine,* 10:310-315 (2004), and Barka, et al., *J Histochem. Cytochem.,* 48(11):1453-60 (2000)). Therefore, in some embodiments the polynucleotide-binding polypeptide includes an endosomal escape sequence that enhances escape of the polypeptide-binding protein from macropinosomes. The some embodiments the endosomal escape sequence is part of, or consecutive with, the protein transduction domain. In some embodiments, the endosomal escape sequence is non-consecutive with the protein transduction domain. In some embodiments the endosomal escape sequence includes a portion of the hemagglutinin peptide from influenza (HA). One example of an endosomal escape sequence includes

```
                                        (SEQ ID NO: 9)
GDIMGEWG NEIFGAIAGF LG.
```

In one embodiment a protein transduction domain including an endosomal escape sequence includes the amino acid sequence

```
                                        (SEQ ID NO: 10)
RRRRRRRRR RGEGDIMGEW GNEIFGAIAG FLGGE
``` iii. Targeting Signal or Domain

The nitration shielding peptides and compositions including nitration shielding peptides can be modified to include one or more targeting signals or domains. The targeting signal can include a sequence of monomers that facilitates in vivo localization of the molecule. The monomers can be amino acids, nucleotide or nucleoside bases, or sugar groups such as glucose, galactose, and the like which form carbohydrate targeting signals. Targeting signals or sequences can be specific for a host, tissue, organ, cell, organelle, non-nuclear organelle, or cellular compartment. For example, in some embodiments the polynucleotide-binding polypeptide includes both a cell-specific targeting domain and an organelle specific targeting domain to enhance delivery of the polypeptide to a subcellular organelle of a specific cells type.

A targeting signal domain can be added to the N-terminus or C-terminus of the nitration shielding domain, or any other domain or moiety of a nitration shielding fusion protein thereof, provided that the domain increases cell or organelle targeting of the peptide and does not prevent its nitration blocking ability.

a. Cell Targeting

The nitration shielding peptides or compositions including nitration shielding peptides can be modified to target a specific cell type or population of cells.

In one embodiment, the targeting signal binds to its ligand or receptor which is located on the surface of a target cell such as to bring the nitration shielding peptide and cell membranes sufficiently close to each other to allow penetration of the nitration shielding peptide into the cell.

In a preferred embodiment, the targeting molecule is selected from the group consisting of an antibody or antigen binding fragment thereof, an antibody domain, an antigen, a T-cell receptor, an RNA aptamer, a cell surface receptor, a cell surface adhesion molecule, a major histocompatibility locus protein, a viral envelope protein and a peptide selected by phage display that binds specifically to a defined cell.

Targeting a nitration shielding peptide or composition thereof to specific cells can be accomplished by modifying the polypeptide of interest to express specific cell and tissue targeting signals. These sequences target specific cells and tissues. In some embodiments the interaction of the targeting signal with the cell does not occur through a traditional receptor:ligand interaction. The eukaryotic cell includes a number of distinct cell surface molecules. The structure and function of each molecule can be specific to the origin, expression, character and structure of the cell. Determining the unique cell surface complement of molecules of a specific cell type can be determined using techniques well known in the art.

One skilled in the art will appreciate that the tropism of the disclosed nitration shielding peptides or compositions thereof can be altered by changing the targeting signal. In one specific embodiment, nitration shielding peptides and compositions thereof are provided that enable the addition of cell surface antigen specific antibodies to the peptide or a composition thereof for targeting the delivery of the polypeptide. Exemplary cell surface antigens are disclosed in Wagner et al., *Adv. Gen.*, 53:333-354 (2005) which is specifically incorporated by reference herein in its entirety.

It is known in the art that nearly every cell type in a tissue in a mammalian organism possesses some unique cell surface receptor or antigen. Thus, it is possible to incorporate nearly any ligand for the cell surface receptor or antigen as a targeting signal. For example, peptidyl hormones can be used a targeting moieties to target delivery to those cells which possess receptors for such hormones. Chemokines and cytokines can similarly be employed as targeting signals to target delivery of the complex to their target cells. A variety of technologies have been developed to identify genes that are preferentially expressed in certain cells or cell states and one of skill in the art can employ such technology to identify targeting signals which are preferentially or uniquely expressed on the target tissue of interest.

The nitration shielding peptides or compositions thereof can be modified with galactosyl-terminating macromolecules to target the shielding peptide to the liver or to liver cells. The modified nitration shielding peptides or compositions thereof selectively enters hepatocytes after interaction of the carrier galactose residues with the asialoglycoprotein receptor present in large amounts and high affinity only on these cells.

i. Targeting Lung Cells

The peptides or compositions thereof can be targeted to lung cells. As discussed in more detail below, protein nitration in the lungs can be associated with pathologies and disease conditions. For example, nitration of RhoA leads to increased endothelial hyperpermeability and can lead disorders such as acute lung injury, acute respiratory distress, and ventilator-induced/associated lung injury, among others. Furthermore, nitration of PKG-1α in the lungs is associated with acute and chronic pulmonary hypertension. Therefore, in some embodiments, in is desirable to direct delivery of the nitration shielding peptide or a combination thereof to lung cells. Pulmonary tissue includes a variety of cell types including epithelial cells, connective tissue, endothelial cells, nerve cells, muscle cells and other supporting cells. Therefore, in some embodiments, the shielding peptides or combinations thereof are targeted to lung epithelial cells, connective tissue, endothelial cells, nerve cells, muscle cells, or a combination thereof. In a preferred embodiment, the shielding peptides or combinations there are directed of lung endothelial cells, lung vascular smooth muscle cells, or a combination thereof.

A number of vascular receptors and ligands have been identified that can be used to target the shielding peptides or compositions thereof to various lung cells types. See, for example, Table 1, adapted from Giordano, et al., *Proceedings of the American Thoracic Society*, 6(5):411-415 (2009).

TABLE 1

List of Selected Molecular Ligands Expressed in Lung Vasculature

| Lung Vascular Receptor | Ligand | Localization |
|---|---|---|
| | | Cell Culture Studies |
| α-galactose and α-N-actyl-galactosamine | *Griffonia simplicifolia* lectin | Microvascular endothelial cells |
| α and β-N-actyl-galactosamine | *Helix pomatia* lectin | Pulmonary artery derived endothelial cells |
| E-cadherin | N.D. | Microvascular endothelial cells (not expressed by artery endothelial cells) Phage Display |
| Membrane dipeptidyl peptidase (CD26) | GFE peptide | Lung endothelial cells |
| Receptor unknown | CGSPGWVRC peptide | Lung endothelial cells |

TABLE 1-continued

List of Selected Molecular Ligands Expressed in Lung Vasculature

| Lung Vascular Receptor | Ligand | Localization |
|---|---|---|
| | | cDNA Array |
| Phospholipase A2 group XII | N.D. | Lung endothelial cells |
| Secreted frizzled related protein 1 (sFRP1) | N.D. | Lung endothelial cells |
| Osteoglycin | N.D. | Lung endothelial cell, smooth muscle cell, around cartilage and alveoli |
| | | Other Approaches |
| Ca2+-activated chloride channels (human CLCA-2/mouse CLCA-1/Lu-ECAM-1) | α6β4 integrin | Endothelia of the aorta and pulmonary venules |
| Dipeptidyl peptidase IV (CD26) | Fibronectin | Lung endothelium |
| Angiotensin converting enzyme (ACE) (lung selective marker) | Antibody anti-angiotensin converting enzyme | Endothelial luminal surface |
| Platelet-endothelial adhesion molecule-1 (PECAM-1)/CD31 (lung selective marker) | Antibody anti-platelet-endothelial adhesion molecule-1 | Intercellular borders of the endothelial monolayer |
| Aminopeptidase P (APP) | antibody anti-aminopeptidase P | Caveola of lung endothelium |

For example, the nitration shielding peptide or a combination thereof can be modified to include any ligand that binds to any of the "lung vascular receptors" of Table 1. Exemplary ligands are listed in Table 1 under the column labeled "ligand".

In a preferred embodiment, the peptide or a composition thereof is modified to include the targeting signal CGFECVRQCPERC (SEQ ID NO:11) (termed GFE-1), or a functional variant thereof (Rojotte and Ruoslahti, *J. Biol. Chem.*, 23; 274(17):11593-8 (1999)). GFE-1 binds to membrane dipeptidase (MDP), a lung cell-surface zinc metalloprotease involved in the metabolism of glutathione, leukotriene D4, and certain beta-lactam antibiotic. According, this peptide can be used to increase targeting of the nitration shielding peptide or composition thereof to lung endothelium.

ii. Antibodies

Another embodiment provides an antibody or antigen binding fragment thereof bound to the disclosed nitration shielding peptides or compositions thereof acting as the targeting signal. The antibodies or antigen binding fragment thereof are useful for directing the vector to a cell type or cell state. In one embodiment, the polypeptide of interest possesses an antibody binding domain, for example from proteins known to bind antibodies such as Protein A and Protein G from *Staphylococcus aureus*. For example, some embodiments include the amino acids sequence

```
                                      (SEQ ID NO: 12)
HDEAQQNAFY QVLNMPNLNA DQRNGFIQSL KDDPSQSANV
LGEAHDEAQQ NAFYQVLNMP NLNADQRNGF IQSLKDDPSQ
SANVLGEA
or
                                      (SEQ ID NO: 13)
HDEAQQNAFY QVLNMPNLNA DQRNGFIQSL KDDPSQSANV
LGEAHDEAQQ NAFYQVLNMP NLNADQRNGF IQSLKDDPSQ
SANVLGEAGE G,
``` both of which include the tandem domain B of Protein A.

Other domains known to bind antibodies are known in the art and can be substituted. In certain embodiments, the antibody is polyclonal, monoclonal, linear, humanized, chimeric or a fragment thereof. Representative antibody fragments are those fragments that bind the antibody binding portion of the non-viral vector and include Fab, Fab', F(ab'), Fv diabodies, linear antibodies, single chain antibodies and bispecific antibodies known in the art. In some embodiments, the targeting domain includes all or part of an antibody that directs the nitration shielding peptides or compositions thereof to the desired target cell type or cell state. Antibodies can be monoclonal or polyclonal, but are preferably monoclonal. Antibodies can be derived from human genes, specific for cell surface markers, and produced to reduce potential immunogenicity to a human host as is known in the art. For example, transgenic mice which contain the entire human immunoglobulin gene cluster are capable of producing "human" antibodies can be utilized. In one embodiment, fragments of such human antibodies are employed as targeting signals. In a preferred embodiment, single chain antibodies modeled on human antibodies are prepared in prokaryotic culture.

b. Organelle Targeting

The nitration shielding peptides or compositions thereof can additionally or alternatively be modified to target a subcellular organelle. Targeting of the disclosed polypeptides to organelles can be accomplished by modifying the disclosed nitration shielding peptides or compositions thereof to contain specific organelle targeting signals. These sequences can target organelles, either specifically or non-specifically. In some embodiments the interaction of the targeting signal with the organelle does not occur through a traditional receptor:ligand interaction.

The eukaryotic cell includes a number of discrete membrane bound compartments, or organelles. The structure and function of each organelle is largely determined by its unique complement of constituent polypeptides. However, the vast majority of these polypeptides begin their synthesis in the cytoplasm. Thus organelle biogenesis and upkeep require that newly synthesized proteins can be accurately targeted to their appropriate compartment. This is often accomplished by amino-terminal signaling sequences, as well as post-translational modifications and secondary structure.

Organelles can have single or multiple membranes and exist in both plant and animal cells. Depending on the function of the organelle, the organelle can consist of specific components such as proteins and cofactors. The polypeptides delivered to the organelle can enhance or contribute to the functioning of the organelle. Some organelles, such as mitochondria and chloroplasts, contain their own genome. Nucleic acids are replicated, transcribed, and translated within these organelles. Proteins are imported and metabolites are exported. Thus, there is an exchange of material across the membranes of organelles. Exemplary organelles include the nucleus, mitochondrion, chloroplast, lysosome, peroxisome, Golgi, endoplasmic reticulum, and nucleolus. Synthetic organelles can be formed from lipids and can contain specific proteins within the lipid membranes. Additionally, the content of synthetic organelles can be manipulated to contain components for the translation of nucleic acids.

iv. Antioxidant

Peroxynitrite-dependent nitrations can be reduced or impaired by antioxidants and thioreductants (Guermonprez, et al., *Molecular Pharmacology*, 60(4):838-846 (2001)). The nitration shielding peptide or a composition thereof can include or be conjugated to, or be administered in combination with one or more antioxidants, thioreductants, or a combination thereof. In a preferred embodiment, an antioxidant moiety such as nitroxide is conjugated to the nitration shielding peptide.

The antioxidant, thioreductant, or combination thereof can be added to the N-terminus or C-terminus of the nitration shielding domain, or any other domain or moiety of a nitration shielding fusion protein thereof.

Exemplary antioxidants include, but are not limited to uric acid, melatonin, bovine serum albumin, and desferrioxamine. Antioxidants that are particular useful for conjugating directly to the nitration shielding peptides or compositions thereof include, but are not limited to, nitroxide compounds, biopterin (2-N-Acetyl-1',2'-di-O-acetyl-6-biopterin), quinone (9,10-Dihydro-4,5-dihydroxy-9,10-dioxo-2-anthracenecarboxylic acid) and porphyrin (MnTMPyp).

Cyclic nitroxides, also known as aminoxyls or nitroxyls, are stable free radicals stabilized by methyl groups at the $\alpha$ position in five-membered pyrrolidine, pyrroline or oxazolidine and six-membered piperidine ring structures (Soule, et al., *Free Radic. Biol. Med.,* 42(11): 1632-1650 (2007)). Methyl groups confer stability to the nitroxide radicals by preventing radical-radical dismutation and also limit access to reactive substances, which can quench the radical species. Substituent groups on the ring produce a diverse range of compounds that can be directed to specific hydrophilic or hydrophobic regions in the cellular microenvironment. An exemplary nitroxide is 3-carboxy-2,2,5,5-tetramethyl-3-pyrrolin-1-yloxy.

Exemplary thioreductants include, but are not limited to, glutathione, N-acetyl cysteine, and dithiothreitol (DTT). Although dithiothreitol (DTT) is known to prevent or even reverse several deleterious effects of radiation or of chemical agents operating via free radical and oxidative stress, its use has been hampered by its chemical instability and toxic properties. To address these issues, modified DTT, such as dithiothreitol tetraacetate (DTT-Ac), have been developed which are less toxic and chemically stable (de Mecca, et al., *Arch Toxicol,* 67(8):547-51 (1993)).

In some embodiments, the peptide or composition thereof includes a moiety that neutralizes the charge associated with antioxidant or thioreductant. For example, in some embodiments, an amide is added to the peptide, or a composition thereof to reduce a negative charge associated with an antioxidant such as 3-carboxy-2,2,5,5-tetramethyl-3-pyrrolin-1-yloxy.

v. Additional Sequences

The fusion protein can optionally include additional sequences or moieties, including, but not limited to linkers and purification tags. The additional sequences or moieties can be added to the N-terminus or C-terminus of the nitration shielding domain, or any other domain or moiety of a nitration shielding fusion protein thereof.

In a preferred embodiment the purification tag is a polypeptide. Polypeptide purification tags are known in the art and include, but are not limited to His tags which typically include six or more, typically consecutive, histidine residues; FLAG tags, which typically include the sequence DYKDDDDK (SEQ ID NO:14); haemagglutinin (HA) for example, YPYDVP (SEQ ID NO:15); MYC tag for example ILKKATAYIL (SEQ ID NO:16) or EQKLISEEDL (SEQ ID NO:17). Methods of using purification tags to facilitate protein purification are known in the art and include, for example, a chromatography step wherein the tag reversibly binds to a chromatography resin.

Purifications tags can be N-terminal or C-terminal to the fusion protein. The purification tags N-terminal to the fusion protein are typically separated from the polypeptide of interest at the time of the cleavage in vivo. Therefore, purification tags N-terminal to the fusion protein can be used to remove the fusion protein from a cellular lysate following expression and extraction of the expression or solubility enhancing amino acid sequence, but cannot be used to remove the polypeptide of interest. Purification tags C-terminal to the fusion protein can be used to remove the polypeptide of interest from a cellular lysate following expression of the fusion protein, but cannot be used to remove the expression or solubility enhancing amino acid sequence. Purification tags that are C-terminal to the expression or solubility enhancing amino acid sequence can be N-terminal to, C-terminal to, or incorporated within the sequence of the polypeptide of interest.

In some embodiments, to fusion protein includes one or more linkers or spacers. In some embodiments linker or spacer is one or more polypeptides. In some embodiments, the linker includes a glycine-glutamic acid di-amino acid sequence. The linkers can be used to link or connect two domains, regions, or sequences of the fusion protein.

2. Exemplary Nitration Shielding Peptides

Exemplary nitration shielding peptides are provided.

a. RhoA

In some embodiments, the nitration shielding peptide is a peptide that blocks or otherwise reduces tyrosine nitration of RhoA. Full-length sequences for RhoA are known in the art. See, for example, UniProt Accession Number P61586 (RHOA_HUMAN), which provides the amino acid sequence,

```
                                       (SEQ ID NO: 19)
MAAIRKKLVI VGDGACGKTC LLIVFSKDQF PEVYVPTVFE
NYVADIEVDG KQVELALWDT AGQEDYDRLR PLSYPDTDVI
LMCFSIDSPD SLENIPEKWT PEVKHFCPNV PIILVGNKKD
LRNDEHTRRE LAKMKQEPVK PEEGRDMANR IGAFGYMECS
AKTKDGVREV FEMATRAALQ ARRGKKKSGC LVL.
```

It has been discovered that the small GTPase, RhoA has a single nitration site located at tyrosine 34 (Y34). Y34 is located within the switch I region adjacent to the protein's nucleotide-binding site. Nitration of this site is associated with endothelial barrier dysfunction including, but not limited to, endothelial hyperpermeability and has been connected to various disorders and pathologies including, but not limited to, acute lung injury. Molecular dynamic (MD) simulations and stopped-flow kinetic analysis indicate that the mechanism by which Y34 nitration stimulates RhoA activity is through a decrease in GDP binding to the protein due to a conformational change within a region of Switch I, mimicking the conformational shift observed when RhoA is bound to a guanine nucleotide exchange factor (GEF).

Therefore, the nitration shielding peptide can block or otherwise reduce nitration of the first tyrosine in RhoA. In a particular embodiment, the nitration shielding peptide blocks or otherwise reduces nitration of tyrosine 34 (Y34) of a RhoA. For example, the nitration shielding peptide can block nitration of Y34 numbering from the initiation methionine of SEQ ID NO:19, or a corresponding tyrosine in a homolog or variant thereof.

An exemplary RhoA nitration shielding domain of a peptide for shielding nitration of Y34 of RhoA includes the amino acid sequence QFPEVYVPTVF (SEQ ID NO:20), or a variant thereof with 70, 75, 80, 85, 90, 95, 98, 99 percent or greater sequence identity to the SEQ ID NO:20. SEQ ID NO:20 corresponds with amino acids 29-39 of SEQ ID NO:19. Specific variants of SEQ ID NO:20 include FPEVYVPTVF (SEQ ID NO:21), QFPVYVPTVF (SEQ ID NO:22), and FPVYVPTVF (SEQ ID NO:23).

Typically, the RhoA nitration shielding peptide includes the target amino acid residue for which nitration will be blocked or reduced, but does not consist of full length RhoA. Typically the nitration shielding peptide includes a fragment of full length RhoA. For example a RhoA nitration shielding domain can between 5 and 100 amino acids inclusive. For example, the nitration shielding domain can be 8, 9, 10, 11, 12, 13, 14, or 15 amino acids in length. Therefore, the nitration shielding domain can include a fragment of SEQ ID NO:19 that is any integer between 5 and 100 amino acids inclusive in length and includes Y34 with reference to SEQ ID NO:19; or any variant thereof with 70, 75, 80, 85, 90, 95, 98, 99 percent or greater sequence identity to the corresponding sequence in SEQ ID NO:19.

In some embodiments, a RhoA nitration shielding peptide that reduces or blocks nitration of RhoA consists of a RhoA nitration shielding domain such as one of the RhoA nitration shielding domains discussed above.

The RhoA nitration shielding peptide can be a fusion protein that includes a RhoA nitration shielding domain discussed above. For example, in some embodiments, the RhoA nitration shielding peptide includes a protein transduction domain, a targeting signal, or a combination thereof. In some embodiments, the RhoA nitration shielding peptide includes an HIV TAT protein transduction domain. An exemplary RhoA nitration shielding peptide including an HIV TAT protein transduction domain can include the sequence of SEQ ID NO:20, SEQ ID NO:21, SEQ ID NO:22, or SEQ ID NO:23; or a variant thereof with 70, 75, 80, 85, 90, 95, 98, 99 percent or greater sequence identity to the SEQ ID NO:20, SEQ ID NO:21, SEQ ID NO:22, or SEQ ID NO:23 respectively. For example, in some embodiments, the RhoA nitration shielding peptide includes a nitration shielding domain that can be 8, 9, 10, 11, 12, 13, 14, or 15 amino acids in length, a protein transduction domain, a targeting signal, or a combination thereof.

For example, the RhoA nitration shielding peptide including an HIV TAT protein transduction domain can include the sequence HRKKRRQRRRQFPEVYVPTVF (SEQ ID NO:24), HRKKRRQRRRQFPVYVPTVF (SEQ ID NO:25), or a variant thereof with 70, 75, 80, 85, 90, 95, 98, 99 percent or greater sequence identity to the SEQ ID NO:24 or SEQ ID NO:25.

In some embodiments, the RhoA nitration shielding peptide is HRKKRRQRRRNFPEVYVPTVF (SEQ ID NO:36), or HRKKRRQRRRNFPVYVPTVF (SEQ ID NO:37), where "N" can be any amino acid.

The RhoA nitration shielding peptide can include an antioxidant such a nitroxide, for example 3-carboxy-2,2,5, 5-tetramethyl-3-pyrrolin-1-yloxy. The RhoA nitration shielding peptide can include an amide to reduce negative charge of the peptide, or increase positive charge of the peptide. For example, any of SEQ ID NOS: 20-25, or variants thereof can have an antioxidant moiety conjugated to the N-terminus or the C-terminus. In some embodiments, the antioxidant moiety is 3-carboxy-2,2,5,5-tetramethyl-3-pyrrolin-1-yloxy (nitroxide). In some embodiments, an amide to added to neutralize charge. Preferably the amide as added adjacent to or conjugated directly to the antioxidant. For example, any of SEQ ID NOS: 20-25, or variants thereof without or without an antioxidant can have an amide moiety added.

b. PKG-1α

In some embodiments, the nitration shielding peptide is a peptide that blocks or otherwise reduces tyrosine nitration of PKG-1α. Full-length sequences for PKG-1α are known in the art. See, for example, UniProt Accession Number Q13976 (KGP1_HUMAN), which provides the amino acid sequence,

```
                                              (SEQ ID NO: 26)
MSELEFDFAK ILMLKEERIK ELEKRLSEKE EEIQELKRKL
HKCQSVLPVP STHIGPRTTR AQGISAEPQT YRSFHDLRQA
FRKFTKSERS KDLIKEAILD NDFMKNLELS QIQEIVDCMY
PVEYGKDSCI IKEGDVGSLV YVMEDGKVEV TKEGVKLCTM
GPGKVFGELA ILYNCTRTAT VKTLVNVKLW AIDRQCFQTI
MMRTGLIKHT EYMEFLKSVP TFQSLPEEIL SKLADVLEET
HYENGEYIIR QGARGDTFFI ISKGTVNVTR EDSPSEDPVF
LRTLGKGDWF GEKALQGEDV RTANVIAAEA VTCLVIDRDS
FKHLIGGLDD VSNKAYEDAE AKAKYEAEAA FFANLKLSDF
NIIDTLGVGG FGRVELVQLK SEESKTFAMK ILKKRHIVDT
RQQEHIRSEK QIMQGAHSDF IVRLYRTFKD SKYLYMLMEA
CLGGELWTIL RDRGSFEDST TRFYTACVVE AFAYLHSKGI
IYRDLKPENL ILDHRGYAKL VDFGFAKKIG FGKKTWTFCG
TPEYVAPEII LNKGHDISAD YWSLGILMYE LLTGSPPFSG
PDPMKTYNII LRGIDMIEFP KKIAKNAANL IKKLORDNPS
ERLGNLKNGV KDIQKHKWEE GFNWEGLRKG TLTPPIIPSV
ASPTDTSNFD SFPEDNDEPP PDDNSGWDID F.
```

The 3',5' cyclic guanosine monophosphate (cGMP) dependent protein kinase G-1α (PKG-1α) is a downstream mediator of nitric oxide and natriuretic peptide signaling. Tyrosine nitration attenuates PKG-1α catalytic activity and can contribute to pathogenesis and progression of vascular diseases associated with increased vascular tone and thickness, such as pulmonary hypertension (PH). It has been discovered that PKG-1α is susceptible to nitration at tyrosine 247 and 425. In particular, nitration of tyrosine 247 appears to alter the activity of the protein and associated with disease pathologies.

Therefore, the nitration shielding peptide can block or otherwise reduce nitration of a tyrosine in PKG-1α. In a particular embodiment, the nitration shielding peptide blocks or otherwise reduces nitration of tyrosine 247 (Y247), 425 (Y425), or a combination thereof of a PKG-1α. For example, the nitration shielding peptide can block nitration of Y247, Y425, or a combination thereof numbering from the initiation methionine of SEQ ID NO:26, or a corresponding tyrosine in a homolog or variant thereof. Preferably, the nitration shielding peptide blocks or otherwise reduces nitration of tyrosine 247 (Y247).

An exemplary PKG-1α nitration shielding domain of a peptide for shielding nitration of Y247 of PKG-1α includes the amino acid sequence GALRQKNVK (SEQ ID NO:27), or a variant thereof with 70, 75, 80, 85, 90, 95, 98, 99 percent or greater sequence identity to the SEQ ID NO:27.

As introduced above, this PKG-1α nitration blocking peptide has little or no linear sequence identity with: the PKG-1α, but is believed to bind to a region of PKG-1α surrounding the nitratable residue Y247 of PKG-1α.

The PKG-1α nitration shielding peptide can be a fusion protein that includes a PKG-1α nitration shielding domain discussed above. For example, in some embodiments, the PKG-1α nitration shielding peptide includes a protein transduction domain, a targeting signal, or a combination thereof. In some embodiments, the PKG-1α nitration shielding peptide includes an HIV TAT protein transduction domain. An exemplary PKG-1α nitration shielding peptide including an HIV TAT protein transduction domain can include the sequence of SEQ ID NO:27 or a variant thereof with 70, 75, 80, 85, 90, 95, 98, 99 percent or greater sequence identity to SEQ ID NO:27.

For example, the PKG-1α nitration shielding peptide including an HIV TAT protein transduction domain can include the sequence HRKKRRQRRRGALRQKNVK (SEQ ID NO:28), HRKKRRQRRRNGALRQKNVK (SEQ ID NO:38) where "N" is any amino acid, for example, a glutamine, or a variant thereof with 70, 75, 80, 85, 90, 95, 98, 99 percent or greater sequence identity to the SEQ ID NO:28, or SEQ ID NO:38.

The PKG-1α nitration shielding peptide can include an antioxidant such a nitroxide, for example 3-carboxy-2,2,5,5-tetramethyl-3-pyrrolin-1-yloxy. The PKG-1α nitration shielding peptide can include an amide to reduce negative charge of the peptide, or increase positive charge of the peptide. For example, any of SEQ ID NOS:27-28, or variants thereof can have an antioxidant moiety conjugated to the N-terminus or the C-terminus. In some embodiments, the antioxidant moiety is 3-carboxy-2,2,5,5-tetramethyl-3-pyrrolin-1-yloxy (nitroxide). In some embodiments, an amide to added to neutralize charge. Preferably the amide as added adjacent to or conjugated directly to the antioxidant. For example, any of SEQ ID NOS: 27-28, or variants thereof without or without an antioxidant can have an amide moiety added.

The PKG-1α nitration shielding peptide can include an antioxidant such a nitroxide, for example 3-carboxy-2,2,5,5-tetramethyl-3-pyrrolin-1-yloxy. The PKG-1α nitration shielding peptide can include an amide to reduce negative charge of the peptide, or increase positive charge of the peptide. The PKG-1α nitration shielding peptide can be from 5 to 100 amino acids in length. For example, the PKG-1α nitration shielding peptide can be 8, 9, 10, or 11 amino acids in length, or the PKG-1α nitration shielding peptide can be 18, 19, 20, or 21 amino acids in length. In a particular embodiment, the nitration shielding peptide includes the amino acid sequence GALRQKNVK(X)-amide (SEQ ID NO:29), HRKKRRQRRRGALRQKNVK(X)-amide (SEQ ID NO:30) HRKKRRQRRRNGALRQKNVK(X)-amide (SEQ ID NO:39) wherein "N" is any amino acid and where "X" is 3-carboxy-2,2,5,5-tetramethyl-3-pyrrolin-1-yloxy (nitroxide), or a variant thereof with 70, 75, 80, 85, 90, 95, 98, 99 percent or greater sequence identity to the SEQ ID NO:29, SEQ ID NO:30, or SEQ ID NO:39. As discussed in more detail below, nitration of PKG-1α is believed to occur at Y247 and Y425. Therefore, in some embodiments, the nitration shielding peptide includes a sequence or subsequence, or binds to the domain that contains the Y247 or Y425 in full-length PKG-1α. For example, in some embodiments, the nitration shielding peptide includes 111-342 of SEQ ID NO:26 (i.e., the two cGMP binding sites PKG-1α), or a functional fragment or variant thereof. In some embodiments, the nitration shielding peptide includes amino acids 344-474 of SEQ ID NO:26 (i.e., an ATP-binding site) or a functional fragment or variant thereof. In some embodiments, the nitration shielding peptide binds to 111-342 of SEQ ID NO:26, amino acids 344-474 of SEQ ID NO:26, or a fragment thereof.

2. Nucleic Acids Encoding Nitration Shielding Peptides
a. Isolated Nucleic Acids Isolated nucleic acid sequences encoding nitration shielding peptides and fusions thereof are also disclosed. As used herein, "isolated nucleic acid" refers to a nucleic acid that is separated from other nucleic acid molecules that are present in a mammalian genome, including nucleic acids that normally flank one or both sides of the nucleic acid in a mammalian genome. The term "isolated" as used herein with respect to nucleic acids also includes the combination with any non-naturally-occurring nucleic acid sequence, since such non-naturally-occurring sequences are not found in nature and do not have immediately contiguous sequences in a naturally-occurring genome.

An isolated nucleic acid can be, for example, a DNA molecule, provided one of the nucleic acid sequences normally found immediately flanking that DNA molecule in a naturally-occurring genome is removed or absent. Thus, an isolated nucleic acid includes, without limitation, a DNA molecule that exists as a separate molecule independent of other sequences (e.g., a chemically synthesized nucleic acid, or a cDNA or genomic DNA fragment produced by PCR or restriction endonuclease treatment), as well as recombinant DNA that is incorporated into a vector, an autonomously replicating plasmid, a virus (e.g., a retrovirus, lentivirus, adenovirus, or herpes virus), or into the genomic DNA of a prokaryote or eukaryote. In addition, an isolated nucleic acid can include an engineered nucleic acid such as a recombinant DNA molecule that is part of a hybrid or fusion nucleic acid. A nucleic acid existing among hundreds to millions of other nucleic acids within, for example, a cDNA library or a genomic library, or a gel slice containing a genomic DNA restriction digest, is not to be considered an isolated nucleic acid.

Nucleic acids encoding nitration shielding peptides and fusion proteins thereof may be optimized for expression in the expression host of choice. Codons may be substituted with alternative codons encoding the same amino acid to account for differences in codon usage of the expression host. In this manner, the nucleic acids may be synthesized using expression host-preferred codons.

Nucleic acids can be in sense or antisense orientation, or can be complementary to a reference sequence encoding a nitration shielding peptide and fusion protein thereof. Nucleic acids can be DNA, RNA, or nucleic acid analogs. Nucleic acid analogs can be modified at the base moiety, sugar moiety, or phosphate backbone. Such modification can improve, for example, stability, hybridization, or solubility of the nucleic acid. Modifications at the base moiety can include deoxyuridine for deoxythymidine, and 5-methyl-2'-deoxycytidine or 5-bromo-2'-deoxycytidine for deoxycytidine. Modifications of the sugar moiety can include modification of the 2' hydroxyl of the ribose sugar to form 2'-O-methyl or 2'-O-allyl sugars. The deoxyribose phosphate backbone can be modified to produce morpholino nucleic acids, in which each base moiety is linked to a six membered, morpholino ring, or peptide nucleic acids, in which the deoxyphosphate backbone is replaced by a pseudopeptide backbone and the four bases are retained. See, for example, Summerton and Weller (1997) *Antisense Nucleic Acid Drug Dev.* 7:187-195; and Hyrup et al. (1996) *Bioorgan. Med. Chem.* 4:5-23. In addition, the deoxyphosphate backbone can be replaced with, for example, a phosphorothioate or phosphorodithioate backbone, a phosphoroamidite, or an alkyl phosphotriester backbone.

Nucleic acids encoding polypeptides can be administered to subjects in need thereof. Nucleic delivery involves introduction of "foreign" nucleic acids into a cell and ultimately, into a live animal. Compositions and methods for delivering nucleic acids to a subject are known in the art (see Understanding Gene Therapy, Lemoine, N. R., ed., BIOS Scientific Publishers, Oxford, 2008). Accordingly, in some embodiments nucleic acids encoding a nitration shielding peptide and or a fusion protein thereof are delivered to a subject of cell thereof or isolated therefrom. The nucleic acids can express the nitration shielding peptides and fusion proteins thereof in the subject leading to reduced protein nitration in the subject. Therefore, protein nitration can be reduced by gene therapy directed to expression of nitration shielding peptides or fusion proteins thereof.

b. Vectors and Host Cells

Vectors encoding nitration shielding peptides and fusion proteins thereof, fragments and fusions thereof are also provided. Nucleic acids, such as those described above, can be inserted into vectors for expression in cells. As used herein, a "vector" is a replicon, such as a plasmid, phage, virus or cosmid, into which another DNA segment may be inserted so as to bring about the replication of the inserted segment. Vectors can be expression vectors. An "expression vector" is a vector that includes one or more expression control sequences, and an "expression control sequence" is a DNA sequence that controls and regulates the transcription and/or translation of another DNA sequence.

Nucleic acids in vectors can be operably linked to one or more expression control sequences. As used herein, "operably linked" means incorporated into a genetic construct so that expression control sequences effectively control expression of a coding sequence of interest. Examples of expression control sequences include promoters, enhancers, and transcription terminating regions. A promoter is an expression control sequence composed of a region of a DNA molecule, typically within 100 nucleotides upstream of the point at which transcription starts (generally near the initiation site for RNA polymerase II). To bring a coding sequence under the control of a promoter, it is necessary to position the translation initiation site of the translational reading frame of the polypeptide between one and about fifty nucleotides downstream of the promoter. Enhancers provide expression specificity in terms of time, location, and level. Unlike promoters, enhancers can function when located at various distances from the transcription site. An enhancer also can be located downstream from the transcription initiation site. A coding sequence is "operably linked" and "under the control" of expression control sequences in a cell when RNA polymerase is able to transcribe the coding sequence into mRNA, which then can be translated into the protein encoded by the coding sequence.

Suitable expression vectors include, without limitation, plasmids and viral vectors derived from, for example, bacteriophage, baculoviruses, tobacco mosaic virus, herpes viruses, cytomegalo virus, retroviruses, vaccinia viruses, adenoviruses, and adeno-associated viruses. Numerous vectors and expression systems are commercially available from such corporations as Novagen (Madison, Wis.), Clontech (Palo Alto, Calif.), Stratagene (La Jolla, Calif.), and Invitrogen Life Technologies (Carlsbad, Calif.).

An expression vector can include a tag sequence. Tag sequences, are typically expressed as a fusion with the encoded polypeptide. Such tags can be inserted anywhere within the polypeptide including at either the carboxyl or amino terminus. Examples of useful tags include, but are not limited to, green fluorescent protein (GFP), glutathione S-transferase (GST), polyhistidine, c-myc, hemagglutinin, Flag™ tag (Kodak, New Haven, Conn.), maltose E binding protein and protein A. In one embodiment, a nucleic acid molecule encoding a B7-H4 fusion polypeptide is present in a vector containing nucleic acids that encode one or more domains of an Ig heavy chain constant region, preferably having an amino acid sequence corresponding to the hinge, $C_H2$ and $C_H3$ regions of a human immunoglobulin Cγ1 chain.

Vectors containing nucleic acids to be expressed can be transferred into host cells. The term "host cell" is intended to include prokaryotic and eukaryotic cells into which a recombinant expression vector can be introduced.

As used herein, "transformed" and "transfected" encompass the introduction of a nucleic acid molecule (e.g., a vector) into a cell by one of a number of techniques. Although not limited to a particular technique, a number of these techniques are well established within the art. Prokaryotic cells can be transformed with nucleic acids by, for example, electroporation or calcium chloride mediated transformation. Nucleic acids can be transfected into mammalian cells by techniques including, for example, calcium phosphate co-precipitation, DEAE-dextran-mediated transfection, lipofection, electroporation, or microinjection. Host cells (e.g., a prokaryotic cell or a eukaryotic cell such as a CHO cell) can be used to, for example, produce the nitration shielding peptides and fusion proteins thereof described herein.

The vectors described can be used to express nitration shielding peptides and fusion proteins thereof in cells, for example, cells in a subject or cells to transferred or implanted into a subject. An exemplary vector includes, but is not limited to, an adenoviral vector. One approach includes nucleic acid transfer into primary cells in culture followed by autologous transplantation of the ex vivo transformed cells into the host, either systemically or into a particular organ or tissue. Ex vivo methods can include, for example, the steps of harvesting cells from a subject, culturing the cells, transducing them with an expression vector, and maintaining the cells under conditions suitable for expression of the encoded polypeptides. These methods are known in the art of molecular biology. The transduction step can be accomplished by any standard means used for ex vivo gene therapy, including, for example, calcium phosphate, lipofection, electroporation, viral infection, and biolistic gene transfer. Alternatively, liposomes or polymeric microparticles can be used. Cells that have been successfully transduced then can be selected, for example, for expression of the coding sequence or of a drug resistance gene. The cells then can be lethally irradiated (if desired) and injected or implanted into the subject. In one embodiment, expression vectors containing nucleic acids encoding fusion proteins are transfected into cells that are administered to a subject in need thereof.

In vivo nucleic acid therapy can be accomplished by direct transfer of a functionally active DNA into mammalian somatic tissue or organ in vivo. Nucleic acids may also be administered in vivo by viral means. Nucleic acid molecules encoding fusion proteins may be packaged into retrovirus vectors using packaging cell lines that produce replication-defective retroviruses, as is well-known in the art. Other virus vectors may also be used, including recombinant adenoviruses and vaccinia virus, which can be rendered non-replicating. In addition to naked DNA or RNA, or viral vectors, engineered bacteria may be used as vectors. Nucleic acids may also be delivered by other carriers, including liposomes, polymeric micro- and nanoparticles and polycations such as asialoglycoprotein/polylysine.

In addition to virus- and carrier-mediated gene transfer in vivo, physical means well-known in the art can be used for direct transfer of DNA, including administration of plasmid DNA and particle-bombardment mediated gene transfer.

3. Methods of Making Nitration Shielding Peptides

The nitration shielding peptides and fusion proteins thereof can be prepared using any suitable method known in the art. For example, the peptides can be prepared using peptide synthesis method including, but not limited to liquid-phase synthesis and solid-phase synthesis; in vivo recombinant protein expression; and cell free synthesis.

Molecular biology techniques have developed so that therapeutic proteins can be genetically engineered to be expressed by microorganisms. The gram negative bacterium, *Escherichia coli*, is a versatile and valuable organism for the expression of therapeutic proteins. Although many proteins with therapeutic or commercial uses can be produced by recombinant organisms, the yield and quality of the expressed protein are variable due to many factors. For example, heterologous protein expression by genetically engineered organisms can be affected by the size and source of the protein to be expressed, the presence of an affinity tag linked to the protein to be expressed, codon biasing, the strain of the microorganism, the culture conditions of microorganism, and the in vivo degradation of the expressed protein. Some of these problems can be mitigated by fusing the protein of interest to an expression or solubility enhancing amino acid sequence. Exemplary expression or solubility enhancing amino acid sequences include maltose-binding protein (MBP), glutathione S-transferase (GST), thioredoxin (TRX), NUS A, ubiquitin (Ub), and a small ubiquitin-related modifier (SUMO).

In some embodiments, the compositions disclosed herein include expression or solubility enhancing amino acid sequence. In some embodiments, the expression or solubility enhancing amino acid sequence is cleaved prior administration of the composition to a subject in need thereof. The expression or solubility enhancing amino acid sequence can be cleaved in the recombinant expression system, or after the expressed protein in purified. In some embodiments, the expression or solubility enhancing is a ULP1 or SUMO sequence. Recombinant protein expression systems that incorporate the SUMO protein ("SUMO fusion systems") have been shown to increase efficiency and reduce defective expression of recombinant proteins in *E. coli*., see for example Malakhov, et al., *J. Struct. Funct. Genomics,* 5: 75-86 (2004), U.S. Pat. Nos. 7,060,461, and 6,872,551. SUMO fusion systems enhance expression and solubility of certain proteins, including severe acute respiratory syndrome coronavirus (SARS-CoV) 3CL protease, nucleocapsid, and membrane proteins (Zuo, et al., *J. Struct. Funct. Genomics,* 6:103-111 (2005)).

In some embodiments, the peptides are synthesized using a cell free system. The advantages of cell-free systems, which have been extensively developed, include the ability to synthesize toxic proteins, aggregated proteins and proteins containing unnatural amino acids, however, such systems can suffer from low yield.

Preparation of the peptides can include one or more purification steps based on the physiochemical characteristics of peptides, including size, charge and hydrophobicity. Peptide purification techniques include, but are not limited to, size-exclusion chromatography, ion exchange chromatography (TEC), partition chromatography, and high-performance liquid chromatography (HPLC).

III. Methods of Use

Nitrotyrosine accumulation reflects a loss of balance between oxidant formation and antioxidant defense mechanisms, formerly known as oxidative stress (Peluffo and Radi, *Cardiovascular Research,* 75:291-302 (2007)). Nitration is known to alter the function of the some proteins which can induce or exacerbate a wide breadth of physiological changes and pathologies, and is associated with diseases including various lung ailments, autoimmune and inflammatory responses, vascular diseases and neurodegenerative diseases. The disclosed nitration shielding peptides and compositions thereof can be used to block or otherwise reduce intracellular or extracellular protein nitration in a subject (i.e., in vivo), or in cells in vitro or ex vivo. The peptides and compositions thereof can also be used to treat one or more symptoms of a pathology, disease, or disorder associated with protein nitration.

A. Methods of Blocking Protein Nitration

Methods of blocking or otherwise reducing protein nitration using the disclosed nitration shielding peptides and compositions thereof are provided. The peptides are typically brought into proximity, or direct or indirect contact with the protein of interest in an effective amount to block or reduce nitration of the protein in the presence of a nitrating agent compared to a control. The contacting can occur intracellularly or extracellularly. In preferred embodiments, the method includes introducing the peptide into a cell and the contacting occurs intracellularly. The contracting can occur in a subject in vivo.

Preferably, the nitration shielding peptide binds directly or indirectly to the protein of interest and blocks, prevents, or reduces the frequency or efficacy of nitration of one or more amino acid residues of the protein of interest by a protein nitrating agent. In some embodiments the nitration shielding peptide includes a tyrosine that can be nitrated. Nitration of the peptide blocks or reduces nitration of the protein of interest, and does not substantially alter the protein's function. In some embodiments the nitration shielding peptide includes an antioxidant that reduces or counteracts the ability or frequency with which the nitration agent can nitrate the protein of interest.

Protein nitration can alter the function of proteins. In some cases, protein nitration increases the function or activity of a protein. In some cases, protein nitration reduces or slows the function or activity of a protein. The effect of protein nitration on the function or activity of a protein can have pathological consequences leading to development or exacerbation of a wide breadth of diseases and disorders. Typically the disclosed nitration shielding peptides allow a protein of interest to maintain a level of function or activity in the presence of a protein nitrating agent that is similar to the level of the function or activity of the protein in the absence of the protein nitrating agent. Therefore, the function or activity of the protein of interest in the presence of a protein nitrating agent is less altered in the presence of a nitration shielding peptide than in the absence of the nitration shielding peptide. For example, if the protein nitrating agent causes at least 10, 20, 30, 40, 50, 60, 70, 80, 90, 100, 250, 500, 1,000, or at least 10,000 percent alteration in the function or activity of the protein of interest without the nitration shielding peptide, the protein nitrating agent can cause less than about 10, 20, 30, 40, 50, 60, 70, 80, 90, 100, 250, 500, 1,000, or 10,000 percent, respectively, alteration in the function or activity of the protein of interest in the presence of the nitration shielding. The alteration caused by the protein nitrating agent can be an increase or decrease in a function or activity of the protein.

Protein nitrating agents are known in the art. See, for example, Gow, et al., *Am. Physiol. Lung Cell Mol. Physiol.*, 287:L262-L268 (2004). Protein tyrosine nitration appears to be catalyzed, primarily by metalloproteins. Evidence indicates that myeloperoxidase, eosinophil peroxidase, myoglobin, and the cytochrome P-450s catalyze the oxidation of nitrite to nitrogen dioxide, which is capable of nitrating tyrosine residues. Moreover, myeloperoxidase also catalyzes protein nitration by peroxynitrite, the product of the near diffusion-limited reaction of NO with superoxide. Metalloproteins such as Mn superoxide dismutase and prostacyclin synthase could catalyze their own nitration from peroxynitrite.

Nonenzymatic sources of tyrosine nitration include the intermediate of the reaction between peroxynitrite with carbon dioxide and the acidification of nitrite to form nitrous acid, an agent capable of nitrating tyrosine residues. The term reactive nitrogen species (RNS) has been introduced in the biological literature to refer to nitric oxide and other NO-related molecules, such as S-nitrosothiols (RSNOs), peroxynitrite (ONOO—), dinitrogen trioxide ($N_2O_3$) and nitrogen dioxide ($NO_2$) among others, which have relevant roles in multiple physiological processes of animal and plant cells. These molecules are directly or indirectly involved in post-translational modifications in cell signaling under physiological and pathological conditions including binding to metal centres, S-nitrosylation of thiol groups and nitration of tyrosine (Corpas, et al., *Plant Signaling & Behavior*, 4(10):920-923 (2009)).

In some of the Examples below, the protein nitrating agent is peroxynitrite (ONOO—). Accordingly, in some embodiments the effect of nitration shielding peptide on nitration is compared to nitration of a non-treated or vehicle treated control each in the presence of ONOO—.

For in vivo embodiments, the control can also be the subject prior to treatment or a sample or measurement obtained therefrom, or an untreated or vehicle treated control subject suffering from a similar condition, disease, or symptoms. The nitrating agent may or may not be known. The effect of the nitration shielding peptide can be a reduction in nitration of the protein of interest or an improvement in one or more symptoms or conditions for which the subject is being treated. Methods of measuring nitration are discussed in the Examples below and include immunoassays, various methods of chromatography (e.g., HPLC), mass spectroscopy, and combinations thereof.

1. Methods of Treating Diseases and Disorders

Nitration shielding agents and compositions, particularly the disclosed nitration shielding peptides, can be used to treat or prevent one or more symptoms of a disease or disorder characterized by protein nitration. The compositions can be administered to a subject in an effective amount to treat diseases and disorders associated with oxidative stress and nitrative damage or symptom, characteristic or comorbidity thereof.

In some embodiments the disclosed nitration shielding agents can be used to treat or prevent one or more symptoms of a disease or disorder associated with increased nitration, for example by restoring the normal function or concentration of a protein. In certain embodiments the methods of treating or preventing one or more symptoms of a disease or disorder can include preventing changes to the structure and/or function of proteins that occur as a result of tyrosine nitration. For example, the methods can be useful to restore or enhance enzyme activity; restore or enhance antigen recognition; restore or enhance immune function; restore or enhance metabolic activity; reduce or prevent tissue damage; enhance tissue repair; or combinations thereof.

The methods for preventing tyrosine nitration may prevent disruption of normal signaling pathways, or can restore signaling pathways that have become disrupted as a result of a disease or disorder. For example, the disclosed methods can prevent or reduce nitrative damage associated with the progression of diabetes, as well as cardiovascular problems associated with diabetes.

In some embodiments the disclosed methods prevent diseases and disorders associated with the undesirable activation of the immune system in response to nitrative damage. For example, the disclosed methods can prevent the stimulation of macrophage cells, prevent the production of elevated cytokines and chemokines, prevent the infiltration of neutrophils, or prevent the development or progression of inflammatory tissue injury or cutaneous inflammation.

In other embodiments it may be advantageous to prevent nitration of a protein below the normal levels to counteract the effects of a disease, disorder or toxin. In particular embodiments, nitration shielding peptides are useful for counteracting protein nitration that occurs as a result of drug use, for example counteracting the protein nitration that occurs as a side effect of acetaminophen use.

Therefore, nitration shielding peptides can be useful to restore, prevent, enhance or otherwise manipulate the activity of a protein to prevent, inhibit or reduce the severity of various diseases or disorders. For example, the methods can include administering to a subject in need thereof an effective amount of one or more of the disclosed nitration shielding compositions to reduce, delay, or inhibit the symptoms of one or more diseases or disorders associated with the presence or accumulation of one or more nitratively damaged or misfolded proteins.

A non-limiting list of diseases and disorders that can be treated with the disclosed nitration shielding peptides includes hepatic diseases (alcoholic fatty liver disease, non-alcoholic fatty liver disease and cirrhosis); cardiovascular diseases and disorders (cardiovascular inflammation, autoimmune myocarditis, heart failure, ischemia-reperfusion injury, cardiac allograft rejection, transplant coronary artery disease, pulmonary hypertension, atherosclerosis, restenosis, hypoxia, vasoconstriction, vascular remodeling, vascular dysfunction, coronary artery disease, hypoxemic respiratory failure); proteinopathies (Alzheimer's disease, cerebral β-amyloid angiopathy, retinal ganglion cell degeneration in glaucoma, prion diseases, Parkinson's disease and other synucleinopathies, tauopathies, frontotemporal lobar degeneration (FTLD), FTLD-FUS, amyotrophic lateral sclerosis (ALS), Huntington's disease and other triplet repeat disorders, familial British dementia, familial Danish dementia, hereditary cerebral hemorrhage with amyloidosis (Icelandic) (HCHWA-I), CADASIL, Alexander disease, seipinopathies, familial amyloidotic neuropathy, senile systemic amyloidosis, serpinopathies, AL (light chain) amyloidosis (primary systemic amyloidosis), AH (heavy chain) amyloidosis, AA (secondary) amyloidosis, Type II diabetes, aortic medial amyloidosis, ApoAI amyloidosis, ApoAII amyloidosis, ApoAIV amyloidosis, familial amyloidosis of the Finnish type (FAF), lysozyme amyloidosis, fibrinogen amyloidosis, dialysis amyloidosis, inclusion body myositis/myopathy, cataract, retinitis pigmentosa with rhodopsin mutations, medullary thyroid carcinoma, cardiac atrial amyloidosis, pituitary prolactinoma, hereditary lattice corneal dystrophy, cutaneous lichen amyloidosis, Mallory bodies, corneal lactoferrin amyloidosis, pulmonary alveolar proteinosis, odontogenic (Pindborg) tumor amyloid, seminal vesicle amyloid, cystic fibrosis, sickle cell disease, and critical illness myopathy (CIM); stroke; diabetes; kidney diseases; cancer; as well as inflammatory responses or autoimmune diseases (rheumatoid arthritis, systemic lupus erythematosus, alopecia greata, anklosing spondylitis, antiphospholipid syndrome, autoimmune Addison's disease, autoimmune hemolytic anemia, autoimmune hepatitis, autoimmune inner ear disease, autoimmune lymphoproliferative syndrome (alps), autoimmune thrombocytopenic purpura (ATP), Behcet's disease, bullous pemphigoid, cardiomyopathy, celiac sprue-dermatitis, chronic fatigue syndrome immune deficiency, syndrome (CFIDS), chronic inflammatory demyelinating polyneuropathy, cicatricial pemphigoid, cold agglutinin disease, Crest syndrome, Crohn's disease, Dego's disease, dermatomyositis, dermatomyositis—juvenile, discoid lupus, essential mixed cryoglobulinemia, fibromyalgia—fibromyositis, grave's disease, guillain-barre, hashimoto's thyroiditis, idiopathic pulmonary fibrosis, idiopathic thrombocytopenia purpura (ITP), Iga nephropathy, insulin dependent diabetes (Type I), juvenile arthritis, Meniere's disease, mixed connective tissue disease, multiple sclerosis, myasthenia gravis, pemphigus vulgaris, pernicious anemia, polyarteritis nodosa, polychondritis, polyglancular syndromes, polymyalgia rheumatica, polymyositis and dermatomyositis, primary agammaglobulinemia, primary biliary-cirrhosis, psoriasis, Raynaud's phenomenon, Reiter's syndrome, rheumatic fever, sarcoidosis, scleroderma, Sjogren's syndrome, stiff-man syndrome, Takayasu arteritis, temporal arteritis/giant cell arteritis, ulcerative colitis, uveitis, vasculitis, vitiligo, and Wegener's granulomatosis).

Exemplary diseases and disorders that have been associated with protein tyrosine nitration, including a list of the respective proteins that have been linked with the disease are provided in Table 2, adapted from Yeo, et al., BMB Reports, 41(3):194-203 (2008).

TABLE 2

List of Selected Nitrated Proteins in Various Diseases
Cellular Compartment

| Protein | Biological functions | Diseases |
| --- | --- | --- |
| Extracellular space | | |
| Fibrinogen | Signal transduction | Coagulation disorder |
| Plasminogen | Plasmin activity | Diabetes, atherosclerosis |
| Surfactant protein A | Lipid transporter activity | Inflammation |
| Nucleus | | |
| p130 adhesion protein | Protein binding | Stroke, neurodegenerative disorders |
| Cu, Zn-SOD | Negative regulation of apoptosis | Neurodegenerative disorders |
| p53 tumor suppressor | Transcription factor activity | Cancer |
| Histones | DNA binding | Cancer |
| Profilin | Regulation of transcription from RNA polymerase II promoter | Platelet dysfunction |
| Cytoplasm | | |
| Insulin receptor substrate-I | Transmembrane receptor protein kinase docking | Diabetes |
| Clutamine synthetase | Glutamate-ammonia ligase activity | Sepsis, liver disease |
| INOS | Nitric-oxide synthase activity | Inflammation |
| Histone deacetylase II | Chromatin modification | Inflammation |
| Profilin | Regulation of transcription form RNA polymerase II promoter | Platelet dysfunction |
| Tau protein | Exocytosis | Alzheimer's disease |
| Alpha synuclein | Central nervous system development | Parkinson's disease |
| Alpha-enolase | Glycolysis | Alzheimer's disease |
| Triosephosphate isomerase | Glycolysis | Alzheimer's disease |
| Mitochondria | | |
| Carnitine palmitoyltransferase I | Acyltransferase activity | Septic myocardial dysfuntion |
| Creatine kinase | Creatine kinase activity | Myocardial infarction |
| GAPDH | Glycolysis | Cardiovascular and neurological diseases |
| Mn-SOD | Superoxide dismutase activity | Neurodegenerative disorders |
| Nicotinamide nucleotide transhydrogenase | Electron transport | Inflammation, shock, ischemia |
| Cytochrome c | Aerobic respiration | Inflammation, shock, ischemia |
| ATP synthase complex 5 | Hydrogen ion transporting ATP synthase activity | Inflammation, shock, ischemia |
| Plasma membrane | | |
| SERCA2A | Cation transport | Myocardial infarction |
| Amiloride-sensitive NA+ channel | Ion channel activity | Inflammation |
| Cytoskeleton | | |
| Desmin | Cytoskeleton organization and biogenesis | Chronic heart failure |
| Tubulin | Protein polymerization | Shock, ischemia |
| Neurofilament L | Structural constituent of cytoskeleton | Amyotrophic lateral sclerosis |
| Actin | Muscle thin filament assembly | Endothelial dysfuntion |
| Endoplasmic reticulum | | |
| Prostacyclin synthase | Fatty acid biosynthetic process | Endothelial dysfunction, diabetes |

For example, the nitration shielding peptide or compositions thereof can be used to reduce or prevent nitration of any of the proteins listed in Table 2 under the column labeled "Protein" to treat or prevent the diseases listed in Table 2 under the column labeled "Diseases".

Exemplary methods of using nitration shielding agents include preventing the over activation of enzymes (e.g., preventing over-activation of the GTPase RhoA) and preventing the inhibition of enzymes (e.g., preventing PKG-1α inhibition).

i. Methods of Preventing RhoA Over-Activation

It has been discovered that increases in RhoA nitration leads to enhanced GTPase activity through alterations in nucleotide cycling. It is believed that nitration of a single site on RhoA (Y34) is responsible for the increase in RhoA activity. Therefore, the peptides and compositions thereof disclosed herein can be used to prevent or reduce nitration-mediated activation of RhoA.

Both superoxide and nitrogen dioxide have been shown to accelerate GDP release from RhoA, Rac1 and Cdc42, by affecting the GXXXXGK(S/T)C SEQ ID NO:18 motif (Heo, J., et al., *J Biol. Chem.* 280, 31003-31010 (2005)), G, K, T and S denote glycine, lysine, threonine and serine residues respectively, and X denotes any amino acid. From these data it was concluded that cysteine 18 and phenylalanine 28 (RhoA sequence) mediate the redox sensitivity of the small GTPases. However, RhoA has also been shown to be inactivated by redox agents due to formation of an intermolecular disulfide bond (Heo, et al., *Biochemistry* 45, 14481-14489 (2006)). Adding to these studies, the data in the Examples below show the involvement of RhoA protein nitration in endothelial barrier disruption.

Y34 is located in a flexible region of RhoA within Switch I domain (Wei, et al., *Nat. Struct. Biol.* 4, 699-703 (1997)), referred to herein as the "flap" region. This domain is important for nucleotide and magnesium binding within the catalytic cavity. Changes in the molecular conformations of the flap domain have been shown to occur during catalytic cycling (Shimizu, et al., *J Biol. Chem.* 275, 18311-18317 (2000); Scheffzek, K., et al., *Nat. Struct. Biol.* 7, 122-126 (2000); Ihara, et al., *J. Biol. Chem.* 273, 9656-9666 (1998)). The catalytic cycling of RhoA consists of three major steps: 1) GTP binding to RhoA which represents the active conformation of the enzyme with the flap being in a closed conformation; 2) after phosphate bond cleavage of GTP, RhoA returns to an inactive conformation with GDP bound and with the flap partially open; 3) RhoA releases GDP from the inactive conformation, usually by GEF protein assistance, and, with a fully open flap, waits for binding to a new GTP molecule. Molecular dynamic simulations and rapid-flow kinetic studies indicate that the conformational changes in the flap region of RhoA-GDP complex after Y34 nitration mimics the conformational shift observed in the flap in a GEF-RhoA complex while GTP binding is unaffected. Therefore, it is believed that nitration of Y34 leads to "GEF-like" movement in the flap region while in the GDP bound state resulting in faster GDP release, and GTP reload, leading to an increase in RhoA activity.

Y34 is subjected to AMPylation (Yarbrough, et al., *Science* 323, 269-272 (2009)) and may also be subject to phosphorylation. Modification of Y34 by adenosine monophosphate results in RhoA inhibition, probably due to steric hindrance of the nucleotide binding site. Further, it is likely that the nitration of Y34 would inhibit phosphorylation and/or AMPylation of RhoA. Thus, the competition among these various modifications for one, very important, site of RhoA is believed to have both physiological and pathological implications.

The peptides and compositions disclosed herein can be used to reduce RhoA nitration. Therefore, the peptides and compositions disclosed herein can be used to reduce RhoA activity. More specifically, the peptide and compositions can be used to reduce or prevent the increase in speed of GDP release and GTP reload caused by nitration of Y34 of RhoA.

In a preferred embodiment, the composition includes one or more of the RhoA nitration shielding peptides or fusion proteins thereof disclosed above or in the Examples below. Without being bound by theory, the exemplary RhoA nitration shielding peptides provided above and below are believed to prevented nitration of RhoA by shielding RhoA protein from peroxynitrite attack. It is believed that the peptides provide an alternative tyrosine residue to react with peroxynitrite rather than simply sterically inhibiting the access of peroxynitrite to the protein. This possibility is supported by the data in the Examples below demonstrating that despite its ability to bind to RhoA, a control peptide in which the Y34 was mutated to a phenylalanine did not prevent the nitration-mediated activation of RhoA. Of note, the Examples below also show that RhoA nitration shielding peptides can reduce LPS mediated RhoA nitration, without affecting nitration of other proteins, indicating that it peptides can target RhoA specifically rather than acting as a generic peroxynitrite sink.

a. Method of Increasing Endothelial Cell Barrier Function

The molecular mechanisms underlying endothelial hyperpermeability are reviewed in Kumar, et al., *Expert Rev Mol. Med.*; 11: e19. doi:10.1017/S1462399409001112 pages 1-23 (2010). Endothelial hyperpermeability is a significant problem in vascular inflammation associated with trauma, ischaemia-reperfusion injury, sepsis, adult respiratory distress syndrome, diabetes, thrombosis and cancer. An important mechanism underlying this process is increased paracellular leakage of plasma fluid and protein. Inflammatory stimuli such as histamine, thrombin, vascular endothelial growth factor and activated neutrophils can cause dissociation of cell-cell junctions between endothelial cells as well as cytoskeleton contraction, leading to a widened intercellular space that facilitates transendothelial flux. Such structural changes initiate with agonist-receptor binding, followed by activation of intracellular signaling molecules including calcium, protein kinase C, tyrosine kinases, myosin light chain kinase, and small Rho-GTPases; these kinases and GTPases then phosphorylate or alter the conformation of different subcellular components that control cell-cell adhesion, resulting in paracellular hyperpermeability.

The small GTPases of the Rho protein family, RhoA, Rac1 and Cdc42 are key regulators of the actin cytoskeleton (Bruewer, M., et al., *Am. J. Physiol. Cell Physiol.* 287, C327-335 (2004)). Rac1 and RhoA have antagonistic effects on endothelial barrier function in the lung (Wojciak-Stothard, et al., *J. Cell Sci.* 114, 1343-1355 (2001); Huang, Subbaiah, et al., *Am. J. Physiol. Lung Cell Mol. Physiol.* 289, L176-185 (2005)). Rac1 is required for the assembly and maturation of endothelial junctions, whereas RhoA destabilizes endothelial junctions by increasing isometric tension at the cell membrane (Goeckeler, *J. Biol. Chem.* 280, 33083-33095 (2005) and subsequently increasing myosin driven contractility. RhoA activation is important in the regulation of the endothelial barrier and it has been shown that cytokine production in smooth muscle cells correlates with RhoA activation (Carbajal, J. M., et al., *Am. J. Physiol.* 277, C955-964 (1999); Harrington, E. O., et al., *Am. J. Physiol. Lung Cell Mol. Physiol.* 287, L1091-1097 (2004)).

Accordingly, methods of maintaining or improving endothelial barrier function, particular endothelial barrier function in the lungs, are disclosed. The methods typically include contacting one or more nitration shielding peptides or a composition thereof with RhoA expressed in cells that contribute to barrier function in an effective amount to reduce nitration of RhoA, reduce activation of RhoA, or preferably a combination thereof in the cells compared to a control. Preferable the compositions reduce or prevent one or more hallmarks of endothelial hyperpermeability, such as those discussed in Kumar, et al., *Expert Rev. Mol. Med.*, 11: e19. doi:10.1017/S1462399409001112 pages 1-23 (2010), which is specifically incorporated by reference herein in its entirety. For example, the compositions can be introduced into endothelial cells such as lung endothelial cells. In a particular embodiment the compositions include a protein transduction domain, a lung cell targeting signal, an endothelial cell target signal, or any combination thereof to facilitate delivery of the peptide to the interior of the endothelial cell. Methods of delivering peptides and compositions thereof to the lungs are discussed in more detail below.

b. Diseases to be Treated

RhoA nitration shielding peptides and compositions, particularly the disclosed RhoA nitration shielding peptides, can be used to treat one or more symptoms of a disease or disorder associated with increased RhoA activation, particularly those caused or exacerbated by hyperpermeability of endothelial junctions. Exemplary diseases and disorders include, but are not limited to, acute lung injury (ALI), acute respiratory distress syndrome (ARDS), ventilator-induced lung injury (VILI), ventilator-associated lung injury (VALI), lung infections, trauma, ischaemia reperfusion injury, sepsis, diabetes, thrombosis, cancer and combinations thereof.

The Examples below show that lipopolysacchardies (LPS) can induce nitration of RhoA Y34 via nitric oxide synthases (NOS). Mice treated with LPS exhibited elevated levels of activated RhoA, impaired lung endothelial barrier function, and develop acute lung injury-like symptoms and pathologies including weight loss, cell infiltration into the bronchoalveolar lavage fluid (BALF), severe alveolar damage, a large amount of neutrophils and red blood cells in the alveolar and interstitial space, formation of hyaline membranes, septal thickening, debris accumulation in the alveoli, increased myeloperoxidase (MPO) presence in the alveolar space and reduced MPO activity in lung cells. The Examples also show that treatment of the mice with a RhoA nitration shielding peptide reduced these symptoms and pathologies relative to an untreated control. A RhoA nitration shielding peptide also preserved endothelial barrier function and attenuated the levels of inflammatory cytokines and chemokines in the BALF, which correlated with the decreased macrophage and neutrophil infiltration into the lungs. It is well established that vascular cells (endothelial and smooth muscle) produce chemokines and cytokines that result in the attraction of neutrophils and macrophages (Dechend, R., et al., *Circulation* 108, 261-265 (2003); Magder, S., et al., *J. Vasc. Res.* 43, 447-461 (2006)).

Accordingly, in some embodiments, the peptides or combinations thereof are administered to a subject in an effective amount to reduce or prevent weight loss, reduce or prevent cell infiltration into the bronchoalveolar lavage fluid (BALF), reduce or prevent alveolar damage, reduce or prevent the number of neutrophils and red blood cells in the alveolar and interstitial space, reduce or prevent formation of hyaline membranes, reduce or prevent septal thickening, reduce or prevent debris accumulation in the alveoli, reduce or prevent increases myeloperoxidase (MPO) presence in the alveolar space, reduce or prevent a reduction MPO activity in lung cells, preserve endothelial barrier function, reduce production or expression of proinflammatory chemokines and cytokines (particularly those that attract neutrophils and macrophages), or any combination thereof. In some embodiments the subject has an infection. The infection can be caused by gram-negative bacteria. The subject can have one or more symptoms or pathologies associated with lung injury, for example injury caused by LPS.

The Examples also show that nitration-induced increases in RhoA can be attenuated without affecting basal RhoA activity. Therefore, if RhoA nitration shielding peptides gain access to tissues besides the lung, it is believed that the peptides will not alter physiologic RhoA signaling. This can be important as RhoA is also involved in maintaining the endothelial cytoskeleton in a conformation that maintains a tight barrier (Shen, Q., et al., *Cell Health Cytoskelet.* 2009, 43-50 (2009)). Therefore the RhoA nitration peptides can be safely and efficaciously administered locally or systemically.

c. Methods of Diagnosis

It has been discovered that nitration of Y34 of RhoA, particularly in endothelial cells, is a biomarker for endothelial hyperpermeability and many of the disease and disorder associated therewith, including, but not limited to acute lung injury (ALI), acute respiratory distress syndrome (ARDS), ventilator-induced lung injury (VILI), ventilator-associated lung injury (VALI), lung infections and others. Therefore, the level of Y34 nitration of RhoA can be used to identify subjects with, or at increased risk of developing, endothelial hyperpermeability. The level of nitration of Y34 of RhoA can also be used to assist in the diagnosis of acute lung injury (ALI), acute respiratory distress syndrome (ARDS), ventilator-induced lung injury (VILI), ventilator-associated lung injury (VALI), lung infections, trauma, ischaemia-reperfusion injury, sepsis, diabetes, thrombosis, cancer, or other diseases and disorders associated with endothelium hyperpermeability.

A typical method includes measuring the level of nitration of Y34 in a subject or a biological sample obtained from a subject. In a preferred embodiment, the sample is a lung sample, for example a lung biopsy and comparing it to control. Typically, an increased level of Y34 nitration compared to a control is indicative of the subject having, or at an increased risk of developing, endothelial hyperpermeability or a disease or disorder associated therewith. The control can be, for example, a corresponding sample from an individual that does not have endothelial hyperpermeability or an average obtained from several individuals, or a standard value or threshold established through experimentation using routine methods.

The level of Y34 in a sample can be determined using conventional techniques including, but not limited to, immunoassays such as enzyme-linked immunosorbent assays using an antibody specific for Y34, mass spectrometry, spectrophotometry, or a combination thereof. In the Examples below Y34 was detected using MALDI-TOF-TOF mass spectroscopy.

The methods of diagnosis can be coupled to a method of treatment, for example, the methods disclosed herein.

ii. Methods of Preventing PKG-1α Inhibition

PKG is a serine/threonine specific protein kinase that is activated upon the intracellular generation of 3',5' cyclic guanosine monophosphate (cGMP) by two main types of guanylyl cyclases (GC): soluble and membrane associated (Garbers, D. L., *Cell* 71, 1-4 (1992)). Soluble GC acts downstream of NO, while the membrane associated GC is activated through the extracellular binding of natriuretic peptides (NP). The mammalian genome encodes a type 1 PKG (Feil, S., et al., *Neuroscience* 135, 863-868 (2005)) and a type 2 PKG (Uhler, M. D. *The Journal of Biological*

Chemistry 268, 13586-13591 (1993); Vaandrager, et al., *Front Biosci.* 10, 2150-2164 (2005)). Both type 1 and 2 PKG are homodimeric proteins containing two identical polypeptide chains of approximately 76 kD and 85 kD, respectively. Alternative mRNA splicing of PKG-1 produces a type 1α PKG (7510) and a type 1β PKG (78 kD), which only share 36% identity in their first 70-100 amino-terminal residues (Wolfe, L., et al., *Current Opinion in Cell Biology* 1, 215-219 (1989); Wolfe, L., et al., *The Journal of biological chemistry* 264, 7734-7741 (1989)). PKG-1 has been detected at high concentrations in all types of vascular smooth muscle cells (VSMC) (Feil, S., et al., *Neuroscience* 135, 863-868 (2005)). PKG-2 has been detected in renal, adrenal, intestinal, pancreatic and brain cells but not in cardiac and vascular cells.

The primary sequence of PKG-1α is divided into two separate domains: a regulatory domain (aa 1-343) containing an amino-terminal region (aa 1-110) and two cGMP binding sites (aa 111-343) and a catalytic domain (aa 344-671) containing an ATP-binding site (aa 344-474) and the substrate-binding site (aa 475-671) (Takio, K., et al. *Biochemistry* 23, 4207-4218 (1984)). The aminoterminal region of the regulatory domain of PKG-1α contains a dimerization site, an autoinhibitory motif, and several autophosphorylation sites. The leucine zipper motif in the dimerization domain (aa 1-39) ensures substrate specificity of PKG-1α (Atkinson, R. A., et al., *Biochemistry* 30, 9387-9395 (1991)). The autoinhibitory region of PKG-1α (aa 58-72) binds to the catalytic domain and maintains the enzyme in an inhibited state. This auto-inhibition can be relieved by both cGMP binding and auto-phosphorylation which cause a conformational change (Zhao, J., et al., *The Journal of Biological Chemistry* 272, 31929-31936 (1997); Chu, D. M., et al., *The Journal of Biological Chemistry* 273, 14649-14656 (1998)), and disrupts the auto-inhibitory interaction of the regulatory and catalytic domains. Cyclic GMP increases both the hetero-phosphorylation and the auto-phosphorylation activity of PKG (Hofmann, F., et al., *FEBS Letters* 164, 350-354 (1983). The auto-phosphorylation of PKG-1α increases its cGMP-binding affinity and kinase activity (Hofmann, F., et al., *European Journal of Biochemistry/FEBS* 147, 361-365 (1985).

A hinge region connects the amino-terminal dimerization site with the two tandem cGMP binding sites: A (aa 111-227) and B (aa 228-343). These sites preferentially bind cGMP over cAMP with more than a 100-fold selectivity. The two cGMP binding sites of PKG have different binding characteristics Reed, R. B., et al., *The Journal of Biological Chemistry* 271, 17570-17575 (1996)); the amino-terminal high affinity site A and the succeeding low affinity site B display slow and fast cGMP-exchange characteristics, respectively (Hofmann, F., et al., *European Journal of Biochemistry/FEBS* 147, 361-365 (1985); Corbin, J. D., et al., *The Journal of Biological Chemistry* 258, 11391-11397 (1983)). The binding of cGMP to these sites activates the enzyme. The occupation of site B decreases the dissociation of cGMP from site A, and therefore, site A shows positive cooperativity (Hofmann, F., et al., *European Journal of Biochemistry/FEBS* 147, 361-365 (1985)). A maximally active enzyme is obtained when all four cGMP-binding sites of the dimeric kinase are occupied.

Tyrosine nitration is a selective process as not all tyrosine residues in a protein undergo nitration under patho-physiological conditions (Ischiropoulos, H., *Biochemical and Biophysical Research Communications* 305, 776-783 (2003)). PKG-1α has 21 tyrosine residues in its monomeric structure, of which 9 tyrosines are located in the regulatory domain and 12 are part of the catalytic domain. In vitro and in vivo studies have demonstrated that the nitration of cGMP-dependent protein kinase G-1α (PKG-1α) is an important posttranslational event responsible for the impaired PKG activity in the lungs of acute and chronic pulmonary hypertensive lambs (Aggarwal, S., et al., *Journal of Cellular Physiology* (2011)), mice with hypoxia-induced pulmonary hypertension (Negash, et al., *American Journal of Physiology* 293, L1012-1020 (2007)), and humans with idiopathic pulmonary arterial hypertension (Zhao, et al., *The Journal of Clinical Investigation* 119, 2009-2018 (2009)), however, the nature and location of this nitration along the PKG-1α was not known.

It has been discovered that Y247 and Y425 of PKG-1α can be nitrated and that nitration of tyrosine 247, located within the cGMP binding site B of the regulatory domain of PKG-1α, is responsible for the impaired kinase activity. Nitrative stress only decreased the cGMP dependent kinase activity, while basal PKG activity was unchanged. Therefore, the peptides and compositions thereof disclosed herein can be used to prevent or reduce nitration-mediated inhibition of PKG-1α.

Cyclic GMP binding to both sites A and B of PKG brings about a conformational change necessary for full kinase activity. The two cGMP binding sites share approximately 37% amino acid sequence similarity but differ in their cGMP binding kinetics (Corbin, J. D., et al., *The Journal of Biological Chemistry* 261, 1208-1214 (1986)). This difference may be due to the number of hydrogen bonds between cGMP and the cGMP binding sites on PKG as well as the length of these bonds (Kim, J. J., et al., *PloS One* 6, e18413). The Examples below show that molecular dynamic simulations using a full-length PKG-1α homology model indicated that the nitration of Y247 impairs hydrogen bonding between cGMP and the cGMP binding site B of the kinase. These results were confirmed by in vitro [$^3$H]cGMP binding studies and illustrate the mechanism by which PKG is believed to be regulated by nitrative stress. The Examples also show that a PKG-1α nitration shielding peptide binds to the region of PKG-1α surrounding Y247 and preserves PKG-Iα activity against peroyxnitrite.

The peptides and compositions disclosed herein can be used to reduce PKG-Iα nitration. Therefore, the peptides and compositions disclosed herein can be used to increase or prevent a decrease in PKG-Iα activity. More specifically, the peptide and compositions can be used to reduce or prevent a reduction in binding of cGMP to the enzyme and the associated impairment of the catalytic activity of PKG-1α resulting from nitration of Y247.

In a preferred embodiment, the composition includes one or more of the PKG-1α nitration shielding peptides or fusion proteins thereof disclosed above or in the Examples below. Without being bound by theory, the specific, exemplary PKG-1α nitration shielding peptide provide above and below are believed to prevented nitration of PKG-1α by shielding the protein from peroxynitrite attack. It is believed that the peptide provides blocks nitration of the Y247 and in some embodiments provides an antioxidant to react with peroxynitrite. The Examples below also show that PKG-1α nitration shielding pepetides can reduce LPS mediated PKG-1α nitration, and preserve barrier function without altering physiologic PKG-1α activity.

a. Methods of Maintaining Contractile-Like Phenotype in Smooth Muscle

In addition to its role in mediating the vasodilator effects of NO, PKG contributes to the maintenance of a contractile-like phenotype in SMC, and the suppression of PKG expression/activity in vitro induces a more synthetic, dedifferentiated phenotype (Lincoln, T., et al., *Acta Physiologica Scandinavica* 164, 507-515 (1998)). The Examples below show that exposure to the peroxynitrite generator, 3-morpholinosydnonimine N-ethylcarbamide (SIN-1) induced proliferation and metabolic activity in the PASMC expressing WT-PKG-1α but not in the cells transfected with the Y247F-PKG-1α mutant. Immunoblot analysis demonstrated that PASMC transfected with WT and Y247F-PKG-1α exhibited a contractile phenotype, as illustrated by the increased levels of the contractile markers: MYH and Calponin-1 and decreased levels of the proliferative marker, Vimentin. However, when exposed to SIN-1, WT-PKG-1α expressing PASMC acquired a more proliferative phenotype compared to the cells transfected with the Y247F-PKG-1α mutant. The Examples also show that the PASMC transfected with the WT- and the Y247F-PKG-1α were spindle shaped and had increased expression of contractile phenotype marker, SM22-α, bound to actin stress fibers. In contrast, the nuclear levels of the proliferative marker protein, PCNA, were decreased in these cells. SIN-1 treatment attenuated SM-22α expression and increased PCNA staining in the WT- but not in the Y247F-PKG-α expressing cells indicating that the Y247F-PKG-α mutant is resistant to phenotype modulation by nitrosative stress.

The PKG-1α nitration shielding peptides and compositions thereof disclosed herein can be used to reduce the effect of PKG-1α nitration on smooth muscle cells, particularly vascular smooth muscle cells. The peptides or compositions thereof can be administered in an amount effective to reduce or prevent nitration-dependent increase in proliferation or a phentotype thereof, or to reduce or prevent an increase in expression of a marker thereof (e.g., vimentin expression, or nuclear levels of protein PCNA); to reduce or prevent an increase in metabolic activity; to increase or reduce a decrease in expression of contractile markers such as MYH and Calponin-1; to increase or prevent a decrease a contractile phenotype (e.g., spinal shape morphology) or a marker thereof such as SM22-α, or localization thereof, for example to actin stress fibers; or any combination thereof.

b. Diseases to be Treated

The transition of vascular smooth muscle cells (VSMC) from a contractile to a proliferative phenotype appears to be an early event in various pathologies, such as pulmonary hypertension, atherosclerosis, and restenosis (Negash, S., et al., *American Journal of Physiology* 297, H304-312 (2009); Acampora, K. B., et al., *Annals of Vascular Surgery* 24, 116-126; Dusserre, E., et al., *Biochimica Et Biophysica Acta* 1212, 235-244 (1994)), and is associated with increased oxidative and nitrosative stress (Klemm, D. J., et al., *Journal of Cardiovascular Pharmacology* 58, 181-191; Madamanchi, N. R., et al., *Arteriosclerosis, Thrombosis, and Vascular Biology* 25, 950-956 (2005); Wang, J. N., et al., *Free Radical Biology & Medicine* 52, 173-181). ROS and RNS levels are increased in pulmonary hypertensive mice (Nisbet, R. E., et al., *American Journal of Respiratory Cell and Molecular Biology* 40, 601-609 (2009)), lambs (Aggarwal, S., et al., *Journal of Cellular Physiology* (2011)), and humans Zhao, et al., *The Journal of Clinical Investigation* 119, 2009-2018 (2009) and the increase in oxidative and nitrosative stress is implicated in both vasoconstriction) Broughton, B. R., et al., *American Journal of Physiology* 298, L232-242) and vascular remodeling (Nozik-Grayck, E., et al., *Advances in Experimental Medicine and Biology* 618, 101-112 (2007)).

The nitration and subsequent attenuation of PKG-1α catalytic activity appears to be an important pathological event underlying the development of vascular dysfunction in pulmonary hypertension and other vascular pathologies (Aggarwal, S., et al., *Journal of Cellular Physiology* (2011); Zhao, et al., *The Journal of Clinical Investigation* 119, 2009-2018 (2009); Herranz, B., et al., *Circulation Research* 110, 439-449). Studies have identified nitration and the ensuing attenuation of PKG-1α activity in the lungs of lambs with pulmonary hypertension secondary to increased pulmonary blood flow and in lambs with rebound pulmonary hypertension associated with the acute withdrawal of inhaled NO therapy (Aggarwal, S., et al., *Journal of Cellular Physiology* (2011)). In addition, the nitration and subsequent attenuation of PKG activity in the right ventricle (RV) appears to be responsible for the deterioration of RV function in a mouse model of PH induced by chronic hypoxia (Cruz, J. A., et al., *American Journal of Physiology* 302, H2518-2527). The increase in protein nitration associated with hypoxia reduces PKG activity through changes at the transcriptional and post-translational levels (Negash, et al., *American Journal of Physiology* 293, L1012-1020 (2007)). The clinical relevance of PKG nitration has also been shown by the observation that patients with idiopathic pulmonary arterial hypertension have increased PKG nitration in their lungs with no noticeable alteration in PKG protein levels (Zhao, et al., *The Journal of Clinical Investigation* 119, 2009-2018 (2009)). Thus, the accumulated data indicate that the nitration-dependent impairment of PKG activity may be a critical event in the development of vascular dysfunction in pulmonary hypertension.

The Examples below show that nitration of PKG-1α is increased following SIN-1 treatment; high levels of Y247 nitration can be detected in the peripheral lung tissue of lambs with pulmonary hypertension secondary to increased pulmonary blood flow and Y247 nitration is increased in the pulmonary vessels from patients suffering from idiopathic pulmonary hypertension compared to controls. Taken together the Examples indicate that the nitration of Y247 is an important mechanism by which nitrative stress impairment of PKG-1α activity both in vitro and in vivo.

Accordingly, the PKG-1α nitration shielding peptides and compositions thereof disclosed herein can be used to prevent or treat one or more symptoms or pathologies associated with pulmonary hypertension including idiopathic pulmonary arterial hypertension, atherosclerosis, restenosis, hypoxia, vasoconstriction, vascular remodeling, and other vascular dysfunctions.

Furthermore, increasing intracellular cGMP levels has been used as a management strategy in patients with multiple vascular abnormalities including inhaled NO therapy for pulmonary hypertension; NO donors, such as nitroglycerin, isosorbide dinitrate, or isosorbide mononitrate for coronary artery diseases; cGMP specific phosphodiesterase-5 inhibitors, sildenafil and tadalafil for the treatment of pulmonary hypertension and erectile dysfunction; and B-type natriuretic peptides for hypoxemic respiratory failure. The major goal of these therapies is to increase the production of cGMP or inhibit its breakdown and thereby increase vascular dilation. However, if the cellular levels of cGMP become too high this can interfere with normal cellular proliferation, cause DNA strand breaks, and/or base alterations that are potentially mutagenic (Weinberger, B., et al., *Toxicol. Sci.* 59, 5-16 (2001)).

Therefore, the disclosed PKG-1α nitration shielding peptides and compositions thereof can be used to treat coronary artery diseases, atherosclerosis, erectile dysfunction, and hypoxemic respiratory failure. In some embodiments, the disclosed PKG-1α nitration shielding peptides and compositions thereof are administered to the subject in combination with or as adjunct to traditional therapies: for example inhaled NO therapy for pulmonary hypertension, NO donors, such as nitroglycerin, isosorbide dinitrate, or isosorbide mononitrate for coronary artery diseases; cGMP specific phosphodiesterase-5 inhibitors, sildenafil and tadalafil for the treatment of pulmonary hypertension and erectile dysfunction; and B-type natriuretic peptides for hypoxemic respiratory failure.

Treatment strategies can also include cell or protein specific targeting of antioxidants, enhancing the autophosphorylation of PKG-1, or a combination thereof to further minimize the external requirement of cGMP for the enzyme activation.

B. Pharmaceutical Compositions and Methods of Administration

Pharmaceutical compositions including the disclosed nitration shielding peptides are also disclosed. Pharmaceutical compositions can be for administration by oral, parenteral (intramuscular, intraperitoneal, intravenous (IV) or subcutaneous injection), transdermal (either passively or using iontophoresis or electroporation), transmucosal (nasal, vaginal, rectal, or sublingual) routes of administration or using bioerodible inserts and can be formulated in unit dosage forms appropriate for each route of administration.

In a preferred embodiment, the compositions are formulated for and delivered to a mucosal surface such as that of the lungs. The composition can be administered prophylactically, therapeutically, or combinations thereof. Therefore, the composition can be administered during a period before, during, or after onset of protein nitration, or one or more symptoms of a pathology, disorder, or disorder associated therewith. In some embodiments, the composition is administered with one or more additional therapeutic agents as part of a co-therapy (e.g., a combination therapy including a nitration shielding peptide composition and one or more other therapeutic agents), one or more second treatments (e.g., an exercise regime, surgery, etc.), a or combinations thereof.

The composition and the additional therapeutic agent or treatment can be administered to the subject together or separately. The composition and the additional therapeutic agent or treatment can be administered on the same day, on a different days, or combinations thereof.

For example, the subject can be administered a disclosed composition 0, 1, 2, 3, 4, 5, or more days before administration of or exposure to the additional therapeutic agent or treatment. In some embodiments, the subject can be administered one or more doses of the composition every 1, 2, 3, 4, 5, 6 7, 14, 21, 28, 35, or 48 days prior to a first administration of or exposure to the additional therapeutic agent or treatment.

The subject can also be administered the composition for 0, 1, 2, 3, 4, 5, or more days after administration of or exposure to the additional therapeutic agent or treatment. The subject can also be administered the composition during administration of or exposure to the additional therapeutic agent or treatment. The subject can be administered one or more doses of the composition every 1, 2, 3, 4, 5, 6, 7, 14, 21, 28, 35, or 48 days during or after administration of the additional therapeutic agent or treatment.

1. Formulations

The nitration shielding peptides provided herein can be administered in a physiologically acceptable carrier to a host. Preferred methods of administration include systemic or local administration to the subject, or by direct administration to cells. The compositions can be administered to a cell or subject, as is generally known in the art for protein therapies.

The compositions can be combined in admixture with a pharmaceutically acceptable carrier vehicle. Therapeutic formulations are prepared for storage by mixing the active ingredient having the desired degree of purity with optional physiologically acceptable carriers, excipients or stabilizers (Remington's Pharmaceutical Sciences 17th edition, Osol, A. Ed. (198)), in the form of lyophilized formulations or aqueous solutions. Acceptable carriers, excipients or stabilizers are nontoxic to recipients at the dosages and concentrations employed, and include buffers such as phosphate, citrate and other organic acids; antioxidants including ascorbic acid; low molecular weight (less than about 10 residues) polypeptides; proteins, such as serum albumin, gelatin or immunoglobulins; hydrophilic polymers such as polyvinylpyrrolidone, amino acids such as glycine, glutamine, asparagine, arginine or lysine; monosaccharides, disaccharides and other carbohydrates including glucose, mannose, or dextrins; chelating agents such as EDTA; sugar alcohols such as mannitol or sorbitol; salt-forming counterions such as sodium; and/or nonionic surfactants such as Tween®, Pluronics® or PEG.

Pharmaceutical compositions may be prepared, packaged, or sold in a buccal formulation. Such formulations may be in the form of tablets, powders, aerosols, atomized solutions, suspensions, or lozenges made using known methods, and may contain from about 0.1% to about 20% (w/w) active ingredient with the balance of the formulation containing an orally dissolvable or degradable composition and/or one or more additional ingredients as described herein. Preferably, powdered or aerosolized formulations have an average particle or droplet size ranging from about 0.1 nanometers to about 200 nanometers when dispersed.

The composition can include one or more additional ingredients. As used herein, "additional ingredients" include: excipients, surface active agents, dispersing agents, inert diluents, granulating agents, disintegrating agents, binding agents, lubricating agents, sweetening agents, flavoring agents, coloring agents, preservatives, physiologically degradable compositions (e.g., gelatin), aqueous vehicles, aqueous solvents, oily vehicles and oily solvents, suspending agents, dispersing agents, wetting agents, emulsifying agents, demulcents, buffers, salts, thickening agents, fillers, emulsifying agents, antioxidants, antibiotics, antifungal agents, stabilizing agents, and pharmaceutically acceptable polymeric or hydrophobic materials. Other additional ingredients which may be included in the pharmaceutical compositions are known. Suitable additional ingredients are described in Remington's Pharmaceutical Sciences, $17^{th}$ ed. Mack Publishing Co., Genaro, ed., Easton, Pa. (1985).

Dosages and desired concentrations of the peptides disclosed herein in pharmaceutical compositions of the present disclosure may vary depending on the particular use envisioned. The determination of the appropriate dosage or route of administration is well within the skill of an ordinary physician. Animal experiments provide reliable guidance for the determination of effective doses for human therapy. Interspecies scaling of effective doses can be performed following the principles laid down by Mordenti, J. and Chappell, W. "The use of interspecies scaling in toxicokinetics" In Toxicokinetics and New Drug Development, Yacobi, et al., Eds., Pergamon Press, New York 1989, pp. 42-96. The composition can be administered intravenously in a wide dosing range from about 0.01 milligram per kilogram body weight (mg/kg) to about 10 mg/kg, alternatively about 0.01 milligram per kilogram body weight (mg/kg) to about 1.0 mg/kg, depending on patient's age and physical state, as well as dosing regimen and schedule.

The dose can be administered in separate administrations of 2, 3, 4, 5 or 6 doses. The dose can be administered every day, every two days, every three days, every four days, every five days, every six days, every seven days, once every two weeks, or once a month.

2. Polymeric Delivery Matrices

Either non-biodegradable or biodegradable matrices can be used for delivery of peptides. These can be natural or synthetic polymers, although synthetic polymers are preferred due to the better characterization of degradation and release profiles. The polymer can be selected based on the period over which release is desired or other factors based on the intended use. In some cases linear release may be most useful, although in others a pulse release or "bulk release" may provide more effective results. The polymer can be in the form of a hydrogel (typically in absorbing up to about 90% by weight of water), and can optionally be cross-linked with multivalent ions or polymers.

The peptide can be encapsulated within, dispersed in, associated with, or conjugated to microparticles, nanoparticles, etc. Unless specifically defined herein, microparticles, microspheres, and microcapsules are used interchangeably. The particles can be formed from one or more polymers, copolymers, or polymer blends. In some embodiments, the one or more polymers, copolymers, or polymer blends are biodegradable. Examples of suitable polymers include, but are not limited to, polyhydroxyacids such as poly(lactic acid), poly(glycolic acid), and poly(lactic acid-co-glycolic acids); polycaprolactones; poly(orthoesters); polyanhydrides; poly(phosphazenes); poly(hydroxyalkanoates); poly(lactide-co-caprolactones); polycarbonates such as tyrosine polycarbonates; polyamides (including synthetic and natural polyamides), polypeptides, and poly(amino acids); polyesteramides; polyesters; poly(dioxanones); poly(alkylene alkylates); hydrophobic polyethers; polyurethanes; polyetheresters; polyacetals; polycyanoacrylates; polyacrylates; polymethylmethacrylates; polysiloxanes; poly(oxyethylene)/poly(oxypropylene) copolymers; polyketals; polyphosphates; polyhydroxyvalerates; polyalkylene oxalates; polyalkylene succinates; poly(maleic acids), poly(alkylene glycols) such as polyethylene glycol (PEG), poly(propylene glycol) (PPG), and copolymers of ethylene glycol and propylene glycol, poly(oxyethylated polyol), poly(olefinic alcohol), polyvinylpyrrolidone), poly(hydroxy alkylmethacrylamide), poly(hydroxyalkylmethacrylate), poly(saccharides), poly(vinyl alcohol), as well as blends and copolymers thereof.

Controlled release polymeric devices can be made for long term release systemically following implantation of a polymeric device (rod, cylinder, film, disk) or injection (microparticles). The matrix can be in the form of microparticles such as microspheres, where peptides are dispersed within a solid polymeric matrix or microcapsules, where the core is of a different material than, the polymeric shell, and the peptide is dispersed or suspended in the core, which may be liquid or solid in nature. Alternatively, the polymer may be cast as a thin slab or film, ranging from nanometers to four centimeters, a powder produced by grinding or other standard techniques, or even a gel such as a hydrogel.

Techniques for preparing suitable polymeric particles are known in the art, and include solvent evaporation, hot melt particle formation, solvent removal, spray drying, phase inversion, coacervation, and low temperature casting. Bioerodible microspheres can be prepared using any of the methods developed for making microspheres for drug delivery, for example, as described by Mathiowitz and Langer, *J. Controlled Release* 5, 13-22 (1987); Mathiowitz, et al., *Reactive Polymers* 6, 275-283 (1987); and Mathiowitz, et al., *J. Appl. Polymer Sci.* 35, 755-774 (1988).

The devices can be formulated for local release to treat the area that is subject to a disease, which will typically deliver a dosage that is much less than the dosage for treatment of an entire body or systemic delivery. These can be implanted or injected subcutaneously, into the muscle, fat, or swallowed.

Controlled release polymeric devices can be made for long term release systemically following implantation of a polymeric device (rod, cylinder, film, disk) or injection (microparticles). The matrix can be in the form of microparticles such as microspheres, where peptides are dispersed within a solid polymeric matrix or microcapsules, where the core is of a different material than the polymeric shell, and the peptide is dispersed or suspended in the core, which may be liquid or solid in nature. Alternatively, the polymer may be cast as a thin slab or film, ranging from nanometers to four centimeters, a powder produced by grinding or other standard techniques, or even a gel such as a hydrogel.

In some cases, the peptides are covalently linked to the surface of the particles after particle formulation. In other cases, the peptides are non-covalently bound to the particle surface.

3. Parenteral Administration

The disclosed compositions can be administered parenterally. As used herein, "parenteral administration" is characterized by administering a pharmaceutical composition through a physical breach of a subject's tissue. Parenteral administration includes administering by injection, through a surgical incision, or through a tissue-penetrating non-surgical wound, and the like. In particular, parenteral administration includes subcutaneous, intraperitoneal, intravenous, intraarterial, intramuscular, intrasternal injection, and kidney dialytic infusion techniques.

Parenteral formulations can include the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Parenteral administration formulations include suspensions, solutions, emulsions in oily or aqueous vehicles, pastes, reconsitutable dry (e.g., powder or granular) formulations, and implantable sustained-release or biodegradable formulations. Such formulations may also include one or more additional ingredients including suspending, stabilizing, or dispersing agents. Parenteral formulations may be prepared, packaged, or sold in the form of a sterile injectable aqueous or oily suspension or solution. Parenteral formulations may also include dispersing agents, wetting agents, or suspending agents described herein. Methods for preparing these types of formulations are known. Sterile injectable formulations may be prepared using non-toxic parenterally-acceptable diluents or solvents, such as water, 1,3-butane diol, Ringer's solution, isotonic sodium chloride solution, and fixed oils such as synthetic monoglycerides or diglycerides. Other parentally-administrable formulations include microcrystalline forms, liposomal preparations, and biodegradable polymer systems. Compositions for sustained release or implantation may include pharmaceutically acceptable polymeric or hydrophobic materials such as emulsions, ion exchange resins, sparingly soluble polymers, and sparingly soluble salts.

4. Enteral Administration

The peptides can be formulated for oral delivery.

a. Additives for Oral Administration

Oral solid dosage forms are described generally in Remington's Pharmaceutical Sciences, 18th Ed. 1990 (Mack Publishing Co. Easton Pa. 18042) at Chapter 89. Solid dosage forms include tablets, capsules, pills, troches or lozenges, cachets, pellets, powders, or granules or incorporation of the material into particulate preparations of polymeric compounds such as polylactic acid, polyglycolic acid, etc. or into liposomes. Such compositions may influence the physical state, stability, rate of in vivo release, and rate of in vivo clearance of the present active compounds and derivatives. See, e.g., Remington's Pharmaceutical Sciences, 18th Ed. (1990, Mack Publishing Co., Easton, Pa. 18042) pages 1435-1712, which are herein incorporated by reference. The compositions may be prepared in liquid form, or may be in dried powder (e.g., lyophilized) form. Liposomal or proteinoid encapsulation may be used to formulate the compositions (as, for example, proteinoid microspheres reported in U.S. Pat. No. 4,925,673). Liposomal encapsulation may be used and the liposomes may be derivatized with various polymers (e.g., U.S. Pat. No. 5,013,556). See also Marshall, K. In: Modern Pharmaceutics Edited by G. S. Banker and C. T. Rhodes Chapter 10, 1979. In general, the formulation will include the compound (or chemically modified forms thereof) and inert ingredients which protect the compound in the stomach environment, and release of the biologically active material in the intestine.

Another embodiment provides liquid dosage forms for oral administration, including pharmaceutically acceptable emulsions, solutions, suspensions, and syrups, which may contain other components including inert diluents; adjuvants such as wetting agents, emulsifying and suspending agents; and sweetening, flavoring, and perfuming agents.

Controlled release oral formulations may be desirable. Peptides can be incorporated into an inert matrix which permits release by either diffusion or leaching mechanisms, e.g., gums. Slowly degenerating matrices may also be incorporated into the formulation. Another form of a controlled release is based on the Oros therapeutic system (Alza Corp.), i.e., the drug is enclosed in a semipermeable membrane which allows water to enter and push drug out through a single small opening due to osmotic effects. For oral formulations, the location of release may be the stomach, the small intestine (the duodenum, the jejunum, or the ileum), or the large intestine. Preferably, the release will avoid the deleterious effects of the stomach environment, either by protection of the active agent (or derivative) or by release of the active agent (or derivative) beyond the stomach environment, such as in the intestine. To ensure full gastric resistance a coating impermeable to at least pH 5.0 is essential. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D, Aquateric, cellulose acetate phthalate (CAP), Eudragit L, Eudragit S, and Shellac. These coatings may be used as mixed films.

b. Chemically Modified Forms for Oral Dosage

Peptides can be chemically modified so that oral delivery of the derivative is efficacious. Generally, the chemical modification contemplated is the attachment of at least one moiety to the component molecule itself, where said moiety permits (a) inhibition of proteolysis; and (b) uptake into the blood stream from the stomach or intestine. Also desired is the increase in overall stability of the component or components and increase in circulation time in the body. PEGylation is a preferred chemical modification for pharmaceutical usage. Other moieties that may be used include: propylene glycol, copolymers of ethylene glycol and propylene glycol, carboxymethyl cellulose, dextran, polyvinyl alcohol, polyvinyl pyrrolidone, polyproline, poly-1,3-dioxolane and poly-1,3,6-tioxocane (see, e.g., Abuchowski and Davis (1981) "Soluble Polymer-Enzyme Adducts," in Enzymes as Drugs. Hocenberg and Roberts, eds. (Wiley-Interscience: New York, N.Y.) pp. 367-383; and Newmark, et al., (1982) *J. Appl. Biochem.* 4:185-189).

5. Mucosal Delivery

Formulations for administration to a mucosal surface are also disclosed. Pharmaceutical formulations and methods for the pulmonary administration of active agents to subjects are known in the art.

The respiratory tract is the structure involved in the exchange of gases between the atmosphere and the blood stream. The respiratory tract encompasses the upper airways, including the oropharynx and larynx, followed by the lower airways, which include the trachea followed by bifurcations into the bronchi and bronchioli. The upper and lower airways are called the conducting airways. The terminal bronchioli then divide into respiratory bronchioli which then lead to the ultimate respiratory zone, the alveoli, or deep lung, where the exchange of gases occurs.

Formulations can be divided into dry powder formulations and liquid formulations. Both dry powder and liquid formulations can be used to form aerosol formulations. The term aerosol as used herein refers to any preparation of a fine mist of particles, which can be in solution or a suspension, whether or not it is produced using a propellant.

a. Dry Powder Formulations

Dry powder formulations are finely divided solid formulations containing peptides and compositions thereof which are suitable for pulmonary administration. Dry powder formulations include, at a minimum, one or more peptides which are suitable for pulmonary administration. Such dry powder formulations can be administered via pulmonary inhalation to a patient without the benefit of any carrier, other than air or a suitable propellant. In other embodiments, the dry powder formulations contain one or more peptides in combination with a pharmaceutically acceptable carrier. In these embodiments, the peptide and pharmaceutical carrier can be formed into nanoparticles- or microparticles for delivery to the lung.

The pharmaceutical carrier may include a bulking agent or a lipid or surfactant. Natural surfactants such as dipalmitoylphosphatidylcholine (DPPC) are the most preferred. Synthetic and animal derived pulmonary surfactants include:

Synthetic Pulmonary Surfactants

Exemplary synthetic pulmonary surfactants and compositions thereof include, but are not limited to:

Exosurf—a mixture of DPPC with hexadecanol and tyloxapol added as spreading agents.

Pumactant (Artificial Lung Expanding Compound or ALEC)—a mixture of DPPC and PG.

KL-4—composed of DPPC, palmitoyl-oleoyl phosphatidylglycerol, and palmitic acid, combined with a 21 amino acid synthetic peptide that mimics the structural characteristics of SP-B.

Venticute—DPPC, PG, palmitic acid and recombinant SP-C.

Animal Derived Surfactants

Exemplary animal derived surfactants and compositions thereof include, but are not limited to:

Alveofact—extracted from cow lung lavage fluid

Curosurf—extracted from material derived from minced pig lung

Infasurf—extracted from calf lung lavage fluid

Survanta—extracted from minced cow lung with additional DPPC, palmitic acid and tripalmitin Exosurf, Curosurf, Infasurf, and Survanta are the surfactants currently FDA approved for use in the U.S.

The pharmaceutical carrier may also include one or more stabilizing agents or dispersing agents. The pharmaceutical carrier may also include one or more pH adjusters or buffers. Suitable buffers include organic salts prepared from organic acids and bases, such as sodium citrate or sodium ascorbate. The pharmaceutical carrier may also include one or more salts, such as sodium chloride or potassium chloride.

Dry powder formulations are typically prepared by blending one or more peptides with one or more pharmaceutically acceptable carriers. Optionally, additional active agents may be incorporated into the mixture as discussed below. The mixture is then formed into particles suitable for pulmonary administration using techniques known in the art, such as lyophilization, spray drying, agglomeration, spray coating, coacervation, low temperature casting, milling (e.g., air-attrition milling (jet milling), ball milling), high pressure homogenization, and/or supercritical fluid crystallization.

An appropriate method of particle formation can be selected based on the desired particle size, particle size distribution, and particle morphology desired for the formulation. In some cases, the method of particle formation is selected so as to produce a population of particles with the desired particle size, particle size distribution for pulmonary administration. Alternatively, the method of particle formation can produce a population of particles from which a population of particles with the desired particle size, particle size distribution for pulmonary administration is isolated, for example by sieving.

It is known in the art that particle morphology affects the depth of penetration of a particle into the lung. Accordingly, dry powder formulations is processed into particles having the appropriate mass median aerodynamic diameter (MMAD), tap density, and surface roughness to achieve delivery of the one or more active agents to the desired region(s) of the lung. For example, preferred particle morphologies for delivery to the deep king are known in the art, and are described, for example, in U.S. Pat. No. 7,052,678 to Vanbever, et al.

Particles having a mass median aerodynamic diameter (MMAD) of greater than about 5 microns generally do not reach the lung; instead, they tend to impact the back of the throat and are swallowed. Particles having diameters of about 3 to about 5 microns are small enough to reach the upper- to mid-pulmonary region (conducting airways), but may be too large to reach the alveoli. Smaller particles, (i.e., about 0.5 to about 3 microns), are capable of efficiently reaching the alveolar region. Particles having diameters smaller than about 0.5 microns can also be deposited in the alveolar region by sedimentation. The precise particle size range effective to achieve delivery to the alveolar region will depend on several factors, including the tap density of particles being delivered. Generally speaking, as tap density decreases, the MMAD of particles capable of efficiently reaching the alveolar region of the lungs increases. Therefore, in cases of particles with low tap densities, particles having diameters of about 3 to about 5 microns, about 5 to about 7 microns, or about 7 to about 9.5 microns can be efficiently delivered to the lungs. The preferred aerodyanamic diameter for maximum deposition within the lungs can be calculated. See, for example, U.S. Pat. No. 7,052,678 to Vanbever, et al. Microparticles cannot diffuse through mucus even if their surface is muco-resistant. However, peptides can be encapsulated in microparticles to impact upper lung, and subsequently release peptides. In some embodiments, the dry powder formulation is composed of a plurality of particles having a median mass aerodynamic diameter between about 0.05 to about 10 microns, more preferably between about 0.05 microns to about 7 microns, most preferably between about 0.05 to about 5 microns. In some embodiments, the dry powder formulation is composed of a plurality of particles having a median mass aerodynamic diameter between about 0.05 microns to about 3 microns, more preferably between about 0.05 microns to about 1 micron, more preferably between about 0.05 microns to about 0.7 microns. In some embodiments, the dry powder formulation is composed of a plurality of particles having a median mass aerodynamic diameter between about 3 to about 5 microns. In some embodiments, the dry powder formulation is composed of a plurality of particles having a median mass aerodynamic diameter between about 5 to about 7 microns. In some embodiments, the dry powder formulation is composed of a plurality of particles having a median mass aerodynamic diameter between about 7 to about 9.5 microns.

In some cases, there may be an advantage to delivering particles larger than about 3 microns in diameter. Phagocytosis of particles by alveolar macrophages diminishes precipitously as particle diameter increases beyond about 3 microns. Kawaguchi, H., et al., *Biomaterials* 7: 61-66 (1986); Krenis, L. J. and Strauss, B., Proc. Soc. Exp. Med., 107: 748-750 (1961); and Rudt, S. and Muller, R. H., *J. Contr. Rel.*, 22: 263-272 (1992). By administering particles with an aerodynamic volume greater than 3 microns, phagocytic engulfment by alveolar macrophages and clearance from the lungs can be minimized. In some embodiments, at least about 80%, more preferably at least about 90%, most preferably at least about 95% of the particles in dry powder formulation have aerodynamic diameter of less than about 10 microns, more preferably less than about 7 microns, most preferably about 5 microns. In some embodiments, at least about 80%, more preferably at least about 90%, most preferably at least about 95% of the particles in dry powder formulation have aerodynamic diameter of greater than about 0.03 microns.

In some embodiments, at least about 80%, more preferably at least about 90%, most preferably at least about 95% of the particles in dry powder formulation have aerodynamic diameter of greater than about 0.03 microns and less than about 10 microns, more preferably greater than about 0.03 microns and less than about 7 microns, most preferably greater than about 0.03 microns and less than about 5 microns. In some embodiments, at least about 80%, more preferably at least about 90%, most preferably at least about 95% of the particles in dry powder formulation have aerodynamic diameter of greater than about 0.03 microns and less than about 3 microns. In some embodiments, at least about 80%, more preferably at least about 90%, most preferably at least about 95% of the particles in dry powder formulation have aerodynamic diameter of greater than about 0.03 microns and less than about 5 microns. In some embodiments, at least about 80%, more preferably at least about 90%, most preferably at least about 95% of the particles in dry powder formulation have aerodynamic diameter of greater than about 0.03 microns and less than about 7 microns. In some embodiments, at least about 80%, more preferably at least about 90%, most preferably at least about 95% of the particles in dry powder formulation have aerodynamic diameter of greater than about 0.03 microns and less than about 9.5 microns.

In some embodiments, the particles have a tap density of less than about 0.4 g/cm$^3$, more preferably less than about 0.25 g/cm$^3$, most preferably less than about 0.1 g/cm$^3$. Features which can contribute to low tap density include irregular surface texture and porous structure.

In some cases, the particles are spherical or ovoid in shape. The particles can have a smooth or rough surface texture. The particles may also be coated with a polymer or other suitable material to control release of one or more active agents in the lungs.

Dry powder formulations can be administered as dry powder using suitable methods known in the art. Alternatively, the dry powder formulations can be suspended in the liquid formulations described below, and administered to the lung using methods known in the art for the delivery of liquid formulations.

b. Liquid Formulations

Liquid formulations contain one or more peptides or a composition thereof (e.g., a composition including one or more nitration shielding peptides packaged in or associated with a micro or nanoparticle) suspended in a liquid pharmaceutical carrier.

Suitable liquid carriers include, but are not limited to distilled water, de-ionized water, pure or ultrapure water, saline, and other physiologically acceptable aqueous solutions containing salts and/or buffers, such as phosphate buffered saline (PBS), Ringer's solution, and isotonic sodium chloride, or any other aqueous solution acceptable for administration to an animal or human. Preferably, liquid formulations are isotonic relative to physiological fluids and of approximately the same pH, ranging e.g., from about pH 4.0 to about pH 7.4, more preferably from about pH 6.0 to pH 7.0. The liquid pharmaceutical carrier can include one or more physiologically compatible buffers, such as a phosphate buffers. One skilled in the art can readily determine a suitable saline content and pH for an aqueous solution for pulmonary administration.

Liquid formulations may include one or more suspending agents, such as cellulose derivatives, sodium alginate, polyvinylpyrrolidone, gum tragacanth, or lecithin. Liquid formulations may also include one or more preservatives, such as ethyl or n-propyl p-hydroxybenzoate.

In some cases the liquid formulation may contain one or more solvents that are low toxicity organic (i.e., nonaqueous) class 3 residual solvents, such as ethanol, acetone, ethyl acetate, tetrahydrofuran, ethyl ether, and propanol. These solvents can be selected based on their ability to readily aerosolize the formulation. Any such solvent included in the liquid formulation should not detrimentally react with the one or more active agents present in the liquid formulation. The solvent should be sufficiently volatile to enable formation of an aerosol of the solution or suspension. Additional solvents or aerosolizing agents, such as a freon, alcohol, glycol, polyglycol, or fatty acid, can also be included in the liquid formulation as desired to increase the volatility and/or alter the aerosolizing behavior of the solution or suspension.

Liquid formulations may also contain minor amounts of polymers, surfactants, or other excipients well known to those of the art. In this context, "minor amounts" means no excipients are present that might adversely affect uptake of the one or more active agents in the lungs.

c. Aerosol Formulations

The dry powder and liquid formulations described above can be used to form aerosol formulations for pulmonary administration. Aerosols for the delivery of therapeutic agents to the respiratory tract are known in the art. The term aerosol as used herein refers to any preparation of a fine mist of solid or liquid particles suspended in a gas. In some cases, the gas may be a propellant; however, this is not required. Aerosols may be produced using a number of standard techniques, including as ultrasonication or high pressure treatment. Preferably, a dry powder or liquid formulation as described above is formulated into aerosol formulations using one or more propellants. Suitable propellants include air, hydrocarbons, such as pentane, isopentane, butane, isobutane, propane and ethane, carbon dioxide, chlorofluorocarbons, fluorocarbons, and combinations thereof. Suitable fluorocarbons include 1-6 hydrogen containing fluorocarbons, such as $CHF_2CHF_2$, $CF_3CH_2F$, $CH_2F_2CH_3$, and $CF_3CHFCF_3$ as well as fluorinated ethers such as $CF_3$—O—$CF_3$, $CF_2H$—O—$CHF_2$, and $CF_3$—$CF_2$-β-$CF_2$—$CH_3$. Suitable fluorocarbons also include perfluorocarbons, such as 1-4 carbon perfluorocarbons including $CF_3CF_3$, $CF_3CF_2CF_3$, and $CF_3CF_2CF_2CF_3$. Preferably, the propellants include, but not limited to, one or more hydrofluoroalkanes (HFA). Suitable HFA propellants, include but are not limited to, 1,1,1,2,3,3,-heptafluoro-n-propane (HFA 227), 1,1,1,2-tetrafluoroethane (HFA 134) 1,1,1,2,25 3,3,3-heptafluoropropane (Propellant 227), or any mixture of these propellants.

Preferably, the one or more propellants have sufficient vapor pressure to render them effective as propellants. Preferably, the one or more propellants are selected so that the density of the mixture is matched to the density of the particles in the aerosol formulation in order to minimize settling or creaming of the particles in the aerosol formulation. The propellant is preferably present in an amount sufficient to propel a plurality of the selected doses of the aerosol formulation from an aerosol canister.

d. Methods of Mucosal Administration

Mucosal formulations can be administered to any mucosal surface. Generally, the formulations are administered to the pulmonary tract. Aerosolized pharmaceutical formulations can be delivered to the lungs, preferably using one of the device described below.

Liquid formulations can also be administered to the respiratory tract by other suitable methods such as intranasal instillation, intratracheal installation, and intratracheal injection.

In some cases, the one or more active agents are delivered into the lungs by inhalation of an aerosolized pharmaceutical formulation. Inhalation can occur through the nose and/or the mouth of the patient. Administration can occur by self-administration of the formulation while inhaling, or by administration of the formulation via a respirator to a patient on a respirator.

In some cases, a device is used to administer the formulations to the lungs. Suitable devices include, but are not limited to, dry powder inhalers, pressurized metered dose inhalers, nebulizers, and electrohydrodynamic aerosol devices.

i. Dry Powder Inhalers

The dry powder formulations described above can be administered to the lungs of a patient using a dry powder inhaler (DPI). DPI devices typically use a mechanism such as a burst of gas to create a cloud of dry powder inside a container, which can then be inhaled by the patient.

In a dry powder inhaler, the dose to be administered is stored in the form of a non-pressurized dry powder and, on actuation of the inhaler, the particles of the powder are inhaled by the subject. In some cases, a compressed gas (i.e., propellant) may be used to dispense the powder, similar to pressurized metered dose inhalers (pMDIs). In some cases, the DPI may be breath actuated, meaning that an aerosol is created in precise response to inspiration. Typically, dry powder inhalers administer a dose of less than a few tens of milligrams per inhalation to avoid provocation of cough.

DPIs function via a variety of mechanical means to administer formulations to the lungs. In some DPIs, a doctor blade or shutter slides across the dry powder formulation contained in a reservoir, culling the formulation into a flowpath whereby the patient can inhale the powder in a single breath. In other DPIs, the dry powder formulation is packaged in a preformed dosage form, such as a blister, tabule, tablet, or gelcap, which is pierced, crushed, or otherwise unsealed to release the dry powder formulation into a flowpath for subsequent inhalation. Still others DPIs release the dry powder formulation into a chamber or capsule and use mechanical or electrical agitators to keep the dry powder formulation suspended in the air until the patient inhales.

Dry powder formulations may be packaged in various forms, such as a loose powder, cake, or pressed shape for insertion in to the reservoir of a DPI. Examples suitable DPIs for the administration of the formulations described above include the Turbohaler® inhaler (Astrazeneca, Wilmington, Del.), the Clickhaler® inhaler (Innovata, Ruddington, Nottingham, UK), the Diskus® inhaler (Glaxo, Greenford, Middlesex, UK), the EasyHaler® (Orion, Expoo, FI), the Exubera® inhaler (Pfizer, New York, N.Y.), the Qdose® inhaler (Microdose, Monmouth Junction, N.J.), and the Spiros® inhaler (Dura, San Diego, Calif.).

ii. Pressurized Metered Dose Inhalers

The liquid formulations described above can be administered to the lungs of a patient using a pressurized metered dose inhaler (pMDI).

Pressurized Metered Dose Inhalers (pMDIs) generally include at least two components: a canister in which the liquid formulation is held under pressure in combination with one or more propellants, and a receptacle used to hold and actuate the canister. The canister may contain a single or multiple doses of the formulation. The canister may include a valve, typically a metering valve, from which the contents of the canister may be discharged. Aerosolized drug is dispensed from the pMDI by applying a force on the canister to push it into the receptacle, thereby opening the valve and causing the drug particles to be conveyed from the valve through the receptacle outlet. Upon discharge from the canister, the liquid formulation is atomized, forming an aerosol.

pMDIs typically employ one or more propellants to pressurize the contents of the canister and to propel the liquid formulation out of the receptacle outlet, forming an aerosol. Any suitable propellants, including those discussed above, may be utilized. The propellant may take a variety of forms. For example, the propellant may be a compressed gas or a liquefied gas. Chlorofluorocarbons (CFC) were once commonly used as liquid propellants, but have now been banned. They have been replaced by the now widely accepted hydrofluororalkane (HFA) propellants.

pMDIs are available from a number of suppliers, including 3M Corporation, Aventis, Boehringer Ingleheim, Forest Laboratories, Glaxo-Wellcome, Schering Plough and Vectura. In some cases, the patient administers an aerosolized formulation by manually discharging the aerosolized formulation from the pMDI in coordination with inspiration. In this way, the aerosolized formulation is entrained within the inspiratory air flow and conveyed to the lungs.

In other cases, a breath-actuated trigger, such as that included in the Tempo® inhaler (MAP Pharmaceuticals, Mountain View, Calif.) may be employed that simultaneously discharges a dose of the formulation upon sensing inhalation. These devices, which discharge the aerosol formulation when the user begins to inhale, are known as breath-actuated pressurized metered dose inhalers (baMDIs).

iii. Nebulizers

The liquid formulations described above can also be administered using a nebulizer. Nebulizers are liquid aerosol generators that convert the liquid formulation described able, usually aqueous-based compositions, into mists or clouds of small droplets, preferably having diameters less than 5 microns mass median aerodynamic diameter, which can be inhaled into the lower respiratory tract. This process is called atomization. The droplets carry the one or more active agents into the nose, upper airways or deep lungs when the aerosol cloud is inhaled. Any type of nebulizer may be used to administer the formulation to a patient, including, but not limited to pneumatic (jet) nebulizers and electromechanical nebulizers.

Pneumatic (jet) nebulizers use a pressurized gas supply as a driving force for atomization of the liquid formulation. Compressed gas is delivered through a nozzle or jet to create a low pressure field which entrains a surrounding liquid formulation and shears it into a thin film or filaments. The film or filaments are unstable and break up into small droplets that are carried by the compressed gas flow into the inspiratory breath. Baffles inserted into the droplet plume screen out the larger droplets and return them to the bulk liquid reservoir. Examples of pneumatic nebulizers include, but are not limited to, PART LC Plus®, PARI LC Sprint®, Devilbiss PulmoAide®, and Boehringer Ingleheim Respima®. Electromechanical nebulizers use electrically generated mechanical force to atomize liquid formulations. The electromechanical driving force can be applied, for example, by vibrating the liquid formulation at ultrasonic frequencies, or by forcing the bulk liquid through small holes in a thin film. The forces generate thin liquid films or filament streams which break up into small droplets to form a slow moving aerosol stream which can be entrained in an inspiratory flow.

In some cases, the electromechanical nebulizer is an ultrasonic nebulizer, in which the liquid formulation is coupled to a vibrator oscillating at frequencies in the ultrasonic range. The coupling is achieved by placing the liquid in direct contact with the vibrator such as a plate or ring in a holding cup, or by placing large droplets on a solid vibrating projector (a horn). The vibrations generate circular standing films which break up into droplets at their edges to atomize the liquid formulation. Examples of ultrasonic nebulizers include DuroMist®, Drive Medical Beetle Neb®, Octive Tech Densylogic®, and John Bunn Nano-Sonic®. In some cases, the electromechanical nebulizer is a mesh nebulizer, in which the liquid formulation is driven through a mesh or membrane with small holes ranging from 2 to 8 microns in diameter, to generate thin filaments which break up into small droplets. In certain designs, the liquid formulation is forced through the mesh by applying pressure with a solenoid piston driver (for example, the AERx® nebulizer), or by sandwiching the liquid between a piezoelectrically vibrated plate and the mesh, which results in a oscillatory pumping action (for example EFlow®, AerovectRx®, or TouchSpray® nebulizer). In other cases, the mesh vibrates back and forth through a standing column of the liquid to pump it through the holes. Examples of such nebilzers include the AeroNeb Go®, AeroNeb Pro®. PARI EFlow®, Omron 22UE®; and Aradigm AERx®.

iv. Electrohydrodynamic Aerosol Devices

The liquid formulations described above can also be administered using an electrohydrodynamic (EHD) aerosol device. EHD aerosol devices use electrical energy to aerosolize liquid drug solutions or suspensions. Examples of EHD aerosol devices are known in the art. See, for example, U.S. Pat. No. 4,765,539 to Noakes, et al. and U.S. Pat. No. 4,962,885 to Coffee, R. A. The electrochemical properties of the formulation may be important parameters to optimize when delivering the liquid formulation to the lung with an EHD aerosol device and such optimization is routinely performed by one of skill in the art.

EXAMPLES

Example 1

Endothelial NOS Contributes to the LPS Mediated Barrier Dysfunction in HLMVEC

Materials and Methods

Isolation of Human Lung Microvascular Endothelial Cells

Isolation and culture of human lung microvascular endothelial cells (HLMVEC) was performed as described previously (Catravas, J. D., et al., *Vascul. Pharmacol.* 52, 175-181 (2010)).

Endothelial Monolayer Resistance Determinations

The electrical resistance of the endothelial cell monolayer was measured with the electrical cell impedance sensor (ECIS) technique. In this system, the cells are cultured on gold plated electrodes. The change in resistance across the monolayer is measured through an amplifier attached to the arrays. Each study was performed when the resistance reached a plateau. The data was normalized to the initial voltage and plotted as a normalized resistance.

Western Blot Analysis

HLMVEC were lysed and centrifuged at 6,000×g and the supernatant collected as previously described (Sud, N., et al., *Am. J. Physiol. Lung Cell Mol. Physiol.* 293, L1444-1453 (2007); Sharma, S., et al., *Am. J. Physiol. Lung Cell Mol. Physiol.* 294, L46-56 (2008)). Cell extracts were separated on 4-20% gels and electrophoretically transferred to PVDF membrane (Bio-Rad), then blocked with 5% nonfat dry milk in Tris-buffered saline. The membranes were probed with antibodies to RhoA (Cell Signaling), eNOS (BD), iNOS (Cell Signaling), or 3-Nitrotyrosine (Calbiochem). Reactive bands were visualized using chemi-luminescence (Pierce) on a Kodak 440CF image station. Band intensity was quantified using Kodak 1D image processing software. Protein loading was normalized by re-probing with mouse anti-β-actin.

Results

To examine if protein nitration by peroxynitrite is a contributing factor in endothelial barrier disruption in response to LPS, transendothelial resistance (TER) was measured in HLMVEC in the presence or absence of the peroxynitrite scavenger, MnTmPyp. HLMVEC were challenged with LPS (1 EU/ml) in the presence or absence of the peroxynitrite scavenger, MnTMPyP (25 μM).

Normalized transendothelial resistance (TER) decreased in response to LPS. Decreased TER was attenuated in the presence of MnTMPyP (FIG. 1A). MnTMPyP pre-treatment significantly attenuated the barrier disruption associated with LPS treatment (FIG. 1A).

Figure 1B:
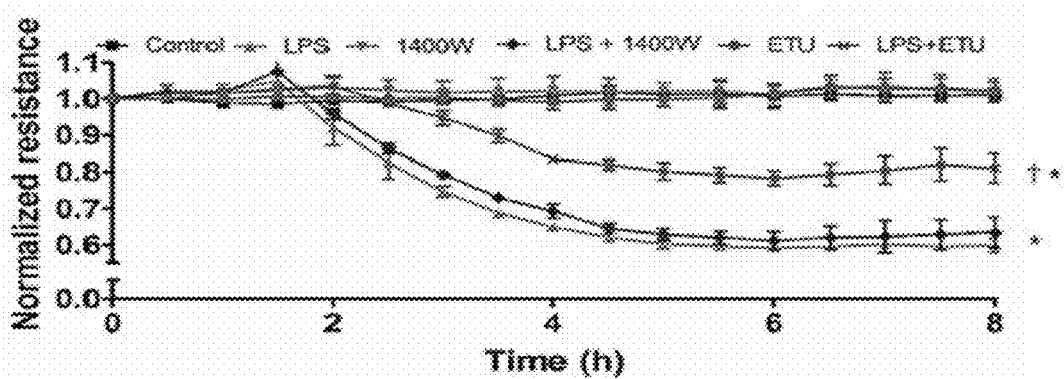
Figure 1C:
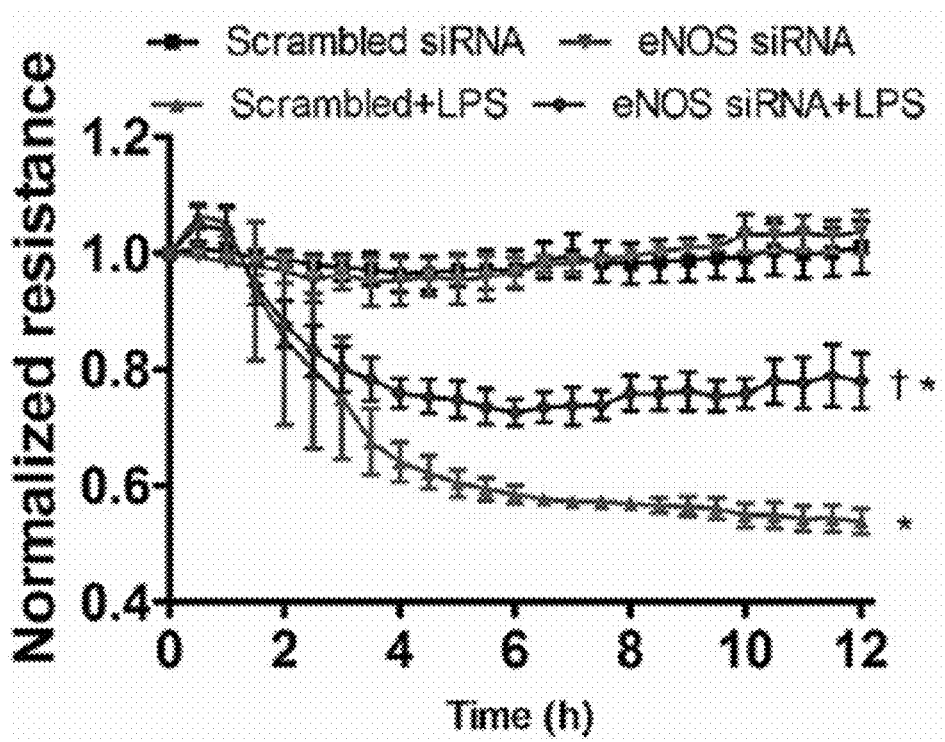

To evaluate the role played by NOS in the barrier dysfunction, HLMVEC were exposed to LPS in the presence or absence of ETU (a non-specific NOS inhibitor) or 1400W (to inhibit iNOS). HLMVEC were challenged with LPS (1 EU/ml) in the presence or absence of the general NOS inhibitor, ETU (200 μM) or the iNOS specific inhibitor, 1400W (100 μM). The LPS-mediated decrease in TER was attenuated in the presence of ETU, but not 1400W (FIG. 1B). The important role of eNOS was then confirmed using a siRNA approach. HLMVEC were transiently transfected with a siRNA against eNOS or a scrambled control siRNA. After 48 h, there was a significant knockdown of eNOS protein levels (50%), as determined by Western blotting. Reducing eNOS protein levels preserved HLMVEC barrier function when challenged with LPS (FIG. 1C).

In conclusion, ETU, but not 1400W markedly attenuated the LPS mediated barrier disruption in HLMVEC. The decrease in eNOS protein attenuated the LPS-mediated decrease in TER.

Example 2

LPS Increases RhoA Activity Through the Nitration of Tyrosine 34 (Y34)

Materials and Methods

Analysis of RhoA Activity

RhoA activity levels were measured using the Rhotekin Rho Binding Domain (RBD) pull-down assay. Briefly, 2×10$^6$ cells were seeded in 10 cm dishes and incubated overnight in DMEM with 10% FBS and 5% antibiotics. The cells were then pretreated with the peroxynitrite scavenger, MynTMPyp (25 μM), for 30 min. The cells were treated with LPS (1 EU/ml) for 4 h. The level of active RhoA pulled down by the assay was measured by Western blot analysis (see above).

Immunoprecipitation Analysis

HLMVEC were homogenized in IP buffer (25 mM Hepes, pH 7.5, 150 mM NaCl, 1% NP-40, 10 mM MgCl$_2$, 1 mM EDTA, 2% glycerol supplemented with protease inhibitors). To precipitate the bound protein, 10 μl of a protein A/G agarose suspension (EMD/Calbiochem) was added for 2 h at 4° C. The samples were then centrifuged at 14,000 rpm for 5 min, the supernatant removed, and the beads washed 3× with IP buffer. Twenty μl of 2× Laemmli buffer was added, the samples were boiled for 5 min, and analyzed as described above. Immunoprecipitation efficiency was normalized by re-probing with RhoA.

MALDI-TOF-TOF Mass Spectrometry

All spectra were taken on an ABSciex 5800 MALDI-TOF-TOF mass spectrometer in positive reflector mode (10 kV) with a matrix of CHCA. Masses were calibrated to known peptide standards. 5 μl aliquots of the RhoA chymotrypsin/trypsin digest were cleaned on a C18 ZipTip (Millipore). Bound peptides were desalted and then eluted with 2.5 μl of acidic acetonitrile (75% CH3CN, 0.1% TFA). The eluent was mixed with 2.5 μl of freshly prepared CHCA stock solution (20 mg/ml CHCA), and 1.5 μl portions of this mixture were spotted onto a MALDI sample plate for air-drying. Peptide coverage of 93% was achieved for the RhoA sequence and only the C-terminus peptide corresponding to amino acids 180-193 was not found in the MS.

Figure 2A:
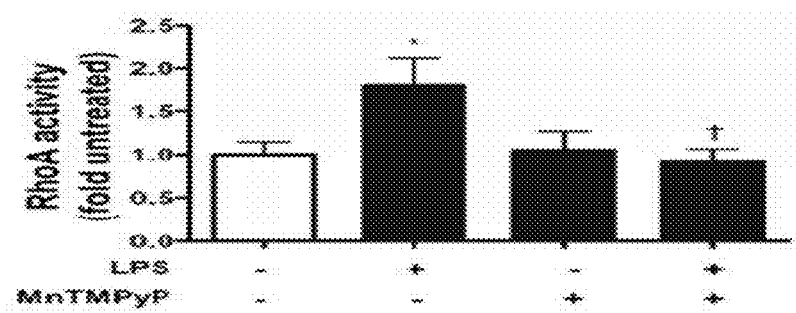

MS/MS of the 1700.5 m/z peak was also performed in positive reflector mode without collision-induced dissociation. MS and MS/MS spectra were analyzed using Protein Pilot 3.0, Mascot Distiller, and PEAKS software packages.
Results Peroxynitrite produced during LPS exposure can affect different proteins via the nitration of tyrosine residues. Nitration of tyrosines can affect protein structure and function. One of the key regulators of endothelial barrier disruption in response to LPS is the small GTPAse RhoA. Thus, whether RhoA activity is modulated by nitration was examined. The data indicated that LPS significantly increased RhoA activity in HLMVEC and this was attenuated by the peroxynitrite scavenger, MnTMPyp (FIG. 2A). Further, it was determined that LPS induces RhoA nitration (FIG. 2B) and this was attenuated by MnTMP. Thus, RhoA is activated and nitrated in HLMVEC after LPS treatment (1 EU/ml, 4 h) and these events are prevented in the presence of MnT-MPyP.

Mass spectrometry (MS) was used to identify peaks that differed from the predicted masses by +45 Da (equal to nitro group addition) in RhoA peptide fragments obtained from LPS challenged HLMVEC. HLMVEC were exposed or not to LPS (1 EU/ml, 4 h). RhoA protein was then immunoprecipated, run on a 4-20% gradient gel and stained with Coomassie blue. The RhoA band was then subjected to in-gel chymotrypsin/trypsin digestion and the resulting peptide fragments subjected to MALDI-TOF MS analysis (4 runs). Peptides coverage was 93%. A single nitrated peptide with amino acid sequence SKDQFPEVY*VPTVF was identified in LPS treated cells corresponding to a peptide of 1700.5 m/z (FIG. 3A).

MS/MS was also carried out to confirm the peptide sequence and the position of the nitro-group as Y34. The further MS/MS analysis of the 1700.5 m/z peptide was obtained in positive reflector mode (3 runs). The resulting spectrum was fitted to the peptide sequence (SKDQFPEVY (NO2)VPTVF) from a human RhoA modified at Y34 by nitro-group.

In conclusion, LPS significantly increased RhoA activity in HLMVEC and this was attenuated by the peroxynitrite scavenger, MnTMPyp. Further, it was determined that LPS induced RhoA nitration. RhoA nitration was attenuated by MnTMPyp. Thus, RhoA is activated and nitrated in HLMVEC after LPS treatment and these events are prevented in the presence of MnTMPyP. The nitrated peptide SKDQF-PEV(X)VPTVF (SEQ ID NO:31) where "X" is 3-nitrotyrosine was located within the region of amino acids 26-39 and was not found in untreated cells.

Example 3

NipR1 Peptide Prevents RhoA Nitration and RhoA Activity, and Enhances HLMVEC Barrier Function Materials and Methods
RhoA Protein Purification The B1-21 strain of Escherichia coli was transformed with a polyHis-pET47b plasmid containing human RhoA and RhoA Y34F mutant sequences. Isopropyl-beta-D-thiogalactopyranoside (IPTG, 1 mM) was added and the cells were incubated for 18-20 h at 25° C. Bacteria were then harvested by centrifugation and the pellet was immediately lysed in 40 mM Tris-HCl, 5% glycerol, 1 mg/mL lysozyme, 100 mM NaCl, protease inhibitor cocktail, ribonuclease A (Sigma), and deoxyribonuclease I (Sigma). The pellet was gently rocked for 30 minutes, sonicated and subjected to ultracentrifugation. The supernatant was loaded onto a His-prep FF 16/10 column using binding buffer (40 mM Tris-HCl, 100 mM NaCl, 5% glycerol, 30 mM imidazole) at 0.1 ml/min flow. The column was washed with 40 mM Tris-HCl, 300 mM NaCl, 5% glycerol, 30 mM imidazole using a flow rate of 1.5 ml/min. Elution of the histidine-tagged protein was accomplished using elution buffer (40 mM Tris-HCl, 300 mM NaCl, 5% glycerol, 400 mM imidazole) at 1.0 ml/min flow. Collected fractions were loaded for size-exclusion gel filtration on a HiLoad 26/60 Superdex 75 column using gel filtration buffer (60 mM Tris-HCl, 100 mM NaCl, 5% glycerol) at 0.2 ml/min flow. Fractions were collected and analyzed by Coomassie blue staining and Western blot. All purification steps were performed at 4° C., and purified protein was stored at −80° C.
Results To determine whether it was possible to specifically target RhoA and prevent its nitration at Y34 a shielding peptide strategy was utilized. Docking experiments led to the identification of a peptide designated nitration inhibitory peptide for RhoA 1 (NipR1; FIG. 3B). Docking experiments indicated this peptide would bind to the flap region. A peptide in which Y34 was substituted with a phenylalanine residue (NipR1F; FIG. 3C) was also synthesized as a control. A biotinylated peptide centered on Y34 containing the sequence QFPEVYVPTVF (SEQ ID NO:20) was synthesized conjugated to the HIV TAT sequence and designated as nitration inhibitory peptide 1 (NipR1) was designed to interact with the flap region of the Switch I domain in RhoA (FIG. 3B). The phenylalanine (F) substituted peptide (NipR1F) was also synthesized to serve as a control (FIG. 3C, right panel).

To confirm binding a pull-down assay was carried out using biotinylated NipR1 and NipR1F peptides. To evaluate the ability of each peptide to bind to RhoA each peptide (100 ng/ml) was mixed with recombinant human RhoA (0.1 mg) for the biotin pull down assay. The pull-down assay indicated a strong interaction between RhoA and both peptides, demonstrating that each peptide has a high affinity for RhoA.

To determine if the NipR1 peptide could shield RhoA against nitration in LPS-exposed HLMVEC, NipR1 and NipR1F peptides were fused with the HIV TAT sequence to increase peptide permeability (See FIG. 3).

Figure 4A:
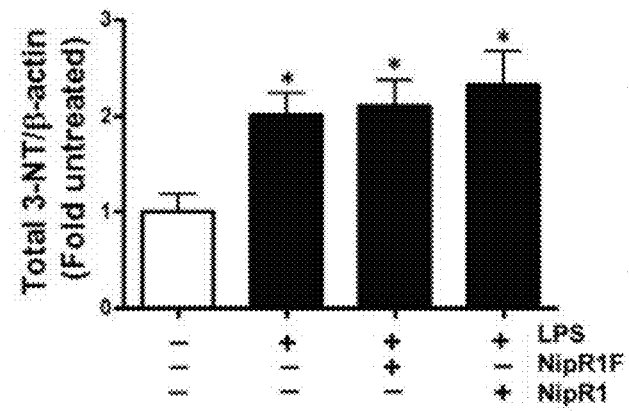
FIG. 4A-C are histograms showing (A) total 3-NT/β-actin (Fold untreated), (B) nitrated RhoA (Fold untreated) and (C) RhoA Activity, respectively, in HLMVEC treated with or without LPS at 1 EU/ml (LPS), then treated with or without 100 ng/ml NipR1F or 100 ng/ml NipR1 peptides. Data are mean±SEM; N=3. *=P<0.05 vs. untreated; †=P<0.05 vs. LPS alone.
Figure 4B:
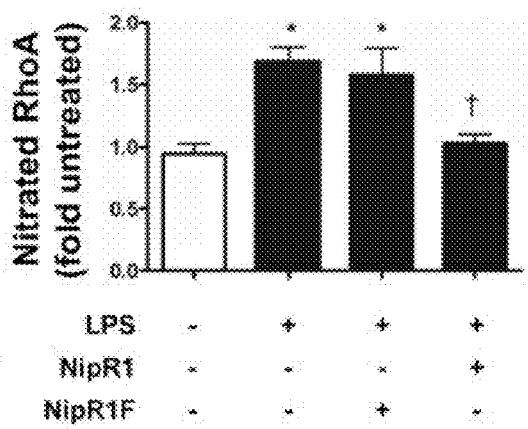
Figure 4C:
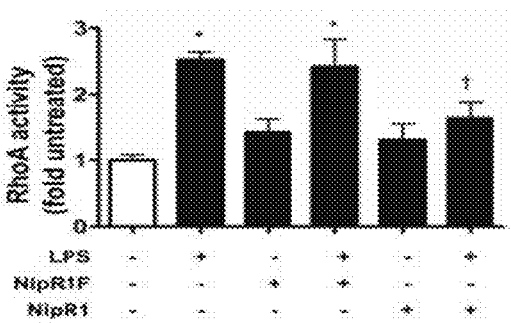
Figure 5:
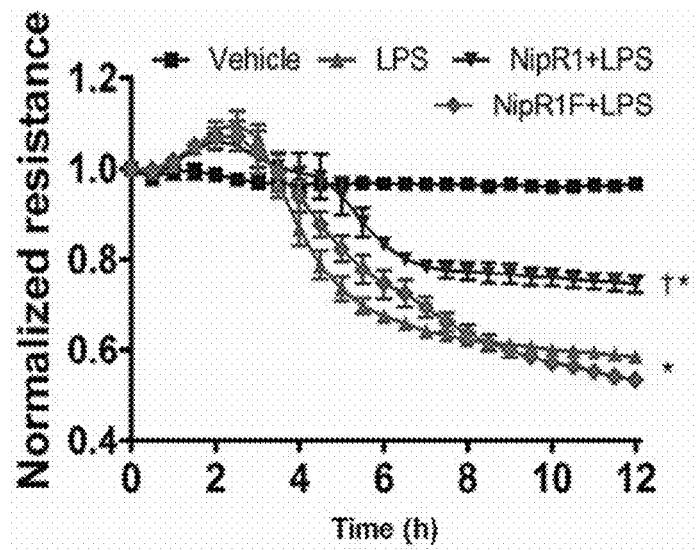
FIG. 5 is a scatter dot plot showing transendothelial resistance (normalized resistance) over time (h) for HLM-VEC in the presence of vehicle alone (■), 1 EU/ml Lipopolysaccharide, (LPS ▲), the NipR1 peptide with LPS, (NipR1+LPS ▼) and the NipR1F peptide with LPS (NipR1F+LPS ♦), respectively. Data are mean±SEM; N=3. *=P<0.05 vs. untreated; †=P<0.05 vs. LPS alone.
Figure 6:
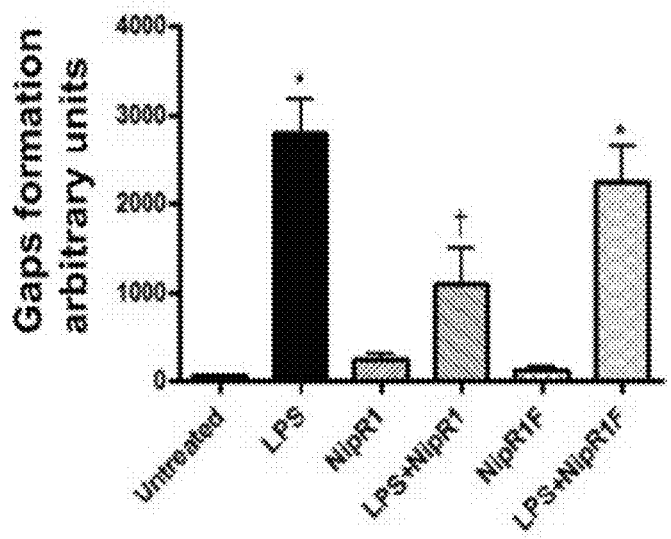
FIG. 6 is a histogram showing gaps formation between cells (arbitrary units) in untreated, LPS, NipR1, LPS+NipR1, NipR1F and LPS+NipR1F. Data are mean±SEM; N=3. *=P<0.05 vs. untreated; †=P<0.05 vs. LPS alone.

To test the activity of the peptides, HLMVEC were exposed to non-biotinylated NipR1 and NipR1F peptides (100 ng/ml, 30 min) then the cells were treated with LPS (1 EU/ml). The nitration and activity assay data indicated that the increase in total protein nitration induced by LPS in HLMVEC was unaffected by either peptide. However, NipR1, but not NipR1F reduced the LPS mediated increase in both RhoA nitration (FIG. 4B) and RhoA activation (FIG. 4C). In addition, NipR1, but not NipRF1, attenuated the LPS-mediated disruption of the HLMVEC barrier as determined both by preservation of TER (FIG. 5) and a reduction in cell-cell gaps (FIG. 6).

In conclusion, the LPS-mediated increases in RhoA nitration and activation were attenuated by NipR1, but not NipRF1. Decreased RhoA activity in NipR1-exposed cells also attenuated the LPS mediated decrease in TER and reduced the gap formation between cells.

Example 4

NipR1 Peptide Attenuates RhoA Nitration and Activation in the Lungs of LPS Treated Mice Materials and Methods
Experimental Mouse Protocol
The Committee on Animal Research at Georgia Regents University approved all animal protocols and procedures.

Stock solutions of *Escherichia coli* LPS (0111:B4) were prepared in saline. Male C57B1/6 mice (10 weeks of age, Harlan Laboratories) received vehicle (saline) or 1 mg/kg peptide via an intraperitoneal injection 6 h before intratracheal installation of LPS ($6.75 \times 10^4$ Endotoxin Units/g body weight). Mice were examined 24 h after LPS treatment. At the end of the treatment lungs were flushed with 3 ml of ice-cold PBS (5 mM EDTA), excised, dipped in saline and blotted dry. A portion of the lung was quickly snap-frozen in liquid nitrogen, crushed to powder in a pre-chilled mortar and stored at −80° C. The remaining lung tissue was stored at −80° C.

Results

Figure 7A:
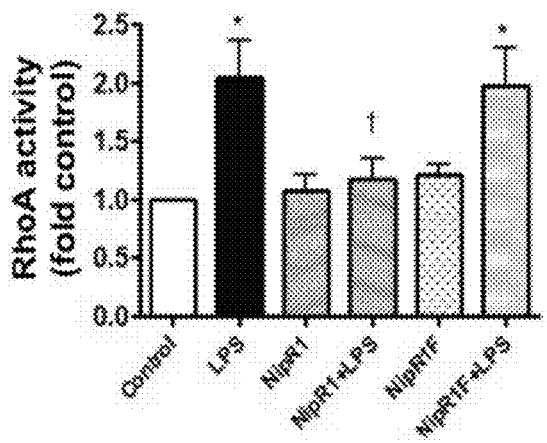
FIGS. 7A-D are histograms showing (A) RhoA Activity (fold control); (B) RhoA protein levels (fold vehicle); and (C) nitrated RhoA (fold control) respectively, in the lung tissue of mice in untreated (control) and following treatment with LPS, NipR1, LPS+NipR1, NipR1F and LPS+NipR1F.
Figure 7B:
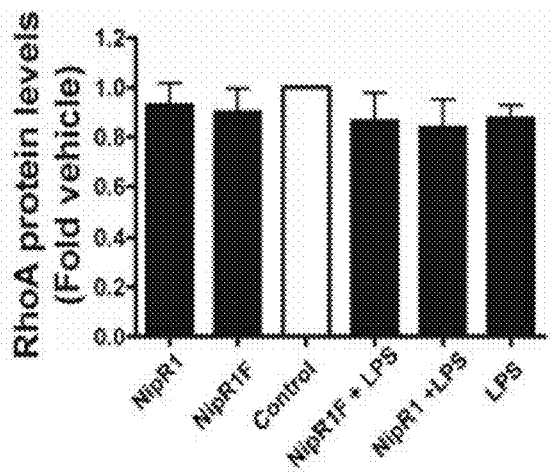
Figure 7C:
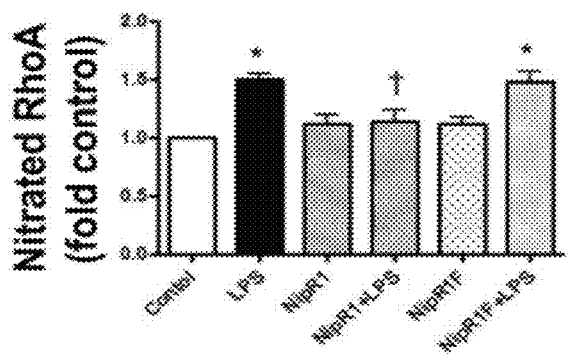
Figure 7D:
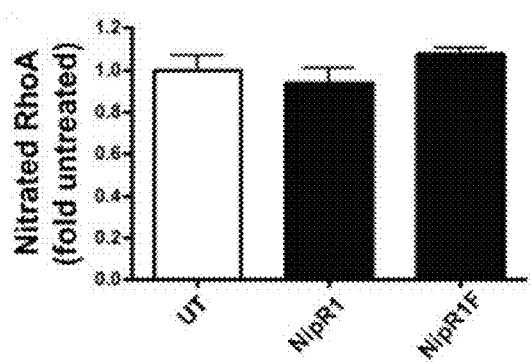

To explore the therapeutic potential of NipR1 a mouse model of ALI induced by the intra-tracheal (i.t.) distillation of LPS was utilized. Mice were administrated with NipR1 or NipR1F peptides, prior to LPS exposure. Mice received vehicle, NipR1 or NipR1F (i.p., 0.1 mg/kg) 6 h prior to i.t. instillation of vehicle or LPS (2 mg/kg). After 24 h, mice were sacrificed and lung tissue was obtained to determine RhoA activity and RhoA nitration, LPS induced RhoA activation in the mouse lung as in HLMVEC (FIG. 7A). However, LPS-mediated increase in RhoA activity in the mouse lung was attenuated by NipR1, but not by NipR1F (FIG. 7A). Likewise, immunoprecipitation of RhoA showed that NipR1, but not NipR1F attenuated the LPS-mediated increase in RhoA nitration (FIG. 7C). Total RhoA protein levels and basal RhoA nitration were measured. Neither peptide nor LPS treatment altered total RhoA protein levels (FIG. 7B). Likewise, basal RhoA nitration levels (FIG. 7D) were unchanged.

In conclusion, NipR1, but not NipR1F attenuated the LPS-mediated increase in RhoA nitration. The peptides alone do not alter the basal levels of nitrated RhoA.

Example 5

NipR1 Peptide Preserves Lung Function in LPS Treated Mice

Materials and Methods

Isolation of Bronchoalveolar Lavage Fluid (BALF)

BALF was obtained by instilling and withdrawing 1 mL of PBS via a tracheal cannula. Part of the solution was used to determine protein levels in the BALF. In addition, cells were pelleted at 2,500 g for 10 min and resuspended in water for 15 sec to lyse red blood cells. Leukocytes were resuspended in 1 ml PBS, and total cell count determined using a haemocytometer.

Analysis of Lung Function

Mice were anesthetized with pentobarbital (90 mg/kg, i.p.), tracheostomized with a metal 1.2 mm (internal diameter) cannula and connected to a Flexi Vent (Scireq Inc) ventilator. Ventilation was initiated at a tidal volume of 10 ml/kg and a rate of 150/min. A TLC maneuver was performed, followed by 15 sec later, by a sinusoidal 1 Hz oscillation. Subsequently, an 8 sec forced oscillatory signal (0.5-19.6 Hz) was applied, the mechanical input impedance of the respiratory system was calculated, and a model containing a constant phase tissue compartment was fit to input impedance in order to evaluate tissue elastance. Dynamic pressure-volume maneuvers were performed by step-wise increasing the airway pressure to 30 cm $H_2O$ and then reversing the process.

Immunohistochemical Analysis of the Mouse Lung

Lungs were inflated with 10% formalin under 15 cm $H_2O$ pressure and immersed in the same solution before tissue processing into paraffin embedded blocks and 4 µm sections were then cut stained with H&E. Histopathological assessment was conducted by two researchers who were masked to treatment group. H&E stained sections were scored for the presence of neutrophil in the alveolar space, neutrophils in the interstitial space, the existence of hyaline membranes, proteinaceous debris filling the airspaces and alveolar septal thickening as described previously (Matute-Bello, et al., *Am. J. Respir. Cell Mol. Biol.* 44, 725-738 (2011)).

MPO Staining

Sections (5 µm) were cut from paraffin blocks and mounted on treated slides (Superfrost+). Slides were air dried overnight, placed in a 60° C. oven for 30 min, deparaffinized in xylene and run through graded alcohol to distilled water. Endogenous peroxidase was quenched with 0.3% $H_2O_2$ for 5 min, followed by two rinses with distilled water. Slides were pretreated with Target pH 6, (Dako), rinsed in distilled water, incubated in Power Block (Biogenex), rinsed in distilled water, placed in PBS for 5 min, incubated with primary antimyeloperoxidase (Cappel, 1:2000 dilution) for 30 min at 25° C. After two rinses in PBS, slides were incubated with a peroxidase-labeled polymer conjugated to goat anti-rabbit secondary IgG (Envision+, Dako) for 30 min and rinsed in PBS. Bound antibody was detected with the DAB+ substrate kit, (Dako). Hematoxylin was used as a counter-stain. MPO-stained slides were then evaluated by scoring (0-4) for the presence of neutrophils within the alveolar walls.

Cytokine and Chemokine Detection in the Bronchoalveolar Lavage Fluid

Analytes (pg/mL) were assessed with the MCYTOMAG70K assay (EMD Millipore) as previously described (Lucas, R., et al., *Proc. Natl. Acad. Sci. USA* 109, 2084-2089 (2012)).

Immunofluorescence

HLMVEC were grown on gelatin-coated coverslips and exposed to LPS in the presence or absence of the NipR1 peptides. The cells were permeabilized and blocked for 1 h at 25° C. in 5% BSA blocking buffer. A primary antibody against ZO-1 (Invitrogen, 1:100 dilution) was added. Plates were incubated overnight at 4° C. then a secondary antibody (AlexaFluor) was added for 2 h. Slides were examined with Zeiss immunofluorescence microscope Axio Observer D1. The gaps between the cells were calculated using Zeiss Axio Observer software.

Results

Figure 8A:
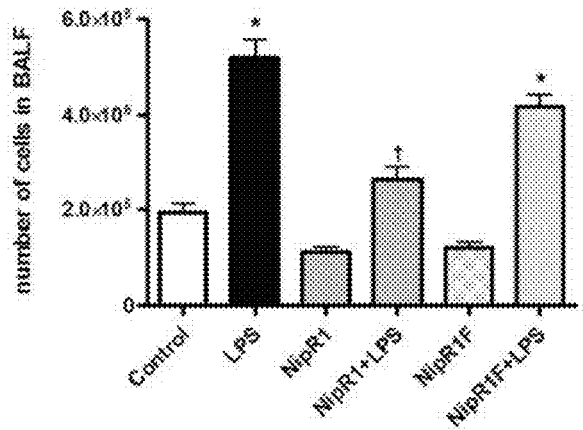
FIGS. 8A-B are histograms showing (A) number of cells in BALF; and (B) protein concentration in BALF (mg/ml), respectively, in the lungs of mice following exposure to control, LPS, NipR1, LPS+NipR1, NipR1F or LPS+NipR1F, respectively.
Figure 8B:
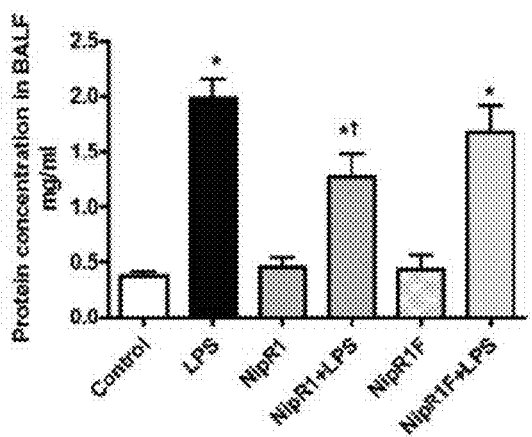
Figure 8C:
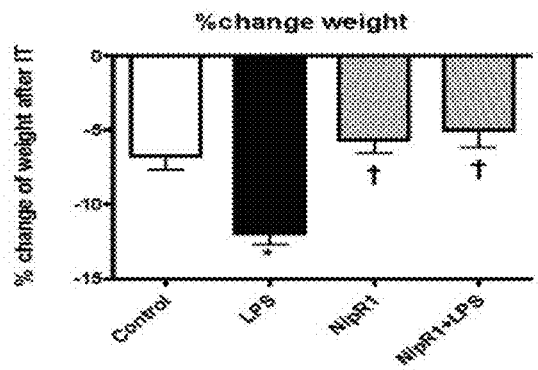
FIG. 8C is a histogram showing % change in body weight after IT following exposure to control, LPS, NipR1 or LPS+NipR1, respectively. Data are mean±SEM; N=4-48, *: P<0.05 from Control; †: P<0.05 from LPS alone.

Mice were used to perform additional physiological, biochemical and morphological studies to evaluate the efficacy of the NipR1 peptide in attenuating symptoms of ALI. Mice received vehicle, NipR1 or NipR1F (i.p., 0.1 mg/kg) 6 h prior to i.t. instillation of vehicle or LPS (2 mg/kg). After 24 h, mice were anesthetized and BALF was collected. Measurements of lung mechanics were also carried out. Total white blood cell counts were significantly increased in the BALF after LPS exposure and these increases were attenuated by NipR1, but not by NipR1F (FIG. 8A). A similar protective effect was observed when protein concentration in the BALF was measured (FIG. 8B). Further, NipR1, but not NipR1F was able to prevent the weight loss (presumably dehydration) associated with LPS exposure (FIG. 8C).

Figure 9A:
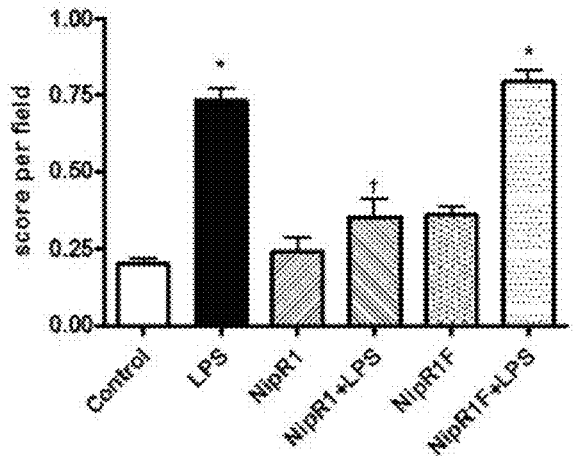
FIGS. 9A-B are histograms showing (A) score per field; and (B) MPO score per field in untreated (control) and following treatment with LPS, NipR1, NipR1+LPS, NipR1F and NipR1F+LPS.
Figure 9B:
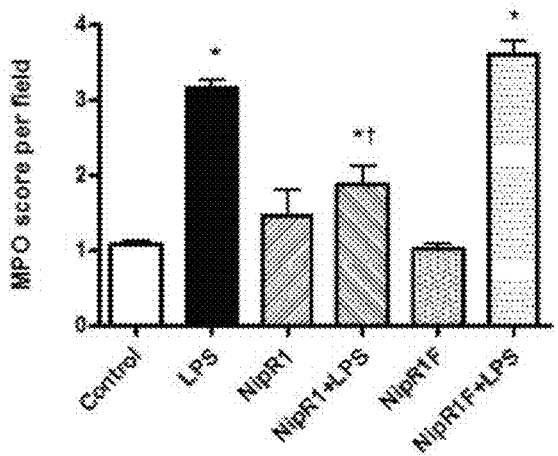
Figure 9C:
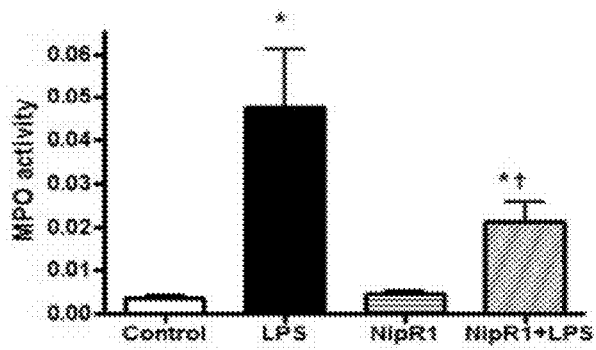
FIG. 9C is a histogram showing MPO activity induced by control, LPS, NipR1 and NipR1+LPS, respectively. Data are mean±SEM; N=4-48, *: P<0.05 from Control; †: P<0.05 from LPS alone.
Figure 10:
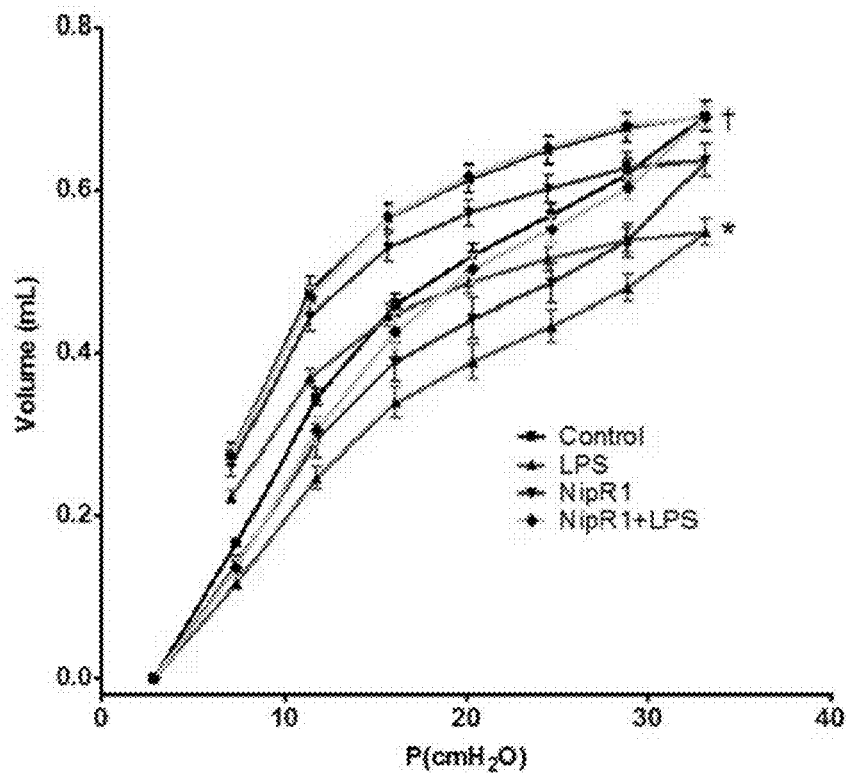
FIG. 10 is a line graph showing Volume (mL) over P (cmH$_2$O) for Control (■), LPS (▲), NipR1 peptide (▼) or NipR1+LPS (♦). Data are mean±SEM; N=4-48, *: P<0.05 from Control; †: P<0.05 from LPS alone.

Histopathological changes in the lungs were also assessed. Lung sections were examined for signs of inflammation after hematoxylin and eosin staining. LPS induced severe alveolar damage that included the presence of a large amount of neutrophils and red blood cells in the alveolar and interstitial space, formation of hyaline membranes, septal thickening and debris accumulation in the alveoli. Again, NipR1, but not NipRF1, reduced these pathological changes (FIG. 9A). NipR1, but not NipRF1, also attenuated the LPS induced increase in MPO staining in the alveolar space (FIG. 9B) and attenuated MPO activity in lung homogenates (FIG. 9C). The analysis of dynamic pressure-volume relationships in the mouse lung also shows that a reduction in lung elastance induced by LPS was also prevented by NipR1 but not NipRF1 (FIG. 10), indicative of a preservation of lung mechanics. Finally, the data indicate that NipR1 attenuated the LPS-mediated induction of multiple pro-inflammatory cytokines and chemokines (Table 3).

In conclusion, cell infiltration into the BALF was significantly increased in LPS treated animals. The LPS-mediated decrease in body weight is attenuated by NipR1, but not by NipR1F. Likewise, the inflammatory response induced by LPS is reduced by NipR1, but not by NipR1F. Thus, NipR1, but not by NipR1F prevents the LPS-mediated disruption of lung airway mechanics.

Example 6

Elucidation of the Mechanism of Nitration Mediated RhoA Activation

Materials and Methods

Rapid Kinetic Analysis of Nucleotide Binding to RhoA

RhoA was treated with authentic peroxynitrite (500 µM, 30 min) to induce tyrosine nitration in buffered solution. For kinetic analyses, 2 µM of either mart-GTP or -GDP was mixed with RhoA (0.1 µM) in a stopped-flow instrument (SX-20, Applied Biophysics). Increases in fluorescent intensity mant-nucleotide binding to RhoA were then measured using excitation 350 nm and cutoff filter 395 nm for 0.2-1 second. Acquired kinetic curves for 3-5 experiments were averaged and fitted using the Pro-kineticist software to determine observed binding constants.

Statistical Analysis

Statistical analysis was performed using GraphPad Prism version 4.01 (GraphPad). The mean±SD or LPS increased RhoA nitration and activity SEM was calculated for all samples, and the significance was determined either by the

TABLE 1

| | family | | Control (n = 13) | LPS (n = 13) | NipR1 (n = 5) | NipR1 + LPS (n = 7) |
|---|---|---|---|---|---|---|
| Cytokines | Type I receptor | IL-3 | 0.33 ± 0.12 | 2.65 ± 0.23 a*** | 0.11 ± 0.07 | 1.89 ± 0.17 a***, b** |
| | | IL-4 | 0.033 ± 0.033 | 3.98 ± 0.33 a*** | 0.054 ± 0.054 | 3.19 ± 0.29 a***, b* |
| | | IL-6 | 55.5 ± 19.0 | 7510 ± 1289 a*** | 26.8 ± 21.4 | 3714 ± 911 b** |
| | | IL-7 | 0.77 ± 0.05 | 3.8 ± 0.3 a*** | 1.03 ± 0.14 | 3.03 ± 0.24 a***, b* |
| | | IL-9 | 46.4 ± 8.8 | 287.2 ± 29.9 a*** | 69.1 ± 21.2 | 208.4 ± 19.1 a***, b* |
| | | IL-12 | 2.21 ± 0.47 | 22.9 ± 4.0 a*** | 1.31 ± 0.53 | 13.7 ± 0.8 b* |
| | | IL-13 | 2.20 ± 0.68 | 78.0 ± 10.3 a*** | 3.33 ± 2.58 | 51.7 ± 6.5 a***, b* |
| | | IL-15 | 1.85 ± 0.40 | 54.5 ± 5.4 a*** | 2.60 ± 1.29 | 40.0 ± 4.1 a***, b* |
| | | GM-CSF | 13.00 ± 2.46 | 89.53 ± 5.59 a*** | 14.29 ± 4.72 | 75.06 ± 5.53 a***, b* |
| | | G-CSF | 432.1 ± 86.7 | 22874 ± 816 a*** | 232.0 ± 118.2 | 19131 ± 1655 a***, b** |
| | | LIF | 3.20 ± 0.91 | 234 ± 38 a*** | 3.49 ± 2.14 | 117 ± 25 a*, b** |
| | | IL-2 | 1.80 ± 0.35 | 7.00 ± 0.52 a*** | 1.43 ± 0.39 | 6.52 ± 0.25 a*** |
| | | M-CSF | 11.6 ± 4.6 | 33.7 ± 2.6 a*** | 9.9 ± 5.9 | 28.5 ± 2.7 a** |
| | | IFNγ | 3.21 ± 1.17 | 2232 ± 667 a*** | 4.46 ± 2.42 | 972 ± 238 b* |
| | | TNF-α | 9.95 ± 1.23 | 621 ± 108 a*** | 8.51 ± 4.90 | 311 ± 30 b** |
| | | IL-10 | 4.27 ± 1.22 | 46.3 ± 3.7 a*** | 3.21 ± 1.15 | 39.8 ± 3.2 a*** |
| | IL-1 | IL-17 | 0.029 ± 0.025 | 36.3 ± 10.5 a** | 0.522 ± 0.522 | 50.1 ± 14.1 a** |
| | | IL-1α | 18.70 ± 1.42 | 187.6 ± 18.4 a*** | 13.66 ± 3.16 | 201.2 ± 29.7 a*** |
| | | IL-1β | 2.86 ± 0.71 | 198 ± 42 a*** | 2.28 ± 1.50 | 168.9 ± 32.2 a* |
| Chemokines | CCL | MIP-1α | 15.2 ± 2.7 | 590 ± 100 a*** | 20.5 ± 13.7 | 350 ± 48 a**, b* |
| | | MIP-1β | 16.8 ± 3.2 | 3270 ± 955 a*** | 14.7 ± 12.3 | 1121 ± 245 b* |
| | | MPC-1 | 11.3 ± 1.6 | 952 ± 197 a*** | 10.1 ± 5.0 | 476 ± 92 b* |
| | | RANTES | 13.5 ± 2.0 | 330 ± 41 a*** | 7.9 ± 3.4 | 277 ± 34 a*** |
| | CXCL | MIP-2 | 96 ± 25 | 845 ± 121 a*** | 21.0 ± 6.1 | 531 ± 44 a**, b* |
| | | KC | 11.51 ± 1.79 | 186 ± 24 a*** | 6.83 ± 2.31 | 169 ± 29 a*** |
| | | LIX | 26.0 ± 7.7 | 411 ± 46 a*** | 19.9 ± 14.5 | 479 ± 50 a*** |

BALF cytokines concentrations (pg/ml) are presented as Mean ± SEM for groups (Control N = 13, LPS N = 13, NipR1 N = 5, LPS + NipR1 N = 7).
a Significantly different from the control group,
b Significantly different from the LPS group (*p < 0.05, p < 0.01, *p < 0.001).
Greyed rows indicate no significant changes between LPS untreated and LPS plus NipR1 treatment group.
Analytes were assessed with the MCYTOMAG-70K assay (IP-10, IFN-γ-induced protein 10; KC, keratinocyte-derived chemokine; LIF, leukemia inhibitory factor; LIX, LPS-induced CXC chemokine; MCP-1, monocyte chemoattractant protein 1; MIG, monokine induced by IFN-γ; RANTES, regulated upon activation, normal T-cell expressed and secreted).

unpaired t-test (for 2 groups) and ANOVA (for >3 groups). For the ANOVA analyses, Newman-Kuels posthoc testing was employed. A value of P<0.05 was considered significant.

Results

Comparison of RhoA GTPase in different crystal structures associated with different catalytic stages revealed that the Switch I region of RhoA undergoes a major conformational change during the catalytic cycle. This sub-region of Switch I, which changes the conformation change during catalytic cycling, was termed the "flap" (amino acids 28-40). Analysis of the X-ray crystal structure of RhoA shows that Y34 is located in a flexible regions (flap) of the Switch I domain that is responsible for nucleotide binding. The flap has an unstructured, flexible characteristic. A 100 ns molecular dynamic (MD) simulation of the flap region in RhoA and RhoA nitrated at Y34 was carried out and the movement of the flap region was also superimposed onto the x-ray crystal structure RhoA bound to a GEF protein. The molecular dynamic (MD) simulations predicted that nitration of Y34 would lead to the opening of the flap similar to that seen in the RhoA-GEF complex crystal structure. This was predicted to increase nucleotide cycling by decreasing the affinity of RhoA for GDP, leading to faster GDP release, thus, increasing RhoA activity.

Figure 11:
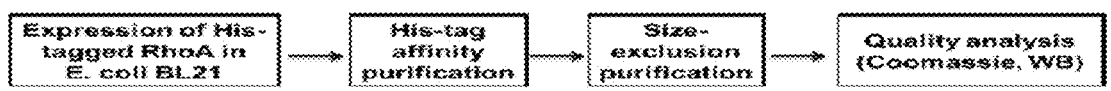
FIG. 11 is a schematic representation of the procedure for production and purification of recombinant RhoA protein.
Figure 12A:
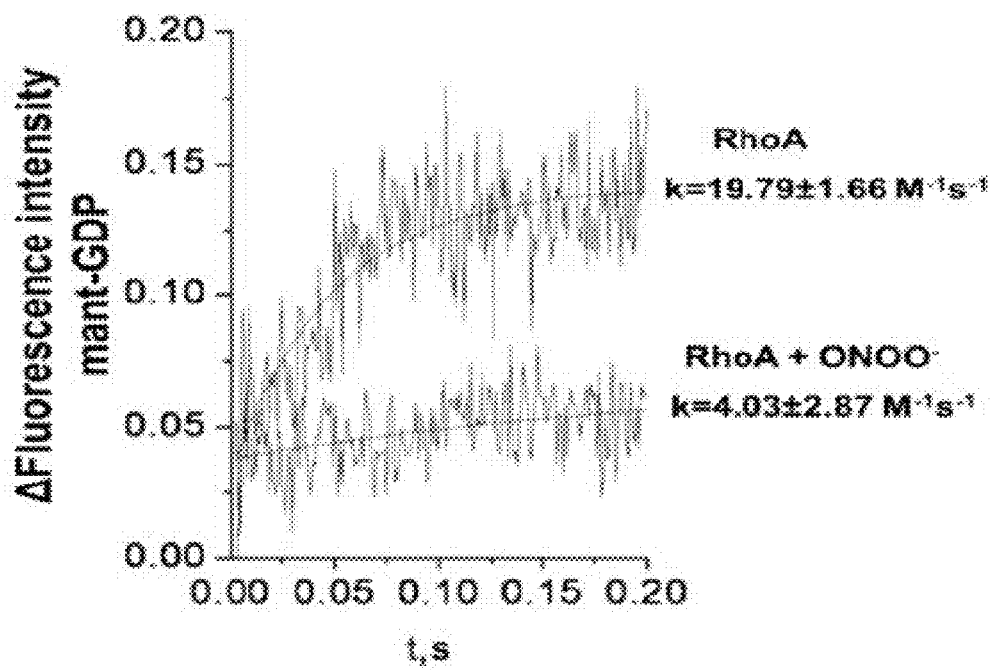
FIGS. 12A-B are line graphs showing change in fluorescence intensity for (A) mant-GDP; and (B) mant-GTP, respectively, over time (s) for RhoA and RhoA+ONO$^-$, respectively.
Figure 12B:
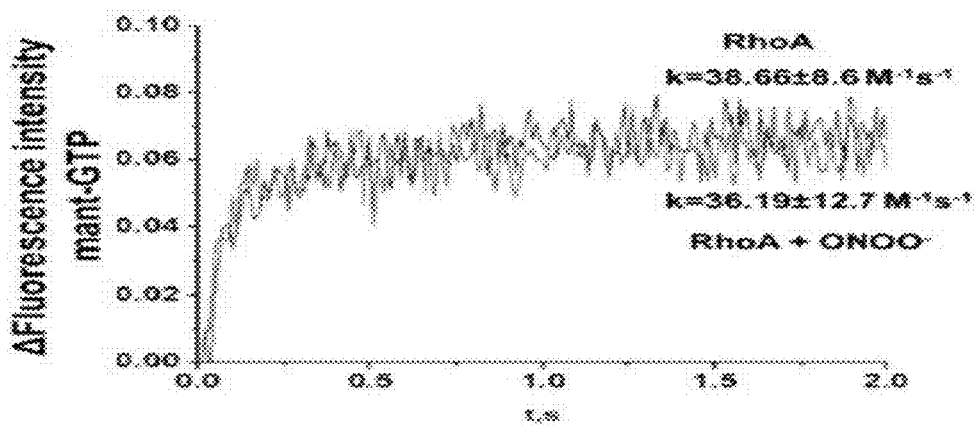

To test the validity of the MD data kinetic studies were performed. His-tagged human RhoA construct was expressed in the *Escherichia con* BL21 strain. First, the bacterial lysate was purified by 6His-tag affinity on a Ni-NTA column. Second, the proteins in the elution fraction from the affinity purification were separated by size-exclusion chromatography (FIG. 11). The fraction containing RhoA was identified both by Coomassie blue staining and Western blot analysis. The recombinant purified RhoA was subjected to rapid flow kinetics to evaluate GDP and GTP binding using fluorescently labeled guanine nucleotides. Peroxynitrite decreases GDP binding to purified RhoA. Human recombinant RhoA was exposed to authentic peroxynitrite (100 μM, 30 min) on ice. The kinetics of binding fluorescently labeled GDP (FIG. 12A) or GTP (FIG. 12B) to RhoA was then performed using stop-flow analysis. Three measurements were averaged and fitted with bimolecular reaction equation. The exposure of RhoA to peroxynitrite markedly reduced the GDP binding constant (FIG. 12A). Nitration decreases the binding constant of GDP to RhoA from 19.79+1.66 M-1S-1 to 4.03+2.87 M-1S-1 but does not affect GTP binding (RhoA alone=38.66+8.6 M-1S-1 vs. RhoA+ONOO=36.19+12.7 M-1S-1). However, nitration of RhoA had no effect on the GTP binding constant (FIG. 1213).

Figure 12C:
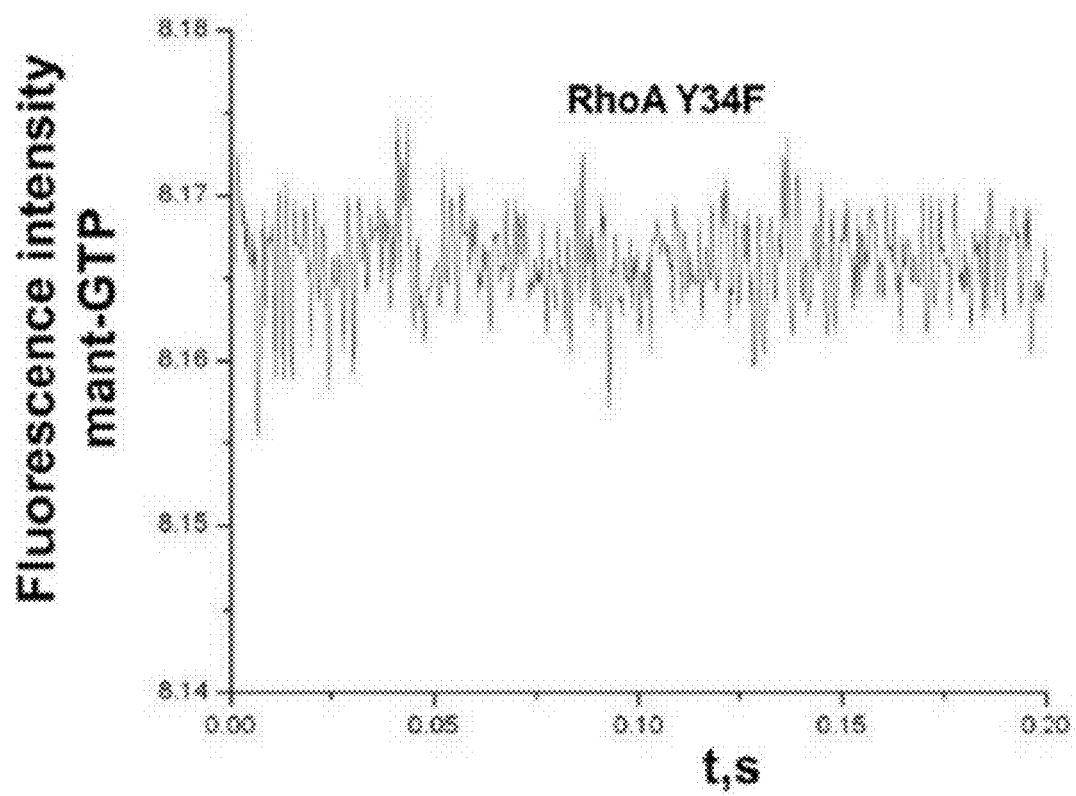
FIG. 12C is a line graph showing the fluorescence intensity of mant-GTP over time (s) for RhoA Y34F.
Figure 13:
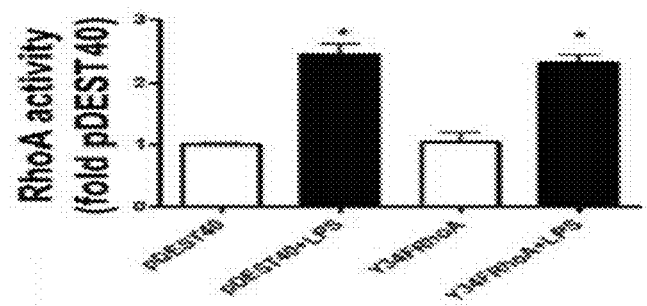
FIG. 13 is a histograms showing RhoA activity (fold pDEST40) for pDEST40, pDEST40+LPS, Y34FRhoA, Y34FRhoA+LPS. Data are mean±SEM; N=3. *: P<0.05 vs. pDEST40 (empty vector) no LPS.
Figure 14:
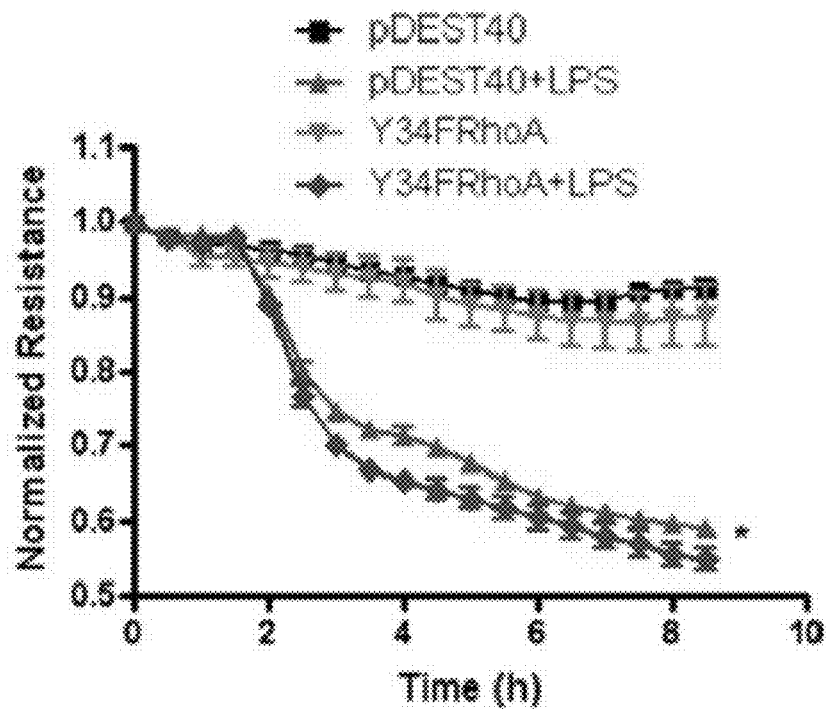
FIG. 14 is a scatter dot plot showing transendothelial resistance (normalized resistance) over time (h) for HLM-VEC expressing pDEST40 (■), pDEST40+LPS (▲), Y34FRhoA (▼) and the Y34FRhoA+LPS (♦), respectively. Data are mean±SEM; N=3. *=P<0.05 vs. untreated; †=P<0.05 vs. LPS alone.
Figure 15:
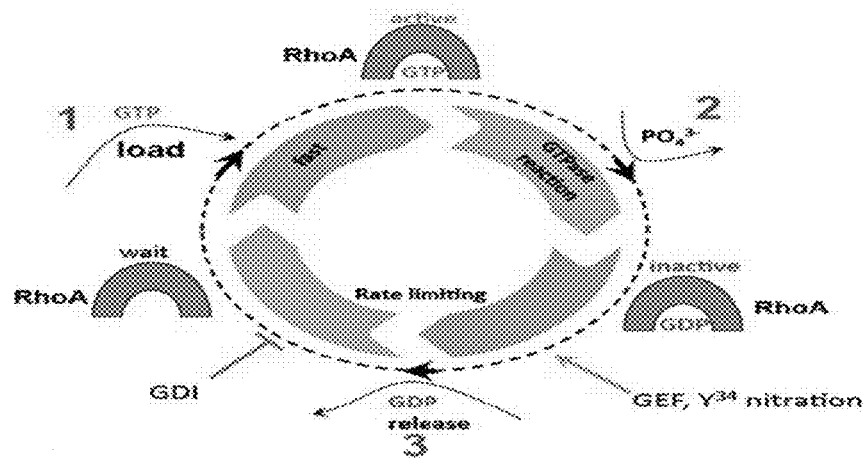
FIG. 15 is a schematic representation of RhoA catalytic cycling. GDP release is a rate limiting step in the RhoA activation. Increased GDP release is assisted by Y34 nitration, leading to faster GTP reload and increased RhoA activity.

A purified RhoA mutant protein in which the tyrosine residue (Y) was replaced by phenylalanine (Y34F RhoA) was also expressed. The kinetics of GTP binding to the Y34FRhoA mutant was also measured by stop-flow analysis using mant-GTP. No binding of GTP was observed indicating that this mutant cannot bind GTP and is therefore catalytically inactive (FIG. 12C). The Y34FRhoA mutant protein was over-expressed in HLMVEC. After 48 h there was a significant increase in RhoA protein. Y34FRhoA mutant protein over-expression did not alter basal RhoA activity or modulate the increase in RhoA activity in LPS treated cells (FIG. 13). The decrease in normalized transendothelial resistance (TER) in response to LPS was also not modulated by Y34FRhoA mutant protein over-expression (FIG. 14). GDP release is a rate limiting step in the RhoA activation. Increased GDP release is assisted by Y34 nitration leading to faster GTP reload and increased RhoA activity (see FIG. 15).

In conclusion, nitration decreases the binding constant of GDP to RhoA, but nitration of RhoA had no effect on the GTP binding constant. The Y34F RhoA mutant protein was unable to bind GTP and was catalytically inactive. When expressed in HLMVEC the Y34F RhoA mutant did not modulate either the increase in RhoA activity or the barrier disruption associated with LPS exposure.

Example 7

Y247 and Y425 are Nitration Sites on Human PKG-1α

Materials and Methods

Sources of Materials

Polyclonal anti-PKG-1α (goat), anti-Calponin-1 (rabbit), and monoclonal anti-Vimentin (Clone: 2Q1035) antibodies were from Santa Cruz Biotechnology (Santa Cruz, Calif.); Monoclonal anti-nitrotyrosine antibody (Clone: CC22.8C7.3) was from EMD Biosciences, Inc. (San Diego, Calif.); monoclonal anti-PCNA (Clone: PC10) and polyclonal anti-SM22-α (goat) antibodies were from Abeam (Cambridge, Mass.); Monoclonal anti-β-actin (Clone: AC-15); and monoclonal anti-myosin heavy chain (MYH) (Clone: hSM-V) antibodies were from Sigma Life Sciences (St. Louis, Mo.); 3-morpholinosydnonimine Nethylcarbamide (SIN-1) was from Cayman Chemicals (Ann Arbor, Mich.); Bovine PKG full length recombinant protein (alpha1 isozyme) and a non-radioisotopic kit for measuring PKG activity were from Cyclex Co., Ltd. (Nagano, Japan); AlamarBlue was from AbD serotec (Raleigh, N.C.); [$^3$HcGMP] was from PerkinElmer (Waltham, Mass.); YASARA software was from YASARA Biosciences GmbH (Vienna, Austria); HEK-293T cells were a kind gift from Dr. John. D. Catravas.

Statistical Analysis

Statistical analysis was performed using GraphPad Prism version 4.01 (GraphPad Software, San Diego, Calif.). The mean±SEM was calculated in all experiments, and statistical significance determined either by the unpaired t-test (for 2 groups) or ANOVA (for >3 groups). For the ANOVA analyses, Newman-Kuels post-hoc testing was employed. A value of p<0.05 was considered significant.

Immunoprecipitation (IP) Analyses

Cells were homogenized in 3× weight/volume of IP buffer (25 mM Hepes, pH 7.5, 150 mM NaCl, 1% NP-40, 10 mM $MgCl_2$, 1 mM EDTA, 2% glycerol, supplemented with protease inhibitor). The homogenates were then centrifuged at 20,000 g at 4° C. for 20 min, the supernatant was collected, and the protein concentration was quantified by the Bio-Rad DC Protein Assay. To 1000 μg of total protein, 4 μg of antibody against PKG-1α was added; the volume was brought to 1 ml with IP buffer, and the mixture was nutated at 4° C. overnight. To precipitate the bound protein, 30 μl of protein G plus agarose suspension (EMD biosciences, Inc., San Diego, Calif.) was added, and the samples were nutated for 2 h at 4° C. To collect the bead-bound antibody, the samples were then centrifuged at 2000 g for 5 min at 4° C., the supernatant was removed, and the beads were washed 3× with 500 μl of IP buffer. To the samples, 30 μl of 2× Laemmli buffer was added, and the samples were boiled for 5 min and then resolved using 4-20% Tris-SDS-Hepes PAGE. The membrane was then probed for 3-nitrotyrosine (1:100 dilution), as described above. The IP efficiency was normalized by re-probing for PKG-1α (1:500).

In-Gel Digestion for Mass Spectrometry

HEK-293T cells were transfected with WT-PKG-1α cDNA for 48 h in high glucose DMEM media containing 10% FBS and 1% antibiotics and then serum starved (1% FBS) for 4 h. The cells were challenged with SIN-1 (500 µM) for 30 min, lysed, and then PKG-1α was purified using the immunoprecipitation technique, as mentioned above. The protein was resolved using 4-20% Tris-SDS-Hepes PAGE and visualized by Imperial Protein Stain (Thermo-Fisher). The band corresponding to PKG-1α (75 kD) was excised, destained, and subjected to overnight in-gel digestion with trypsin (25 ng/µl in 25 mM ammonium bicarbonate buffer, pH 7.8). The peptides were extracted with 0.1% TFA/75% acetonitrile and evaporated to near dryness.

MALDI-TOF Mass Spectrometry

Peptide calibration standards and matrix CHCA were purchased from Applied Biosystems. All spectra were taken on an ABSciex 5800 MALDI-TOF Mass Spectrometer in positive reflector mode (10 kV) with a matrix of CHCA. At least 1000 laser shots were averaged to get each spectrum. The masses were calibrated to known peptide standards. Aliquots (5 µl) of the PKG-1α tryptic digest were taken up into a C18 ZipTip (Millipore) that had been prepared, as per manufacturer's instructions. The bound peptides were desalted with two 5 µl washes of 0.1% TFA and then eluted with 2.5 µl of aqueous, acidic acetonitrile (75% CH3CN, 0.1% TFA). The eluate was mixed with 2.5 ul freshly prepared CHCA stock solution (20 mg/ml CHCA in aqueous acetonitrile, as above), and 1.5 µl portions of this mixture were spotted onto a MALDI sample plate for air drying. Crude peptides (1.5 µl) were additionally mixed with CHCA (1.5 µl) and were spotted. The MS/MS of the 2209.04 m/z peak was done in positive reflector mode without CID. The MS and MS/MS spectra were analyzed in the Mascot Distiller software package.

Results

The association between nitration of PKG-1α and attenuation of kinase activity was shown previously (Aggarwal, S., et al., *Journal of Cellular Physiology* (2011)). However, the tyrosine residues susceptible to this posttranslational event are unknown. To identify nitration sites, HEK-293T cells were transfected with an expression plasmid containing a full length WT-PKG-1α cDNA. After 48 h the cells were exposed or not to the peroxynitrite generator, 3-morpholino-sydnonimine N-ethylcarbamide (SIN-1) (500 µM) for 30 min. The cells were lysed; PKG-1α was immunoprecipitated, and the protein was subjected to SDS-PAGE and Coomassie staining. The band corresponding to PKG-1α was excised, trypsinized, and mass spectrometry (MS) was performed on the extracted peptides.

MS analysis of the human 3-NT modified PKG-1α sequence, LADVLEETHYENGEYIIR (SEQ ID NO:32), corresponding to the peptide including the amino acids 233-250, and the sequence, QIMQGAHSDFIVRLYR (SEQ ID NO:33), corresponding to the peptide including the amino acids 411-426, demonstrated the nitration of Y247 and Y425 (Table 4).

TABLE 4

MS results showing Y247 and Y425 of PKG-1α are nitrated.

| Protein | MW | Protein PI | Pep count | Protein score | Total Ion score |
|---|---|---|---|---|---|
| cGMP dependent protein kinase type 1 alpha (*Homo Sapiens*) | 76943.2 | 5.74 | 17 | 266 | 250 |

| Peptide information | Calc. mass | Start Seq. | End Seq. | ±da | ±ppm |
|---|---|---|---|---|---|
| LADVLEETHYENGEYIIR[Nitro(Y)(15)] | 2209.04 | 233 | 250 | −0.964 | −432 |
| QIMQGAHSDFIVRLYR[Nitro(Y)(15), oxidation(M)(3)] | 1994.98 | 411 | 426 | −0.993 | −498 |

MS/MS was performed to verify the tyrosine nitration sites within PKG-1α. The peptide with m/z 2209.04 (parent peptide LAD VLEETHYENGEYIIR (SEQ ID NO:32) with m/z 2164.04+45 Da of nitro group) was further fragmented and MS/MS data analyzed. The MS/MS spectrum of the 2209.04 m/z ion was obtained in positive reflector mode fitted with peptide 233-LADVLEETHYENGEXIIR-250 (SEQ ID NO:34) where "X" is 3-nitrotyrosine from the PKG-1α sequence. However, due to the low intensity of the peak corresponding to Y425, MS/MS could only confirm the nitration of Y247, indicating that Y425 is a poor nitration site.

Example 8

Nitration of Y247 Attenuates PKG-1α Activity

Materials and Methods

Generation of a Nitration Specific PKG-1α Polyclonal Antibody

The 3-NT Y247 PKG-1α specific antibody was raised against a synthetic peptide antigen ENGE(Y-NO2)IIRQ-GARGDC, where Y-NO2 represent 3-nitrotyrosine. The peptide was used to immunize rabbits. Tyrosine nitration-reactive rabbit antiserum was first purified by affinity chromatography. Further purification was carried out using immunodepletion by non-nitrated peptide ENGEYIIRQ-GARGDC resin chromatography, after which the resulting eluate was tested for antibody specificity by immunoblotting and immune-histochemistry with fluorescent staining.

Results

To determine the role of tyrosine 247 and tyrosine 425 in mediating the nitration dependent inhibition of PKG-1α kinase activity, Y247F- and Y425F-PKG-1α mutants were generated and expressed in HEK-293T cells. HEK-293T cells were transiently transfected with expression plasmids containing WT-, Y247F-, or Y425F-PKG-1α for 48 h. Cells were also treated or not with SIN-1 (500 µM, 30 min). Protein extracts were immunoprecipitated using an antibody raised against PKG-1α and the level of nitrated PKG-1α determined by probing the membranes with an antiserum raised against 3-NT. The blots were then stripped and re-probed for PKG-1α to normalize for the efficiency of the immunoprecipitation.

Figure 16A:
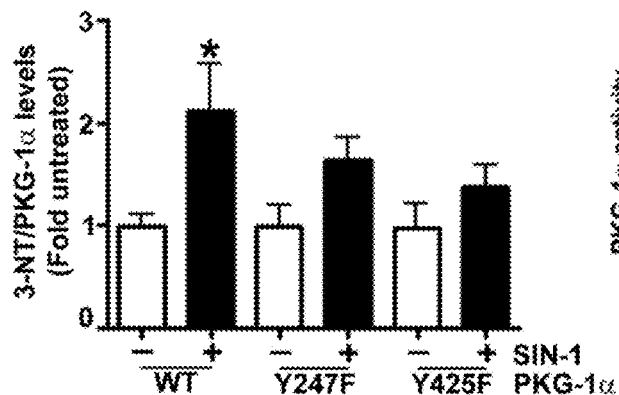
FIGS. 16A-B are histograms showing (A) 3-NT/PKG-1α levels (Fold untreated) of wild type PKG-1α (WT), Y247F PKG-1α (Y247F) and Y425F PKG-1α (Y425F), with or without SIN-1, respectively; and (B) PKG-1α activity (pmol/min/μg) of WT, Y247F and Y425F, with or without SIN-1, respectively. cGMP-independent PKG activity is indicated by white bars, cGMP dependent PKG activity is indicted by black bars. Data are mean±SEM, n=3, *p<0.05 vs. untreated WT-PKG-1α and Y425F-PKG-1α.
Figure 16B:
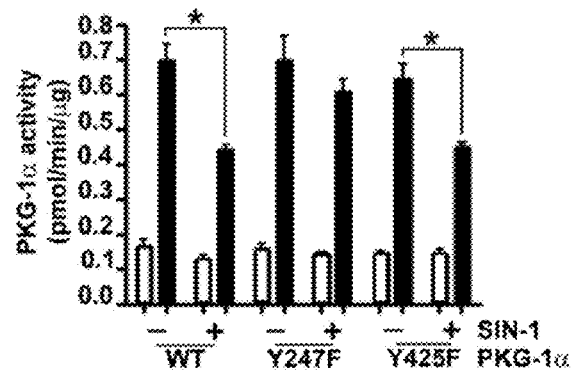

Immunoblot analysis verified increased expression of PKG-1α. The nitration of WT-PKG-1α was significantly increased in the presence of SIN-1 (FIG. 16A). However, there were no significant increases in the nitration levels of Y247F- or Y425F-PKG-1α in the presence of SIN-1 (FIG. 16A). Although SIN-1 did not alter cGMP-independent PKG activity (FIG. 16B, white bars), cGMP dependent PKG activity was attenuated in cells expressing WT- and Y425F-PKG-1α, but not in cells expressing Y247F-PKG-1α (FIG. 16B, black bars).

In conclusion, the moderate increase in the nitration levels of PKG-1α in the cells expressing either the Y247F or the Y425F mutant may be due to the nitration of the other tyrosine site. SIN-1 did not affect basal PKG-1α activity (without exogenous cGMP activation) (FIG. 16B). However, the cGMP-dependent increase in PKG-1α activity in the cells transfected with WT-, and Y425F-PKG-1α was attenuated in the presence of SIN-1, and the activity of the Y247F PKG-1α mutant was unaffected (FIG. 16B). Taken together, these results indicate that Y247 is involved in the nitration-mediated decrease in PKG-1α activity.

Example 9

Nitration of Y247 Attenuates PKG-1α Activity

Materials and Methods
Determination of PASMC Cell Growth
Pulmonary artery smooth muscle cells (PASMC) were grown on a 10 cm dish to 75% confluence, transfected with WT-PKG-1α or Y247F-PKG-1α cDNA using a Qiagen transfection kit, according to manufacturer's instructions, and incubated at 37° C. for 20 h. This method resulted in a—20% transfection efficiency (not shown). The cells were then trypsinized, seeded onto a 6-well plate at a density of $2.5 \times 10^4$ cells per well, and grown for an additional 4 h in serum-free DMEM growth medium containing 1% FBS and antibiotics. The cells were then treated with or without SIN-1 (500 μM) and allowed to grow at 37° C. in the incubator for an additional 48 h. The cellular proliferation was evaluated by counting the cells with a hemacytometer (Cascade Biologicals™, Portland, Oreg.) after the trypsinization of the PASMC monolayers.

Analysis of PASMC Cellular Metabolism
This was determined via the alamarBlue assay (AbD Serotec, Oxford, UK). The assay is based on the reducing ability of metabolically active cells to convert the active reagent, resazurin, into a fluorescent and colorimetric indicator, resorufin. When added to cell cultures, the oxidized, resazurin enters the cytosol and is converted to the reduced, resorufin in the mitochondria by accepting electrons from NADH, NADPH, FADH2, FMNH2, as well as from the cytochromes. The non-toxic and cell permeable nature of alamarBlue permits the long-term exposure of cells. PASMC were grown on a 10 cm dish to 75% confluence, transfected with WT-PKG-1α or Y247F-PKG-1α cDNA, and incubated at 37° C. for 20 h. The cells were trypsinized and seeded onto a 24-well plate at a density of 20,000 cells per well and grown for an additional 4 h in serum and phenol free DMEM growth medium containing 1% FBS and antibiotics. The cells were then treated with or without SIN-1 (500 μM, 48 h) in the presence of 10% well volume of alamarBlue dye. The color change of the dye was determined at an excitation wavelength of 560 nm and an emission wavelength of 590 nm in a Fluoroskan Ascent plate reader. Cells exposed to 0.1% Triton X-100 were used as a negative control, while media containing alamarBlue dye autoclaved for 15 min was used to obtain the 100% reduced form of alamarBlue (positive control). Cellular metabolism was expressed as follows:

$$\% \text{ reduction of alamarBlue} = \frac{\text{Sample value} - \text{Negative control}}{\text{Positive control} - \text{Negative control}} \times 100\%$$

Figure 17A:
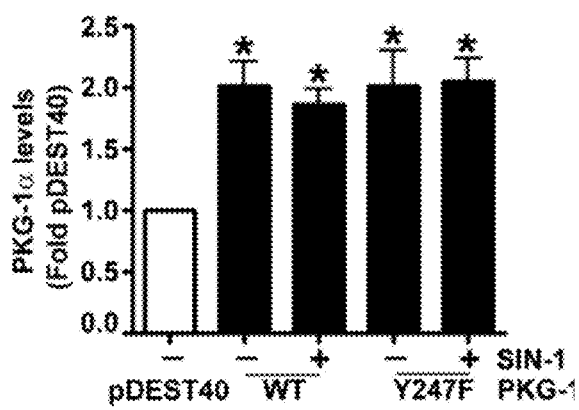
FIGS. 17A-D are histograms showing (A) variations in PKG-1α levels (Fold pDEST40); (B) PKG activity (pmol/min/μg); (C) Cell count (Fold change day 0); and (D) Percentage of reduction of alamarBlue, respectively, for control plasmid (pDEST40, white bar), wild type PKG-1α (WT) and Y247F PKG-1α (Y247F), with or without SIN-1, respectively. Data are mean±SEM, n=4, *p<0.05 vs. pDEST40, † p<0.05 vs. WT-PKG-1α, ‡ p<0.05 vs. WT-PKG-1α+SIN-1.
Figure 17B:
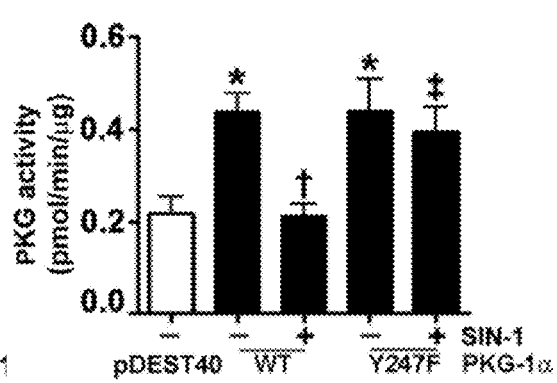

Results
Past studies have demonstrated that the expression of PKG-1 results in decreased proliferation (Kawashima, S., et al., *Arteriosclerosis, Thrombosis, and Vascular Biology* 21, 201-207 (2001); Rudic, R. D., et al., *The Journal of Clinical Investigation* 101, 731-736 (1998)) and acquisition of a contractile phenotype in vascular SMC (VSMC) (Pilz, R. B., et al., *Front Biosci.* 10, 1239-1268 (2005)). Therefore, the effect of these events were investigated in PASMC transiently transfected with expression plasmids containing WT- and Y247F-PKG-1α. The effect of nitration on pulmonary arterial smooth muscle cell (PASMC) growth and metabolism was determined. PASMC were transiently transfected with expression plasmids containing WT-PKG-1α, Y247F-PKG-1α or pDEST40 (as a control) for 20 h. Cells were then exposed or not to SIN-1 (500 μM, 48 h) and the effect on PKG protein levels (FIG. 17A) and activity determined (FIG. 17B).

Whether SIN-1 attenuated PKG kinase activity in cells transfected with WTPKG-1α but not in cells expressing Y247F-PKG-1α was confirmed. The effect on PASMC proliferation and metabolic activity was determined. SIN-1 had no effect on PKG-1α protein levels (FIG. 17A). SIN-1 attenuated the cGMP dependent increase in PKG activity in the cells transfected with WT-PKG-1α, but not those expressing the Y247F PKG-1α mutant (FIG. 17B). The effect of SIN-1 on cellular proliferation (FIG. 17C) and cellular metabolic activity (FIG. 17D) were also determined. PASMC expressing either WT- or Y247F-PKG-1α were less proliferative and metabolically active than the pDEST40 transfected control cells. SIN-1 exposure stimulated proliferation and metabolism in WT-, but not Y247F-PKG-1α transfected PASMC. The transfection efficiency in the PASMC was approximately 20%.

Figure 17C:
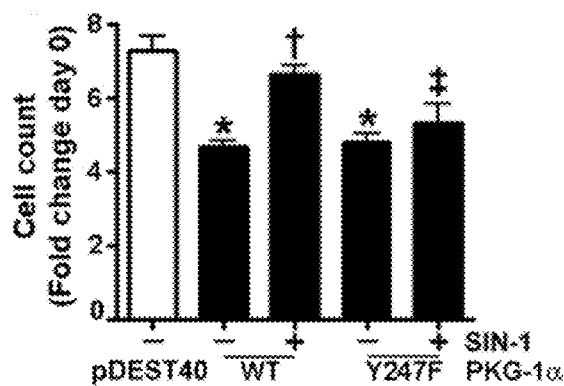
Figure 17D:
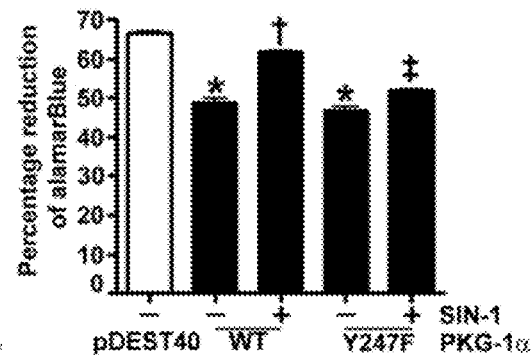

In conclusion, the results demonstrated that PASMC transfected with either WT- or Y247F-PKG-1α had lower cell counts and metabolic activity compared to those transfected with the parental vector, pDEST40. SIN-1 exposure induced proliferation and metabolic activity in the PASMC expressing WT-PKG-1α but not in the cells transfected with the Y247F-PKG-1α mutant (FIGS. 17C and 17D).

Example 10

Nitration Alters the Phenotype of Pulmonary Arterial Smooth Muscle Cells

Materials and Methods
Western Blot Analysis
Cells were prepared as previously described (Sud, N., et al., *American Journal of Physiology* 293, L1444-1453 (2007); Sharma, S., et al., *American Journal of Physiology* 294, L46-56 (2008)). Briefly, the cellular protein extracts were prepared by homogenizing the cells in lysis buffer (50 mM Tris-HCl, pH 7.6, 0.5% Triton X-100, and 20% glycerol) containing Halt protease inhibitor cocktail (Pierce, Rockford, Ill.). The extracts were then clarified by centrifugation (20,000 g for 20 min at 4° C.). The supernatant fractions were assayed for protein concentration using the Bio-Rad DC Protein Assay (Bio-Rad Laboratories, Hercules, Calif.) and used for Western blot analysis. Similarly, peripheral lung tissue from the control lambs and the lambs with pulmonary hypertension secondary to increased pulmonary blood flow (shunt) was prepared as described earlier (Aggarwal, S., et al., Journal of Cellular Physiology (2011)). Cell extracts (25 mg) were resolved using 4-20% Tris-SDS-Hepes PAGE, electrophoretically transferred to Immuno-Blot™ PVDF membrane (Bio-Rad Laboratories, Hercules, Calif.), and then blocked with 5% nonfat dry milk in Tris buffered saline. The membranes were then probed with antibodies against PKG-1α (1:500 dilution), anti-nitrotyrosine 247-PKG-1α (1:500), Calponin-1 (1:500 dilution), Vimentin (1:500 dilution), or MYH (1:500 dilution). Reactive bands were visualized using chemi-luminescence (Pierce Laboratories, Rockford, Ill.) on a Kodak 440CF image station. The band intensity was quantified using Kodak 1D image processing software. The protein expression was normalized by re-probing with anti β-actin (1:2000).

Immunocytochemistry

Semi-confluent PASMC grown on a coverslip in a 6-well plate were transfected with a mammalian expression plasmid containing either a wild-type (WT)- or Y247F-PKG-1α cDNA. After 20 h, the cells were serum starved (1% FBS) for 4 h then exposed or not to SIN-1 (500 µM) for 48 h. The cells were washed with PBS, methanol fixed (5 min), and permeabilized in 0.1% PBS-Tween (20 min). The cells were then washed 3× with PBS and blocked for non-specific protein-protein interactions with 1% BSA in PBS (1 h). The antibodies, smooth muscle (SM) 22-α (5 µg/ml) or proliferating cell nuclear antigen (PCNA) (1 µg/ml) diluted in 1% BSA in PBS, were added and incubated overnight at 4° C. The cells were again washed 3× with PBS and incubated in secondary antibody (green): Alexa Fluor 488 goat anti-mouse IgG (H+L) (1/1000 dilution) for PCNA or Alexa Fluor 488 donkey anti-goat IgG (H+L) (1/1000 dilution) for SM22-α for 1 h in the dark. DAPI was used to stain the cell nuclei (blue) at a concentration of 0.5 µg/ml for 3 min. The cells were rinsed 3× with PBS, and the coverslips were mounted on the slides with ProLong Gold Antifade and analyzed with the use of a Nikon Eclipse TE 300 inverted fluorescent microscope with a 60× oil objective and a Hamamatsu digital camera.

Results

To assess the effect of nitration on pulmonary arterial smooth muscle cell (PASMC) phenotype, PASMC were transiently transfected with expression plasmids containing WT-PKG-1α, Y247F-PKG-1α, or PDEST40 (as a control) for 20 h. Cells were then exposed or not to SIN-1 (500 µM, 48 h) and the effect on synthetic and contractile markers determined. The levels of myosin heavy chain (MYH, FIG. 18A), Calponin-1 (FIG. 18B), and Vimentin (FIG. 18C) were determined. The blots were then stripped and re-probed for β-actin to normalize for protein loading. PASMC were also subjected to immunohistochemistry using antibodies to SM22-α (5 µg/ml) and PCNA (1 µg/ml). Relevant secondary antibodies linked to Alexa Fluor 488 (green) were then applied. DAPI was also used to stain (blue) the cell nuclei.

In addition to its role in mediating the vasodilator effects of NO, PKG contributes to the maintenance of a contractile-like phenotype in SMC, and the suppression of PKG expression/activity in vitro induces a more synthetic, dedifferentiated phenotype (Lincoln, T., et al., Acta Physiologica Scandinavica 164, 507-515 (1998)). The transition of VSMC from a contractile to a proliferative phenotype appears to be an early event in various pathologies, such as pulmonary hypertension, atherosclerosis, and restenosis (Negash, S., et al., American Journal of Physiology 297, H304-312 (2009); Acampora, K. B., et al., Annals of Vascular Surgery 24, 116-126; Dusserre, E., et al., Biochimica Et Biophysica Acta 1212, 235-244 (1994)), and is associated with increased oxidative and nitrosative stress (Klemm, D. J., et al., Journal of Cardiovascular Pharmacology 58, 181-191; Madamanchi, N. R., et al., Arteriosclerosis, Thrombosis, and Vascular Biology 25, 950-956 (2005); Wang, J. N., et al., Free Radical Biology & Medicine 52, 173-181). Although the precise mechanisms by which oxidative stress induces a proliferative phenotype are still unresolved, reactive oxygen and nitrogen species (ROS and RNS) have been shown to attenuate PKG-1α signaling in both experimental and human forms of pulmonary hypertension as a result of diminished catalytic activity (Aggarwal, S., et al., Journal of Cellular Physiology (2011); Zhao, et al., The Journal of Clinical Investigation 119, 2009-2018 (2009)) or protein expression (Negash, et al., American Journal of Physiology 293, L1012-1020 (2007)). Protein nitration is emerging as an important posttranslational event responsible for attenuating PKG-1α activity. ROS and RNS levels are increased in pulmonary hypertensive mice (Nisbet, R. E., et al., American Journal of Respiratory Cell and Molecular Biology 40, 601-609 (2009)), lambs (Aggarwal, S., et al., Journal of Cellular Physiology (2011)), and humans (Zhao, et al., The Journal of Clinical Investigation 119, 2009-2018 (2009)) and the increase in oxidative and nitrosative stress is implicated in both vasoconstriction (Broughton, B. R., et al., American Journal of Physiology 298, L232-242) and vascular remodeling (Nozik-Grayck, E., et al., Advances in Experimental Medicine and Biology 618, 101-112 (2007)).

Studies have identified nitration and the ensuing attenuation of PKG-1α activity in the lungs of lambs with pulmonary hypertension secondary to increased pulmonary blood flow and in lambs with rebound pulmonary hypertension associated with the acute withdrawal of inhaled NO therapy (Aggarwal, S., et al., Journal of Cellular Physiology (2011)). In addition, the nitration and subsequent attenuation of PKG activity in the right ventricle (RV) appears to be responsible for the deterioration of RV function in a mouse model of PH induced by chronic hypoxia (Cruz, 3. A., et al., American Journal of Physiology 302, H2518-2527). While the increase in protein nitration associated with hypoxia reduces PKG activity through changes at the transcriptional and post-translational levels (Negash, et al., American Journal of Physiology 293, L1012-1020 (2007)). The clinical relevance of PKG nitration has also been shown by the observation that patients with idiopathic pulmonary arterial hypertension have increased PKG nitration in their lungs with no noticeable alteration in PKG protein levels (Zhao, et al., The Journal of Clinical Investigation 119, 2009-2018 (2009)). Thus, the accumulated data indicate that the nitration-dependent impairment of PKG activity is an important event in the development of vascular dysfunction in pulmonary hypertension.

Therefore, the effect of Y247 nitration was examined in vitro and in vivo.

Figure 18A:
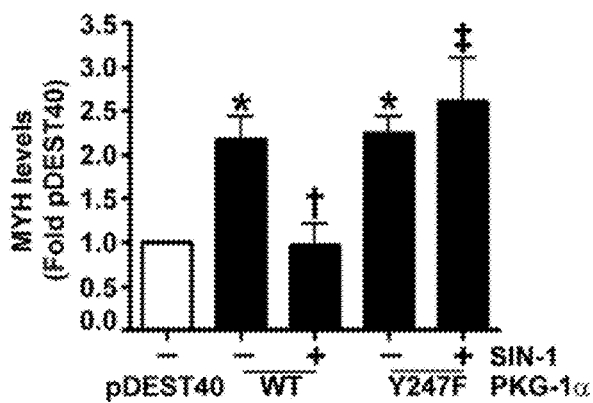
FIGS. 18A-E are histograms showing (A) MYH levels (Fold pDEST40); (B) Calponin-1 levels; (C) Vimentin levels (Fold pDEST40); (D) % Filamentous SM22-α positive PASMC; and (E) % PCNA positive nuclei, respectively, for control plasmid (pDEST40, white bar), wild type PKG-1α (WT) and Y247F PKG-1α(Y247F), with or without SIN-1, respectively. Data are mean±SEM, n=4-7, *p<0.05 vs. pDEST40, † p<0.05 vs. WT-PKG-1α, ‡ p<0.05 vs. WT-PKG-1α+SIN-1.
Figure 18B:
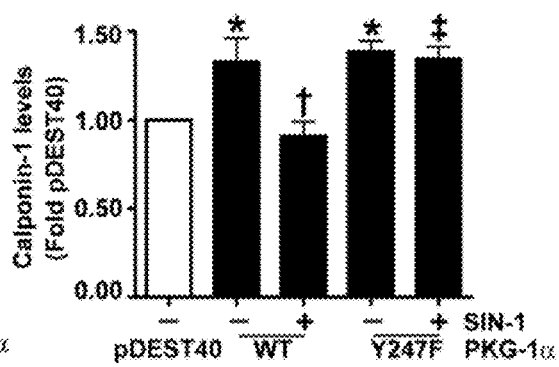
Figure 18C:
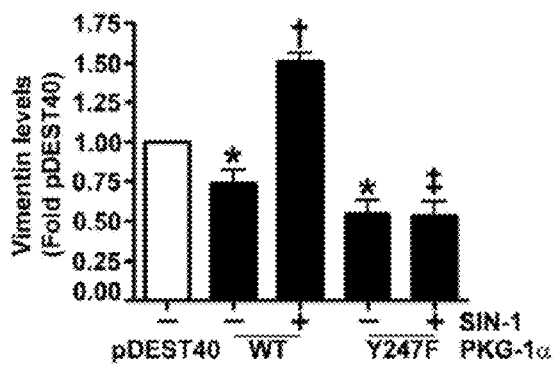
Figure 18D:
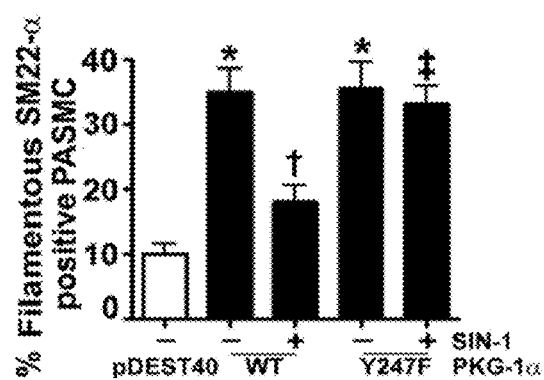

Immunoblot analysis demonstrated that PASMC transfected with WT and Y247F-PKG-1α exhibited a contractile phenotype, as illustrated by the increased levels of the contractile markers: MYH and Calponin-1 (FIGS. 18A and 18B) and decreased levels of the proliferative marker, Vimentin (FIG. 18C). However, when exposed to SIN-1, WT-PKG-1α expressing PASMC acquired a more proliferative phenotype compared to the cells transfected with the Y247F-PKG-1α mutant (FIGS. 18A-C). The immunocytochemistry analysis also found that the PASMC transfected with the WT- and the Y247F-PKG-1α were spindle shaped and had increased expression of contractile phenotype marker, SM22-α, bound to actin stress fibers (FIG. 18D). In contrast, the nuclear levels of the proliferative marker protein, PCNA, were decreased (FIG. 18E) in these cells. SIN-1 treatment attenuated SM-22α expression and increased PCNA staining in the WT- but not in the Y247F-PKG-α expressing cells indicating that the Y247F-PKG-α mutant is resistant to phenotype modulation by nitrosative stress.

Figure 18E:
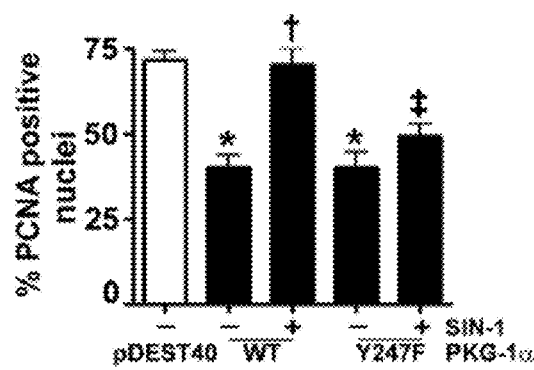

In conclusion, under basal conditions, PASMC transfected with the WT- and the Y247F-PKG-1α exhibited increased expression of the contractile markers, MYH and Calponin-1 and decreased expression of the proliferative marker, Vimentin indicative of a contractile phenotype. SIN-1 decreased the expression of the contractile markers, MYH and Calponin-1 and increased the expression of the proliferative marker, Vimentin in the WT-PKG-1α transfected cells, indicative of a proliferative phenotype. The Y247F PKG-1α expressing cells were resistant to this phenotypic conversion. PASMC expressing WT- or Y247FPKG-1α acquired a contractile phenotype with the increased filamentous binding of the SM22-α protein on the actin stress fibers (FIG. 18D). The nuclear localization of PCNA was also reduced in these cells (FIG. 18E). However, when PASMC were treated with SIN-1, the WT PKG-1α expressing cells exhibited decreased filamentous SM22-α expression and increased nuclear staining of PCNA, while the Y247F-PKG-1α expressing cells were unaffected.

Example 11

Y247-PKG-1α Nitration Occurs in vitro and in vivo

Materials and Methods

Immunohistochemistry and Immunofluorescence Microscopy

Normal and pulmonary hypertensive (PH) human lung tissue paraffin sections (5 μm) were mounted on slides and placed in a 55° C. oven for ten minutes, deparaffinized in xylene (3×, 5 min), then hydrated using an alcohol series-100%, 95%, 70% alcohol (each 3×, 5 min) and finally rinsed in water. The sections were processed for antigen retrieval by boiling the slides in 10 mM Citrate Buffer (pH 6.0). The slides were then cooled at room temperature for 20 minutes, washed in PBS and blocked in 10% normal serum overnight at 4° C. Immunofluorescence was then performed on serial sections from each group using goat anti-PKG-1α, rabbit anti-3-NT-Y247-PKG-1α, and mouse anti-caldesmon antibodies (Sigma). The sections were incubated with primary antibodies for 1 h at room temperature and washed (3×, 5 min) with PBS. Subsequently, sections were double stained either with Alexa Fluor® 546 anti-goat or anti-rabbit secondary antibodies (Molecular Probes, Inc.) and Alexa Fluor® 488 anti-mouse secondary antibodies. Sections were washed several times in PBS, mounted on the cover slip in anti-fading aqueous mounting medium. The fluorescent-stained sections were then analyzed using the appropriate excitation and emission wavelengths by performing confocal microscopy using a computer-based DeltaVision imaging system (Applied Precision Inc.).

Lamb Model of Pulmonary Hypertension

The surgical preparation to introduce fetal aorta-pulmonary shunt was carried out as previously described (Reddy, V. M., et al., *Circulation* 92, 606-613 (1995)). All protocols and procedures were approved by the Committee on Animal Research at the University of California, San Francisco and the Institutional Animal Care and Use Committee at Georgia Regents University.

Human Specimens

Four bilateral lung explants were selected from human patients who underwent lung transplantation because of Eisenmenger's syndrome ("associated pulmonary arterial hypertension", NYHA IV). All lung specimens showed prominent plexiform vasculopathy (age at transplantation: 36.5±11.04 years; female:male ratio—4:1). All the specimens were inflated with formalin via the main bronchi and were formalin-fixed overnight before being extensively sampled and paraffin-embedded (FFPE). Subsequently, they were histologically evaluated, graded according to the Heath-Edwards classification (all grade 5), and correlated with clinical data to confirm the (histopathologic) diagnosis. The FFPE samples were retrieved from the archives of the Institute of Pathology of Hannover Medical School and were handled anonymously, following the requirements of the local ethics committee (Jonigk, D., et al., *The American Journal of Pathology* 179, 167-179).

Cell Culture

Primary cultures of pulmonary artery smooth muscle cells (PASMC) from 4-week old lambs were isolated by the explant technique, as previously described (Wedgwood, S., et al., *Circulation Research* 89, 357-364 (2001)). Briefly, a segment of the main pulmonary artery from a 4-week old lamb was excised and placed in a sterile 10 cm dish containing DMEM supplemented with 1 gm/l glucose. The segment was stripped of adventitia with a sterile forceps. The main pulmonary artery segment was then cut longitudinally to open the vessel, and the endothelial layer was removed by gentle rubbing with a cell scraper. The vessel was then cut into 2 mm segments, inverted, and placed on a collagen coated 35 mm tissue culture dish. DMEM (~50 μl) containing 10% FBS (Hyclone), antibiotics, and antimycotics (MediaTech) was then added to each segment, and the cells were grown overnight at 37° C. in a humidified atmosphere with 5% $CO_2$ and 95% air. The next day an additional 2 ml of medium was added. The growth medium was subsequently changed every 2 days. When SMC islands were observed under the microscope, the tissue segment was removed, and the individual cell islands were sub-cloned using cloning rings. The identity of PASMC was confirmed by immunostaining (>99% positive) with SMC actin, caldesmon, and calponin. All cultures for subsequent experiments were maintained in DMEM supplemented with 10% FBS, 1% antibiotics, and antimycotics at 37° C. in a humidified atmosphere with 5% $CO_2$ and 95% air. All experiments were conducted in cells between passages 5 and 15.

Results

PASMC were transiently transfected with expression plasmids containing WT- or Y247FPKG-1α for 48 h. Cells were then treated or not with SIN-1 (500 μM, 30 min). An anti-Y247-PKG-1α antibody was developed to directly analyze the nitration of Y247 in cells and tissues. Protein extracts were immunoblotted and probed with antibody raised against 3-NT-Y247-PKG-1α. The blots were then stripped and re-probed for total β-actin to normalize loading. Immunohistochemcial analysis was performed on lung sections prepared from humans with pulmonary hypertension (PH). The antibodies used were goat anti-PKG-1α (red), 3-NT-Y247-PKG-1α (red), and anti-caldesmon (green). The fluorescent-stained sections were analyzed using confocal microscopy.

Figure 19A:
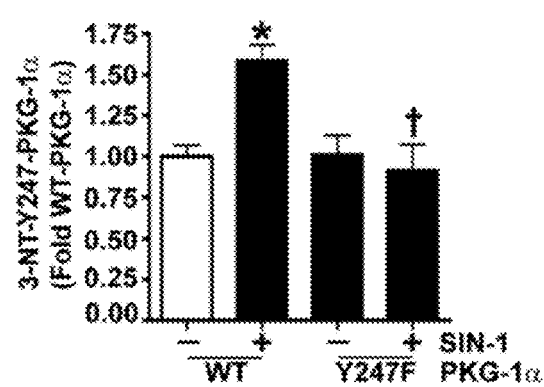
FIGS. 19A-C are histograms showing (A) 3-NT-Y247-PKG-1α levels (Fold WT-PKG-1α) of wild type PKG-1α (WT) and Y425F PKG-1α (Y247F), respectively, with or without SIN-1; and (B) shows 3-NT-Y247-PKG-1α levels (Fold control) of lambs, without (Control) and with pulmonary hypertension secondary to increased pulmonary blood flow (Shunt), respectively.
Figure 19B:
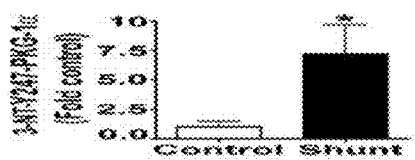
Figure 19C:
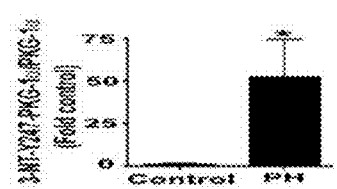

WT-PKG-1α nitration was significantly increased in the presence of SIN-1 in PASMC (FIG. 19A). However, there were no significant increases in the nitration levels of 3-NT-Y247-PKG-1α in the presence of SIN-1 (FIG. 19A). The 3-NT-Y247-PKG-1α antibody also detected higher PKG-1α nitration levels in peripheral lung tissues of lambs with pulmonary hypertension secondary to increased pulmonary blood flow (FIG. 19B). The 3-NT-Y247-PKG-1α antibody identified significantly higher levels of nitrated PKG-1α in the lungs of patients with PH and this was predominant in the smooth muscle layer (FIG. 19C).

In conclusion, using immunoblot analysis, anti-Y247-PKG-1α antibody detected: higher levels of nitrated PKG-1α in PASMC transfected with WT-PKG-1α compared to Y247F-PKG-1α with SIN-1 treatment (FIG. 19A). This antibody also detected high levels of Y247 nitration in the peripheral lung tissue of lambs with pulmonary hypertension secondary to increased pulmonary blood flow (FIG. 19B) confirming the results of earlier studies (Aggarwal, S., et al., *Journal of Cellular Physiology* (2011)). Further, immunohistochemical analysis identified greater signal in the pulmonary vessels from patients suffering from idiopathic pulmonary hypertension (Zhao, et al., *The Journal of Clinical Investigation* 119, 2009-2018 (2009)) compared to controls (FIG. 19C). Together these data indicate that the nitration of Y247 is an important mechanism by which nitrative stress impairs PKG-1α activity both in vitro and in vivo.

Example 12

Generation of a Homology Model of Human PKG-1α

Materials and Methods
Generation of the Homology Model

The YASARA Structure version has a complete homology modeling module that performs automatically all the steps from amino acid sequence (input) to a refined high resolution model (output). The PKG-1α homology model was obtained using the following protocol. A PSI-BLAST (Altschul, S. F., et al., *Nucleic Acids Research* 25, 3389-3402 (1997)) integrated in YASARA was used to identify the closest templates in the PDB. As a template for the 3-dimensional structure for the PKG-1α homology model, regulatory (PDB 1NE4) and catalytic (PDB 2CPK) domains of PKA were used because PKA shares significant structural and functional similarities to PKG-1α. BLAST was used to retrieve homologous sequences, create a multiple sequence alignment, and enter the sequences into a 'Discrimination of Secondary Structure Class (DSC)' prediction algorithm (King, R. D., et al., *Protein Sci.* 5, 2298-2310 (1996)).

The side-chains were added and optimized in the next step, and all of the newly modeled parts were subjected to a combined steepest descent and underwent simulated annealing minimization. The backbone atoms of the aligned residues were kept fixed to avoid potential damage. Finally, an unrestrained, simulated, annealing minimization with water was performed on the entire model. The resultant individual homology models of the PKG-1α regulatory domain and the catalytic domain were combined together to form a single PDB sequence. This sequence was used as a template sequence for generating a complete homology model of PKG-1α using the procedure described above resulting in a PKG-1α structure containing two cGMP binding sites: A and B as well as an ATP binding site represented by β-sheets.

Subsequently, docking of two cGMP molecules and one ATP molecule to their respective binding sites was performed. A simulation cell was placed around each ligand binding site on the PKG-1α homology model to focus the docking of the specific ligand on the known specific binding regions. The AutoDock program, developed at the Scripps Research Institute, was used to dock the ligands. A $NO_2$ group was introduced into the protein model on the ortho carbon of the phenolic ring of the Y247 residue. The structure was minimized, and the hydrogen bonding energy (kJ/mol) and distance [Angstrom (Å)] between the cGMP molecule and the cGMP binding site B of PKG-1α were analyzed in the presence or absence of the $NO_2$ group again using YASARA.

Results

To further understand the molecular mechanism(s) by which nitration of Y247 impairs PKG-1α activity, a homology model of full length PKG-1α protein was developed. Since a complete X-ray structure for PKG-1α is unavailable in the protein data bank (PDB), the structure's homology modeling module of YASARA (Yet Another Scientific Artificial Reality Application) were used (Venselaar, H., et al., *Eur. Biophys. J* 39, 551-563) to build a high resolution model of PKG-1α from its amino acid sequence. Due to the labile structure of PKG-1 only the dimerization region in the regulatory domain in PKG-1β (Casteel, D. E., et al., *The Journal of Biological Chemistry* 285, 32684-32688), and the regulatory domains of PKG-1α (amino acids 78-355) (Osborne, B. W., et al., *Structure* 19, 1317-1327) and PKG-1β (amino acids 92-227) (Kim, J. J., et al., *PloS One* 6, e18413) have been crystallized and characterized. Therefore, the known crystal structures of the regulatory (PDB 1NE4) and the catalytic (PDB 2CPK) domains of PKA were used as templates to build a homology model. The YASARA homology modeling software was used to build a homology model of the PKG-1α regulatory domain using the known crystal structure of the PKA regulatory domain (PDB 1NE4), as a template. The known crystal structure of the catalytic domain of PKA (PDB 2CPK) was used to construct the corresponding homology model of the catalytic domain of PKG-1α. Using the homology models of these two domains of PKG-1α, a complete 3-dimensional model of the protein was generated. The AutoDock program was then used to dock two cGMP molecules to the cGMP binding sites: A and B and an ATP molecule to the ATP binding site.

Figure 20A:
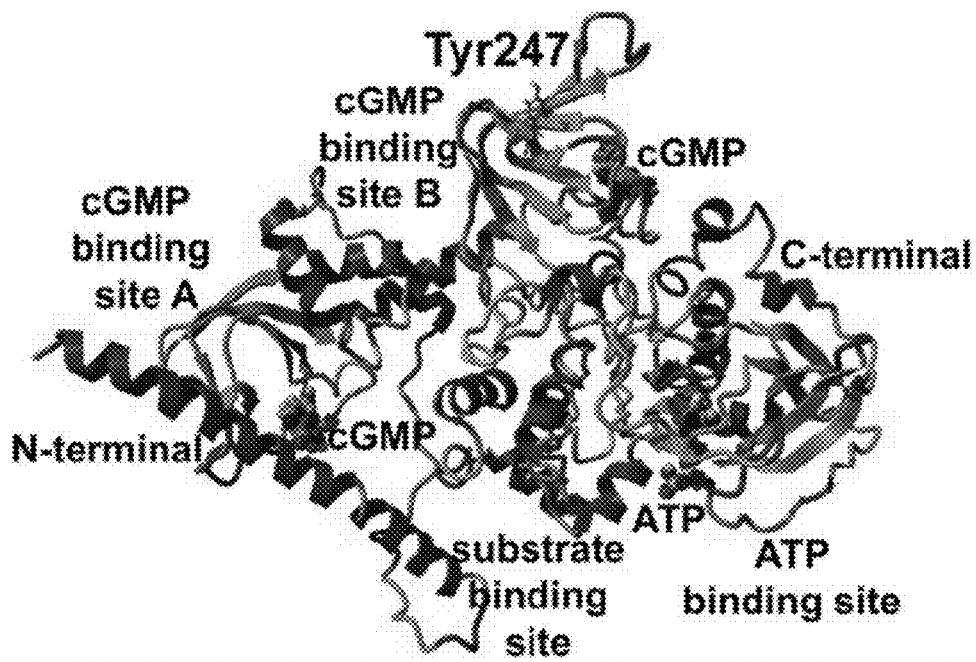
Figure 20B:
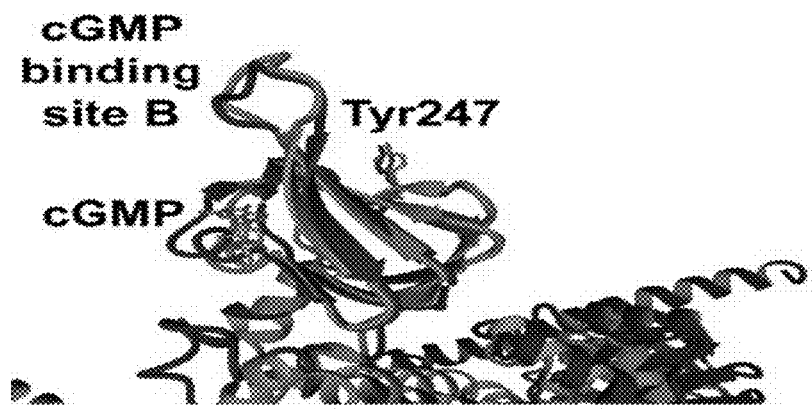

The analysis of the resulting 3-dimensional PKG-1α structure indicated that Y247 shares a close proximity to the cGMP binding site B (FIG. 20A). Further, the superimposition and comparison of the recently crystallized structure of PKG-1α (Osborne, B. W., et al., *Structure* 19, 1317-1327) and the homology model demonstrated high similarity within the cGMP binding site B, even though this crystal structure was not used to build the homology model (FIG. 20B). Further, molecular dynamic simulations in the model after the addition of a $NO_2$ group to the Y247 predicted the loss of a hydrogen bond between the cGMP molecule and threonine 302 of PKG-1α, the residue responsible for nucleotide specificity of cGMP binding site B (FIG. 20C). The YASARA homology modeling software was used to predict the affinity of cGMP for the cGMP binding site B in the PKG-1α homology model under control (FIG. 20C) and nitrative stress conditions (FIG. 20D). The $NO_2$ group was predicted to displace the hydrogen bond between cGMP and glutamate 292 and form a new hydrogen bond between cGMP and arginine 282 of PKG-1α (FIG. 20D). The addition of a $NO_2$ group to Y247 is predicted to decrease the total hydrogen bonding energy between cGMP and PKG-1α from 91.93 kJ/mol to 54.02 kJ/mol (FIGS. 20C-D).

In conclusion, the nitration of Y247 should result in a net loss of 1 hydrogen bond between cGMP and PKG-1α and an increase in bond lengths with a predicted net decrease in total hydrogen bonding energy between cGMP and PKG-1α from 91.93 kJ/mol to 54.02 kJ/mol (FIGS. 20C-D).

Example 13

Nitrative Stress Affects cGMP Binding and Dissociation Characteristics of PKG-1α

Materials and Methods

Measurement of PKG Catalytic Activity Total PKG activity was determined using a non-radioactive immunoassay in cell lysates, according to the manufacturer's directions. Briefly, protein samples were diluted in kinase reaction buffer containing $Mg^{2+}$ and ATP (125 µM) in the presence or absence of 8-Br cGMP (10 µM) and incubated in a 96 well plate pre-coated with a PKG substrate containing threonine residues phosphorylated by PKG.

After incubation for 30 min at 30° C. to allow the phosphorylation of the bound substrate, an HRP conjugated anti-phosphothreonine specific antibody was added to convert a chromogenic substrate to a colorimetric substrate that was subsequently read spectrophotometrically at 450 nm. The change in absorbance reflected the relative activity of PKG in the sample. The results were reported as pmols of phosphate incorporated into the GST-G substrate fusion protein by active PKG in the sample in the presence or absence of cGMP (10 µM) per minute at 30° C. per µg of protein (pmol/min/µg). These results were extrapolated by comparing the spectrophotometrical values of the samples to the known activity (pmol/min) of recombinant PKG-1α protein, as a positive control. The kinetic constants were determined using nonlinear regression (curve fit) analysis (GraphPad Prism Software Inc).

To determine the Michaelis-Menten constant (Km) for cGMP, the kinase assay was performed, as mentioned above; however, the cGMP concentration was titrated from 0-10 µM, while the ATP concentration remained constant at 125 µM.

[$^3$H]cGMP Binding Assay

HEK-293T cells were transiently transfected with either the WT-PKG-1α or the Y247FPKG-1α cDNA using Effectene transfection reagent (Qiagen), according to the manufacturer's instructions. Briefly, the cells were split the day before the transfection to low cell densities (25%) and were transfected 24 h later. After 48 h of transfection, the cells were incubated in DMEM serum free media containing 1% FBS and antibiotics for 4 h and then treated with or without SIN-1 (500 µM), for 30 min. This method produced an approximate 70% transfection efficiency of HEK-293T cells, as measured using green fluorescent protein vectors.

In order to purify PKG-1α, three 10 cm dishes of cells were transfected for each purification group. After treatment with SIN-1, the cells were placed on ice, the media was aspirated, and replaced with 10 ml of ice cold PBS. All subsequent steps were performed on ice. The cells were scraped and clarified by centrifugation. The cell pellets were resuspended (1 ml/10 cm dish) in lysis buffer (50 mM Tris-HCl, pH 7.0, 1 mM EDTA, 1% Nonidet P-40, 150 nM NaCl) containing phosphatase and protease inhibitor cocktails for 20 min at 4° C. followed by clarification by centrifugation at 20,000 g for 20 min.

The batches of supernatant were pooled, and 2 µg of anti-PKG-1α antibody per mg of protein were added to the extract and rocked at 4° C. After 4 h of incubation, protein G PLUS-agarose beads (10 µl/mg protein) were added and incubated overnight with nutation at 4° C. The beads were washed three times in lysis buffer. The PKG-1α attached to the beads was then eluted by the resuspension in 100 µl of PBS containing 5 µg of PKG-1α peptide (Santa Cruz Biotechnology) per µg of antibody. After 15 min of agitation at 4° C., the beads were pelleted by centrifugation, and the supernatant containing the PKG-1α protein was collected, quantified using Bradford reagent, and stored at −80° C.

To assay the binding of cGMP to WT- and Y247F-PKG-1α the enzymes were saturated with cGMP by incubating 50 µl aliquots of the diluted PKG constructs for 60 min at room temperature with 50 µl of [$^3$H]cGMP and 150 µl of cGMP-binding assay mixture (25 mM $K_2HPO_4$, 25 mM $KH_2PO_4$, 1 mM EDTA, pH 6.8, 2M NaCl, 200 µM 3-isobutyl-1-methylxanthine). The final cGMP concentration varied from 0 to 200 nM, and the final concentration of enzyme was 100 ng. After incubation, 2 ml of cold aqueous saturated $(NH_4)_2SO_4$ was added to each sample. The samples were then filtered onto 0.45 µm pore nitrocellulose paper (Millipore) that had been pre-moistened with saturated $(NH_4)_2SO_4$ and were then rinsed three times with 2 ml of cold saturated $(NH_4)_2SO_4$. The papers were dried and shaken in vials containing 1.5 ml 2% SDS. Aqueous scintillant (10 ml) was added; the vials were shaken again and then counted in a liquid scintillation counter. The dissociation constant (Kd) values were determined using GraphPad Prism graphics.

[$^3$H]cGMP Dissociation/Exchange Assay

WT- and Y247F-PKG-1α were immunopurified, as described above then incubated for 60 min at room temperature with 3 ml of cGMP-binding assay mixture containing 3 µM [$^3$H]cGMP. This incubation time and dose has been previously experimentally determined to be adequate for the saturation of the cGMP-binding sites in PKG. After incubation, the samples were cooled to 4° C. and divided into 200 µl aliquots per tube. The addition of 100-fold excess unlabeled cGMP at time 0 sec (Bo) initiated the dissociation (exchange) of the bound [$^3$H]cGMP. The cGMP exchange in each tube was stopped at the appropriate time point by the addition of 2 ml of cold aqueous saturated $(NH_4)_2SO_4$. The samples were filtered, washed, and the portion of bound [$^3$H]cGMP at any time point was determined, as described previously.

Results

To test the predictions made by the homology model, the influence of nitrative stress on the affinity of PKG-1α for cGMP were assessed by performing [$^3$H]cGMP binding studies. PASMC were transiently transfected with expression plasmids containing WT-PKG-1α or Y247F-PKG-1α for 48 h. The cells were then serum starved for 4 h then exposed or not to SIN-1 (500 µM, 30 min) and PKG-1α immunoprecipitated. The PKG protein was immunopurified and assays were performed in the presence of increasing concentrations of [$^3$H]cGMP. Immunoprecipitated WT-PKG-1α and Y247F-PKG-1α protein (100 ng) was analyzed in a [$^3$H]cGMP binding assay (FIG. 21A) and a [$^3$H]cGMP dissociation assay (FIG. 21B). In the dissociation assay a 100-fold excess of unlabeled cGMP was added at time 0 sec (Bo) to initiate the dissociation (exchange) of bound [$^3$H]cGMP. The reaction was stopped with cold aqueous saturated (NH4)2SO4 at various time points. The results were plotted as ln(B/Bo) with Bo as the initial [[$^3$H]cGMP bound] and B as the [[$^3$H]cGMP remaining bound] at various time points. Enzyme kinetics were also determined using varying concentrations of cGMP (0-10 µM). The change in the enzyme activity for each concentration of cGMP was plotted in pmol/min/µg protein using nonlinear regression (curve fit) analysis.

In the absence of SIN-1, the cGMP-binding stoichiometry of the Y247F-PKG-1α mutant was comparable with that of the WT-PKG-1α (FIG. 21A). However, the Kd values obtained for the WT-PKG-1α after SIN-1 treatment were higher than those obtained from the SIN-1 treated Y247F mutant (FIG. 21A, Table 5). The Kd values derived from these experiments were an average affinity of the two cGMP-binding sites within PKG-1α, and the binding characteristics of the individual sites, A and B, could not be assessed. To further confirm these results, a second measure of affinity was performed using cGMP exchange/dissociation analysis of the WT- and the Y247F-PKG-1α.

In the absence of SIN-1, the results demonstrated that the [$^3$H]cGMP exchange/dissociation was biphasic (rapid vs. slow exchange) in the WT- and in the Y247F-PKG-1α dissociation curves, consistent with the presence of two kinetically distinct cGMP binding sites (sites A and B). However, SIN-1 exposure enhanced [$^3$H]cGMP exchange/dissociation from the WT-PKG-1α but not from the Y247F mutant (FIG. 21B, Table 5). Further, SIN-1 decreased the dissociation/exchange rate (t½), or the time required for cGMP to dissociate from half the binding sites on PKG-Iα in the WTPKG-1α, from 27.06 s to 14.22 s, while no change was observed in the Y247F mutant (Table 5).

The cGMP binding and dissociation studies indicated that the phosphotransferase reaction catalyzed by PKG-1α may require a higher concentration of cGMP to reach the maximum velocity (Vmax) under nitrative stress. Therefore, Michaelis-Menten kinetics were performed to determine the cGMP concentrations required for PKG-1α to achieve half of the maximum velocity (Km). Utilizing a nonlinear regression curve it was demonstrated that, at constant ATP levels (125 µM) and varying cGMP concentrations (0-10 µM), SIN-1 challenge decreased the Vmax of the reaction of the WT-, but not of the Y247F mutant, PKG-1α from 0.47 to 0.28 pmols/min/µg protein (FIG. 21C and Table 5). Further, the results showed that the Michaelis-Menten constant (Km) increased from 2.73 to 8.91 nM for cGMP in the WT-PKG-1α upon SIN-1 treatment, while no significant change was observed in the Y247F mutant (FIG. 21C and Table 5).

TABLE 5

|  | $K_d$ (nM) | $T_{1/2}$ (s) | $V_{max}$ (pmol/min/µg) | $K_m$ (nM) |
|---|---|---|---|---|
| WT-PKG-1α | 21.34 ± 2.2 | 27.06 | 0.47 ± 0.02 | 2.73 ± 0.99 |
| WT-PKG-1α + SIN1 | 32.12 ± 5.5 | 14.22 | 0.28 ± 0.01 | 8.91 ± 2.69 |
| Y247F-PKG-1α | 20.43 ± 2.8 | 26.02 | 0.47 ± 0.02 | 2.43 ± 1.03 |
| Y247F-PKG-1α + SIN1 | 21.54 ± 3.4 | 23.79 | 0.42 ± 0.01 | 3.26 ± 0.99 |

In conclusion, SIN-1 treatment significantly attenuated maximal [$^3$H]cGMP binding to WT-PKG-1α, but not to the Y247F-PKG-1α mutant (FIG. 21A). SIN-1 treatment enhanced the dissociation/exchange of [$^3$H]cGMP from WT-PKG-1α, but not from Y247F-PKG-1α (FIG. 21B). The maximum velocity (Vmax) of the phosphotransferase reaction of WT-PKG-1α, but not Y247F-PKG-1α, was significantly decreased with SIN-1 exposure (FIG. 21C).

Tyrosine nitration is a selective process as not all tyrosine residues in a protein undergo nitration under patho-physiological conditions (Ischiropoulos, H., *Biochemical and Biophysical Research Communications* 305, 776-783 (2003)). PKG-1α has 21 tyrosine residues in its monomeric structure, of which 9 tyrosines are located in the regulatory domain and 12 are part of the catalytic domain. Using MS and mutational studies discussed above, it was discovered that nitration of tyrosine 247, located within the cGMP binding site B of the regulatory domain of PKG-1α, is responsible for the impaired kinase activity. Nitrative stress only decreased the cGMP dependent kinase activity, while basal PKG activity was unchanged.

Cyclic GMP binding to both sites A and B of PKG brings about a conformational change necessary for full kinase activity. The two cGMP binding sites share approximately 37% amino acid sequence similarity but differ in their cGMP binding kinetics (Corbin, J. D., et al., *The Journal of Biological Chemistry* 261, 1208-1214 (1986)). This difference may be due to the number of hydrogen bonds between cGMP and the cGMP binding sites on PKG as well as the length of these bonds (Kim, J. J., et al., *PloS One* 6, e18413). Molecular dynamic simulations using a full-length PKG-1α homology model predicted that the nitration of Y247 impairs hydrogen bonding between cGMP and the cGMP binding site B of the kinase. These results were confirmed by in vitro [$^3$H]cGMP binding studies and reveal a mechanism by which PKG is regulated by nitrative stress. The findings are also in agreement with other studies which have also shown that the negative charge imparted by nitration alters the hydrogen bonding network between the substrate and protein in such enzymes as manganese superoxide dismutase (MnSOD) (Redondo-Horcajo, M., et al., *Cardiovascular Research* 87, 356-365), glutathione reductase (Savvides, S, N., et al., *The Journal of Biological Chemistry* 277, 2779-2784 (2002)), and prostacyclin synthase (Nie, H., et al., *Diabetes* 55, 31333141 (2006)).

However, it should be noted that the results appear to be contradictory to a previous study that demonstrated that SIN-1 treatment decreased both basal and cGMP dependent PKG activity in VSMC (Zhao, et al., *The Journal of Clinical Investigation* 119, 2009-2018 (2009)). In this study single tyrosine to phenylalanine mutations of all tyrosine residues located in the catalytic domain of human PKG-1α were generated and Y345F- and the Y549F-PKG-1α mutants were found to be resistant to nitration dependent inhibition (Zhao, et al., *The Journal of Clinical Investigation* 119, 2009-2018 (2009)). Several differences between these studies may explain these apparently conflicting findings. Firstly, the presence of PKG-1β in VSMC may account for the decrease in the total basal PKG activity upon exposure to SIN-1 compared to PKG-1α expressed in Hek293 cells in the experiments. Secondly, Y345 in PKG-1α is located in the hinge/switch region (aa 328-355) between the regulatory and the catalytic domain, and acts as a tether for the catalytic domain (Osborne, B. W., et al., *Structure* 19, 1317-1327). Mutations in this switch region have been shown to cause the kinase to be more active, presumably independent of cGMP (Osborne, B. W., et al., *Structure* 19, 1317-1327). Finally, based on the homology model, Y549 of PKG-1α is located within the catalytic domain and interacts with the pseudo-substrate site, maintaining the enzyme in an auto-inhibited state (Francis, S. H., et al., *The Journal of Biological Chemistry* 271, 20748-20755 (1996); Heil, W. G., et al., *European Journal of Biochemistry/FEBS* 168, 117-121 (1987)). The auto-inhibition of PKG-1α is relieved by the conformational change caused by either cGMP binding or auto-phosphorylation, which disrupts the auto-inhibitory interaction between the regulatory and catalytic domains (Zhao, J., et al., *The Journal of Biological Chemistry* 272, 31929-31936 (1997); Chu, D. M., et al., *The Journal of Biological Chemistry* 273, 14649-14656 (1998); Chu, D. M., et al., *The Journal of Biological Chemistry* 272, 31922-31928 (1997)). The structural alterations resulting from the replacement of the tyrosine with a phenylalanine at residue 549 could result in a conformational change, thereby relieving this basal inhibition. Under both these circumstances the nitration of Y247 observed in the study would not influence the kinase activity of these PKG-1α mutants as the data indicate that the nitration of Y247 inhibits only the cGMP-inducible activation of PKG-1α.

In summary, Examples 7-13 indicate that the nitration of PKG-1α may be a common mechanism underlying vascular dysfunction in pulmonary hypertension and other disorders. This conclusion is supported by other studies (Negash, et al., *American Journal of Physiology* 293, L1012-1020 (2007); Zhao, et al., *The Journal of Clinical Investigation* 119, 2009-2018 (2009)). Examples 7-13 show that Y247 as the primary target of nitrosative stress and is responsible for the attenuation of PKG-1α catalytic activity. Further, increasing intracellular cGMP levels has been used as a management strategy in patients with multiple vascular abnormalities including inhaled NO therapy for pulmonary hypertension; NO donors, such as nitroglycerin, isosorbide dinitrate, or isosorbide mononitrate for coronary artery diseases; cGMP specific phosphodiesterase-5 inhibitors, sildenafil and tadalafil for the treatment of pulmonary hypertension and erectile dysfunction; and B-type natriuretic peptides for hypoxemic respiratory failure. The major goal of these therapies is to increase the production of cGMP or inhibit its breakdown and thereby increase vascular dilation. However, if the cellular levels of cGMP become too high this can interfere with normal cellular proliferation, cause DNA strand breaks, and/or base alterations that are potentially mutagenic (Weinberger, B., et *Toxicol Sci.* 59, 5-16 (2001)) Therefore, based on the data presented herein, it is believed that strategies aimed at minimizing PKG-1α nitration may have adjunct therapeutic value in the treatment of vascular disorders. These strategies may include cell or protein specific targeting of antioxidants, development of nitration site shielding peptides, or perhaps enhancing the autophosphorylation of PKG-1 to minimize the external requirement of cGMP for the enzyme activation.

Example 14

Generation of a PKG-Iα Shielding Peptide

Materials and Methods

Development and Analysis of a PKG-1α Shielding Peptide

Utilizing the PKG-Iα homology model and the docking module of Yasara a peptide that binds to the region of PKG-Iα surrounding Y247 was identified. A PKG-Iα activity assay was carried out using HLMVEC. Recombinant human PKG-Iα18 was exposed to the peroxynitrite generator, SIN-1 (200 μM, 10 min) with increasing concentrations of the shielding peptide (0-10 μg).

Results

Figure 22:
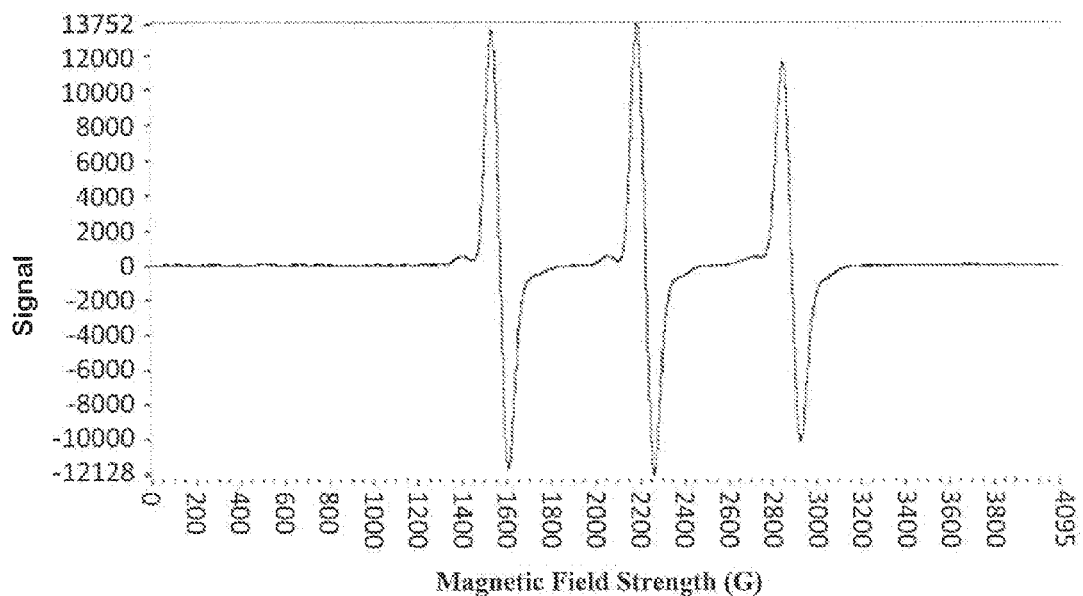
FIG. 22 is a line graph showing an electron paramagnetic resonance (EPR) spectroscopy trace for the peptide GAL-RQKNVK(X)-amide (SEQ ID:40), where X is 3-carboxy-2,2,5,5-tetramethyl-3-pyrrolin-1-yloxy (nitroxide).

The amino acid sequence of this peptide is GAL-RQKNVK(X)-amide (SEQ ID NO:29), where X is 3-carboxy-2,2,5,5-tetramethyl-3-pyrrolin-1-yloxy (nitroxide). The amide on C-terminal was added to remove the negative charge and enhance cell permeability. EPR analysis confirms the presence of the nitroxide (FIG. 22).

Figure 23:
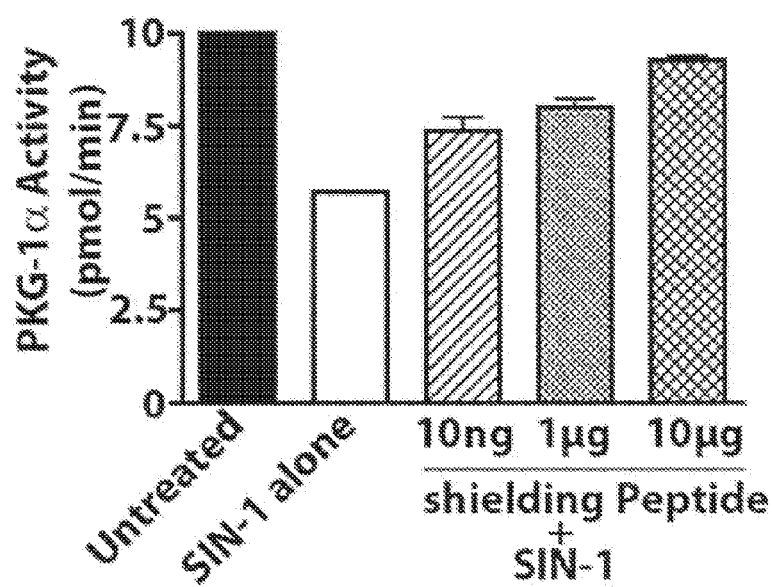
FIG. 23 is a histogram showing PKG-1α activity (pmol/min) for PKG-1α alone (Untreated), SIN-1 alone and for various concentrations (10 ng, 1 μg and 10 μg) of the shielding peptide with SIN-1, respectively. Data are Mean+SEM, N=2-3.

The results of a PKG-Iα activity assay show the shielding peptide preserves PKG-Iα activity against peroyxnitrite (FIG. 23). Data indicated that the PKG-Iα shielding peptide preserved barrier function when challenged with LPS and did not alter physiologic PKG-Iα activity, at least in vitro.

In conclusion, a shielding peptide prevented the nitration-mediated inhibition of PKG-1α. EPR analysis confirmed the nitroxide group. The shielding peptide dose-dependently preserved PKG activity.

We claim:

1. A nitration shielding peptide that reduces or prevents nitration of a protein of interest comprising a nitration shielding domain comprising
   SEQ ID NO:20, wherein the nitration shielding peptide has a nitroxide conjugated to at least one amino acid of the nitration shielding peptide and wherein the nitration shielding peptide is 11 to 15 amino acids in length.

2. The nitration shielding peptide of claim 1 wherein the nitration shielding domain is 11 amino acids in length.

3. The nitration shielding peptide of claim 1, further comprising a protein transduction domain, a targeting signal, a charge neutralizing moiety, or any combination thereof.

4. The nitration shielding peptide of claim 1, wherein the nitroxide is 3-carboxy-2,2,5,5-tetramethyl-3-pyrrolin-1-yloxy.

5. The composition of claim 1, wherein the nitroxide is conjugated to the tyrosine of the peptide.

6. A pharmaceutical composition comprising the nitration shielding peptide of claim 1 and a carrier suitable for in vivo administration to a subject.

7. A nitration shielding peptide comprising a nitration shielding domain comprising SEQ ID NO:21, SEQ ID NO:22, SEQ ID NO:23,
   wherein the nitration shielding peptide blocks protein nitration of RhoA,
   wherein the nitration shielding peptide is not full-length RhoA, and
   wherein the nitration shielding peptide is 9 to 15 amino acids in length and comprises a nitroxide conjugated to at least one amino acid of the nitration shielding peptide.

8. The nitration shielding peptide of claim 7 wherein the nitration shielding domain is 9 amino acids.

9. The composition of claim 7, wherein the nitroxide is conjugated to the tyrosine of the peptide.

10. A nitration shielding peptide that reduces or prevents nitration of a protein of interest comprising a nitration shielding domain comprising SEQ ID NO:20, wherein the nitration shielding peptide has a nitroxide conjugated to at least one amino acid of the nitration shielding peptide and is 11 amino acid in lengths.

11. A nitration shielding peptide that reduces or prevents nitration of a protein of interest comprising a nitration shielding domain comprising SEQ ID NO: 20, wherein the nitration shielding peptide has a 3-carboxy-2,2,5,5,-tetramethyl-3-pyrrolin-1-yloxy conjugated to at least one amino acid of the nitration shielding peptide.

* * * * *

UNITED STATES PATENT AND TRADEMARK OFFICE
CERTIFICATE OF CORRECTION

| | | |
|---|---|---|
| PATENT NO. | : 9,447,157 B2 | Page 1 of 1 |
| APPLICATION NO. | : 14/486317 | |
| DATED | : September 20, 2016 | |
| INVENTOR(S) | : Stephen M. Black et al. | |

It is certified that error appears in the above-identified patent and that said Letters Patent is hereby corrected as shown below:

In the Specification

Column 1, Line numbers 14-17, please replace the second paragraph as follows:

This invention was made with government support under HL101902 awarded by the National Institutes of Health. The government has certain rights in the invention.

Signed and Sealed this
Twelfth Day of June, 2018

Andrei Iancu
*Director of the United States Patent and Trademark Office*